(12) United States Patent
Fan et al.

(10) Patent No.: US 11,166,460 B2
(45) Date of Patent: Nov. 9, 2021

(54) α-AMINO ACRYLATE MICROBICIDE, AND PREPARATION METHOD THEREFOR AND USES THEREOF

(71) Applicant: NANKAI UNIVERSITY, Tianjin (CN)

(72) Inventors: Zhijin Fan, Tianjin (CN); Xiaolin Qian, Tianjin (CN); Jing Xue, Tianjin (CN); Aoben Wu, Tianjin (CN); Huaipu Yang, Tianjin (CN); Liuyong Ma, Tianjin (CN); Bin Yu, Tianjin (CN); Haixia Wang, Tianjin (CN); Nailou Zhang, Tianjin (CN); Qifan Wu, Tianjin (CN); Cenhui Han, Tianjin (CN); Jianyu Jin, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 0 days.

(21) Appl. No.: 16/614,352

(22) PCT Filed: May 17, 2017

(86) PCT No.: PCT/CN2017/084775
§ 371 (c)(1),
(2) Date: Apr. 4, 2020

(87) PCT Pub. No.: WO2018/209616
PCT Pub. Date: Nov. 22, 2018

(65) Prior Publication Data
US 2020/0236935 A1 Jul. 30, 2020

(30) Foreign Application Priority Data

May 16, 2017 (CN) .......................... 201710340933.9

(51) Int. Cl.
C07D 211/52 (2006.01)
A01N 43/40 (2006.01)
A01N 37/18 (2006.01)
A01N 43/50 (2006.01)
A01N 43/78 (2006.01)
A01N 43/82 (2006.01)
A01N 43/84 (2006.01)

(52) U.S. Cl.
CPC ............. *A01N 43/40* (2013.01); *A01N 37/18* (2013.01); *A01N 43/50* (2013.01); *A01N 43/78* (2013.01); *A01N 43/82* (2013.01); *A01N 43/84* (2013.01)

(58) Field of Classification Search
None
See application file for complete search history.

(56) References Cited

FOREIGN PATENT DOCUMENTS

WO WO 2004050613 A2 * 6/2004

OTHER PUBLICATIONS

Frankel et al., Journal of the Chemical Society (1952), pp. 289-291.*

* cited by examiner

*Primary Examiner* — Brian J Davis

(57) ABSTRACT

The present invention relates to a microbicidal α-amino acrylic derivative and its preparation method and applications. Based on the principle of pesticide molecular design, the structural reform of the agricultural anti-plant virus activity is carried on lead compounds having the medical anti-coronavirus activity, and a series of α-amino acrylic derivatives are designed and synthesized, and in particular, α-amino acrylic derivatives containing piperidine rings are synthesized, and the systematic biological activity screening is carried by using known compounds as positive control compounds, which provide many effective anti-virus leading molecules for the preparation of pesticides, and has positive significance to reduce the pesticide application dosage and protect the environment and ecology.

1 Claim, No Drawings

α-AMINO ACRYLATE MICROBICIDE, AND PREPARATION METHOD THEREFOR AND USES THEREOF

CROSS REFERENCE OF RELATED APPLICATION

This is a U.S. National Stage under 35 U.S.C 371 of the International Application PCT/CN2017/084775, filed May 17, 2017, which claims priority under 35 U.S.C. 119(a-d) to CN 201710340933.9, filed May 16, 2017.

BACKGROUND OF THE PRESENT INVENTION

Field of Invention

The present invention relates to a α-amino acrylic derivative, its preparation method and microbicidal applications. The present invention also relates to the novel heterocyclic derivatives as intermediate to prepare the α-amino acrylic derivative and the preparation method of the heterocyclic derivatives. This invention also relates to the pesticide combination which contains the above target compounds as active ingredients and its preparation. The compounds in this invention have microbicidal activity, especially fungicidal and anti-viral activities against plant virus. This invention related to the target compounds and its combination mixtures in the application of phytopathogenic microbe control in agriculture and horticulture. The above compounds and its combination mixtures can be used for controlling the microbe invasion in non-living materials.

Description of Related Arts

Plant pathogens such as viruses, fungi, and bacteria are one of the most important factors affecting modern agricultural production. The various plant diseases caused by these pathogens seriously affect the yield and quality of agricultural products. Plant viruses are widely found in nature, and diseases caused by them have brought huge losses on crop yields. Tobacco mosaic virus (TMV) is one of the most well studied plant viruses. It is one of the classic examples in virus studies on its morphological structure, chemical composition, assembling, coating, subunit composition, genomic structure, nucleic acid replication, protein translation, and virus movement between different cells. As a "cancer of plants", plant virus diseases are very difficult to be controlled. So far, only a few agents have been able to effectively control TMV. Therefore, it is urgent to find compounds with high activity for tobacco mosaic virus management, which has not only great theoretical and practical values, but also shows a broad prospect (Bos, L. Crop losses caused by viruses. *Crop Prot.* 1982, 1: 263-282).

Modern pesticides and pharmaceutical drugs are designed through specific biological targets with different functions. In some specific cases, their molecular targets and functions often overlap, or their targets share similar processes or molecules. For this reason, most pharmaceutical companies also have pesticide divisions, such as Dow, Dow Pharmaceuticals and Dow AgroSciences. These two divisions often evaluate most of the chemicals for both pharmaceutical and pesticide activities. Sometimes pesticides are developed as pharmaceuticals, or pharmaceuticals are developed for use as pesticides (Liu, Pengfei et al., Similarity of novel product development and management between pesticide and drug, *World Pesticides.* 2011, 33(6): 8-12).

The lead compound of the present invention has pharmaceutical activity and belongs to a α-amino acrylic derivative, which has significant activity against coronavirus (Anna Lundin, et al., Targeting membrane-bound viral RNA synthesis reveals potent inhibition of diverse coronaviruses including the middle east respiratory syndrome virus. *PLOS Pathogens.* 2014, 10(5): 1-15). This lead compound may have a novel mode of action.

Both coronavirus and tobacco mosaic virus are RNA viruses, and there is no report on anti-plant virus activity of anti-coronavirus agent. Therefore, the present invention conducted lead optimization against TMV by the principle of pesticide molecular designation, systematic structural derivation discovered highly active anti-TMV compounds.

On the other hand, chemical fungicide is one of the important means for the effective plant disease prevention and control to ensure the yield and quality of agricultural products. However, the widespread and unreasonable application of fungicides has resulted resistance against existing traditional fungicides in China (Jia, Junchao, et al., Progress on study on resistance mechanism of strobilurin fungicides, *Chinese Journal of Pesticide Science,* 2008, 10(1): 1-9). The strobilurin fungicide is one of the most widely used fungicides in agricultural farmland with significant resistance now (Ping Zhao, et al., Current status of resistance and development of strobilurin fungicide, *Agrochemicals.* 2011, 50(8): 547-551). Development of novel fungicides with simple structure and different mode of action is one of the effective ways to solve this problem.

Piperidine derivatives, such as fungicidal fenpropidin, herbicidal piperidane and plant growth regulating mepazine also exhibit a wide spectrum of biological activities in pesticides (Jiang Zhigan, et al., Design, synthesis and fungicidal activity of novel triazole derivatives containing substituted 1,2,3-triazole-piperidine side chains. *Eur. J. Med. Chem.* 2014, 82: 490-497). The study of combination of the active substructure thiazole and the piperidine has been reported in the patent (Black, et al. Novel herbicides, WO 2007071900 A1; Pasteris, et al. Fungicidal amides, WO 2008091580 A2).

Since the lead compound in the present invention also contains a piperidine ring, a series of derivatives were synthesized for fungicidal screening, some compounds were discovered with highly fungicidal activity.

A lead compound with anti-coronavirus activity was structurally derived according to the principle of pesticide molecular design in the present invention, a series of α-amino acrylic derivatives, especially piperidine ring containing α-amino acrylic derivatives were designed and synthesized. The reported compounds were used as positive control for biological comparison screening to provide highly active anti-plant virus agent in novel pesticide development. Some lead molecules with antiviral or fungicidal activity were discovered, which have positive significance for the reduction of the amount of pesticide application and the ecological environment protection.

SUMMARY OF THE PRESENT INVENTION

The technical problem which needs to be solved by the present invention is to provide a novel α-amino acrylic derivative and its synthetic methods, and its applications in the areas of agriculture, horticulture, health and forestry. Also, the present invention relates to new intermediates for preparing the α-amino acrylic derivative and their preparation methods. Moreover, the present invention relates to a pesticide composition including the α-amino acrylic derivative as an active ingredient, and its preparation method and applications.

The α-amino acrylic derivative provided by the present invention, accordingly, is a compound with a formula I of:

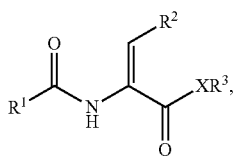

I wherein:

R$^1$ is hydrogen, C$_1$-C$_6$alkyl, C$_1$-C$_6$haloalkyl, C$_1$-C$_6$alkoxy, C$_1$-C$_6$haloalkoxy, C$_2$-C$_6$alkenyl, C$_2$-C$_6$haloalkenyl, C$_2$-C$_6$alkynyl, C$_2$-C$_6$haloalkynyl, hydroxyl, C$_3$-C$_6$cycloalkyl, substituted piperidin-1-yl, substituted morpholin-1-yl, substituted tetrahydropyrrole-1-yl, phenyl or C$_1$-C$_6$alkyl substituted phenyl or C$_1$-C$_6$haloalkyl substituted phenyl or C$_3$-C$_6$cycloalkyl substituted phenyl or nitro substituted phenyl, pyridyl, or C$_1$-C$_6$alkyl substituted pyridyl or C$_1$-C$_6$ haloalkyl substituted pyridyl or C$_3$-C$_6$cycloalkyl substituted pyridyl or nitro substituted pyridyl, substituted five- or six-membered heteroaryl containing one or two N atoms, substituted five- or six-membered heteroaryl containing one or two S atoms, substituted five- or six-membered heteroaryl containing one or two O atoms, substituted five- or six-membered heteroaryl containing one S atom and one N atom, substituted five- or six-membered heteroaryl containing one N atom and one O atom, substituted five- or six-membered heteroaryl containing two N atom and one S atom, or substituted five- or six-membered heteroaryl containing two N atom and one O atom; the aforementioned five- or six-membered heteroaryl is substituted furanyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothienyl, benzofuryl, benzimidazolyl, indazolyl, benzotriazolyl, benzothiazolyl, benzothiadiazolyl, benzoxazolyl, isomerized quinolinyl, isomerized isopropyl quinolinyl, phthalazinyl, quinoxalinyl, quinazolinyl, fluorinyl or naphthyridinyl; preferably, R$^1$ is methyl, cyclopropyl, cyclohexyl, 1-tert-butoxycarbonylpiperidin-4-yl, chloro-1-H-piperidin-4-yl, phenyl, 4-methoxyphenyl, 4-fluorophenyl, 4-chlorophenyl, 4-bromophenyl, 4-trifluoromethylphenyl, 4-nitrophenyl, 3-nitrophenyl, 2-nitrophenyl, 2-furyl, 2-thienyl, 4-methyl-1,2,3-thiadiazol-5-yl, 5-methyl-1,2,3-thiadiazol-4-yl, 3,4-dichloroisothiazol-5-yl, 2-(1-tert-butoxycarbonylpiperidin-4-yl)-thiazol-4-yl, 2-(1-piperidin-4-yl)-thiazole-4-yl, 1-tert-butoxycarbonylpiperidin-4-yl, or 1-chloropiperidin-4-yl;

R$^2$ is hydrogen, C$_1$-C$_6$alkyl, C$_1$-C$_6$haloalkyl, C$_1$-C$_6$alkoxy, C$_1$-C$_6$haloalkoxy, C$_2$-C$_6$alkenyl, C$_2$-C$_6$haloalkenyl, C$_2$-C$_6$alkynyl, C$_2$-C$_6$haloalkynyl, hydroxyl, C$_3$-C$_6$cycloalkyl, substituted piperidin-1-yl, substituted morpholin-1-yl, substituted tetrahydropyrrole-1-yl, phenyl or C$_1$-C$_6$ alkyl substituted phenyl or C$_1$-C$_6$haloalkyl substituted phenyl or C$_3$-C$_6$cycloalkyl substituted phenyl or nitro substituted phenyl, pyridyl, or C$_1$-C$_6$alkyl substituted pyridyl or C$_1$-C$_6$ haloalkyl substituted pyridyl or C$_3$-C$_6$cycloalkyl substituted pyridyl or nitro substituted pyridyl, substituted five- or six-membered heteroaryl containing one or two N atoms, substituted five- or six-membered heteroaryl containing one or two S atoms, substituted five- or six-membered heteroaryl containing one or two O atoms, substituted five- or six-membered heteroaryl containing one S atom and one N atom, substituted five- or six-membered heteroaryl containing one N atom and one O atom, substituted five- or six-membered heteroaryl containing two N atom and one S atom, or substituted five- or six-membered heteroaryl containing two N atom and one O atom; the aforementioned five- or six-membered heteroaryl is substituted furanyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothienyl, benzofuryl, benzimidazolyl, indazolyl, benzotriazolyl, benzothiazolyl, benzothiadiazolyl, benzoxazolyl, isomerized quinolinyl, isomerized isopropyl quinolinyl, phthalazinyl, quinoxalinyl, quinazolinyl, fluorinyl or naphthyridinyl; preferably, R$^2$ is methyl, cyclopropyl, cyclohexyl, 1-tert-butoxycarbonylpiperidin-4-yl, chloro-1-H-piperidin-4-yl, phenyl, 4-methoxyphenyl, 4-fluorophenyl, 4-chlorophenyl, 4-bromophenyl, 4-trifluoromethylphenyl, 4-nitrophenyl, 3-nitrophenyl, 2-nitrophenyl, 2-furyl, 2-thienyl, 4-methyl-1,2,3-thiadiazol-5-yl, 5-methyl-1,2,3-thiadiazol-4-yl, 3,4-dichloroisothiazol-5-yl, 2-(1-tert-butoxycarbonylpiperidin-4-yl)-thiazol-4-yl, 2-(1-piperidin-4-yl)-thiazole-4-yl, 1-tert-butoxycarbonylpiperidin-4-yl, or 1-chloropiperidin-4-yl;

X is S or O or N or NH;

R$^3$ is hydrogen, C$_1$-C$_6$alkyl, C$_1$-C$_6$haloalkyl, C$_1$-C$_6$alkoxy, C$_1$-C$_6$haloalkoxy, C$_2$-C$_6$alkenyl, C$_2$-C$_6$haloalkenyl, C$_2$-C$_6$alkynyl, C$_2$-C$_6$haloalkynyl, hydroxyl, C$_3$-C$_6$cycloalkyl, substituted piperidin-1-yl, substituted morpholin-1-yl, substituted tetrahydropyrrole-1-yl, phenyl or C$_1$-C$_6$ alkyl substituted phenyl or C$_1$-C$_6$haloalkyl substituted phenyl or C$_3$-C$_6$cycloalkyl substituted phenyl or nitro substituted phenyl, pyridyl, or C$_1$-C$_6$alkyl substituted pyridyl or C$_1$-C$_6$ haloalkyl substituted pyridyl or C$_3$-C$_6$cycloalkyl substituted pyridyl or nitro substituted pyridyl, substituted five- or six-membered heteroaryl containing one or two N atoms, substituted five- or six-membered heteroaryl containing one or two S atoms, substituted five- or six-membered heteroaryl containing one or two O atoms, substituted five- or six-membered heteroaryl containing one S atom and one N atom, substituted five- or six-membered heteroaryl containing one N atom and one O atom, substituted five- or six-membered heteroaryl containing two N atom and one S atom, or substituted five- or six-membered heteroaryl containing two N atom and one O atom; the aforementioned five- or six-membered heteroaryl is substituted furanyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothienyl, benzofuryl, benzimidazolyl, indazolyl, benzotriazolyl, benzothiazolyl, benzothiadiazolyl, benzoxazolyl, isomerized quinolinyl, isomerized isopropyl quinolinyl, phthalazinyl, quinoxalinyl, quinazolinyl, fluorinyl or naphthyridinyl; preferably, R$^3$ is methyl, methoxy, methyl propionate-2-yl, methyl propionate-3-yl, methyl butyrate-4-yl, difluoroethyl, substituted phenylmethyl; the substituted phenylmethyl is preferably phenylmethyl, 4-bromophenylmethyl, 3-bromophenylmethyl, 2-bromophenylmethyl, 4-methoxyphenylmethyl, 3-methoxy phenylphenylmethyl, 2-methoxyphenylmethyl, 4-fluorophenylmethyl, 3-fluorophenylmethyl, 2-fluorophenylmethyl, 4-chlorophenylmethyl, 3-chlorophenylmethyl, 2-chlorophenylmethyl, 4-trifluoromethylphenylmethyl, 3-trifluoromethylphenylmethyl, 2-trifluoromethylphenylmethyl, 4-trifluoromethoxyphenylmethyl, 3-trifluoromethoxyphenylmethyl, 2-trifluoromethoxyphenylmethyl, furan-2-methyl, thiophen-2-methyl, pyrrole-2-methyl, pyrimidine-2-methyl, 4-methyl-1,2,3-thiadiazole-5-methyl, 5-methyl-1,2,3-thiadiazole-4-methyl, 3,4-dichloroisothiazol-5-methyl, 2-(1-tert-butoxycarbonylpiperidin-4-yl)-thiazole-4-methyl, 2-(1-piperidine chloride-4-yl)-thiazole-4-methyl, 1-tert-butoxycarbonylpiperidine-4-methyl, or 1-piperidine chloride-4-methyl;

or:

XR³ together constitutes substituted five- or six-membered heterocyclic containing one or two N atoms, substituted five- or six-membered heterocyclic containing one N and one S atoms, substituted five- or six-membered heterocyclic substituents containing one N atom and one O atom; preferably, XR³: when X is NH, O, or S, R³ is methyl, methoxy, trifluoromethyl, trifluoromethoxy, cyclopropyl, cyclohexyl, methyl propionate-2-methyl, propionate-3-yl, methyl butyrate-4-yl, difluoroethyl, substituted phenylmethyl, substituted piperidin-1-yl, substituted tetrahydropyrrole-1-methyl, morpholin-1-yl, phenyl, 4-methoxyphenyl, 4-fluorophenyl, 4-chlorophenyl, 4-bromophenyl, 4-trifluoromethylphenyl, 4-nitrophenyl, 3-nitrophenyl, 2-nitrophenyl, 2-furanyl, 2-thienyl, 4-methyl-1,2,3-thiadiazol-5-yl, 5-methyl-1,2,3-thiadiazol-4-yl, 3,4-dichloroisothiazol-5-yl, benzyl, 4-methoxyphenylmethyl, 4-fluorophenylmethyl, 4-chlorophenylmethyl, 4-bromophenylmethyl, 4-trifluorophenylmethyl, 4-nitrophenylmethyl, 3-nitrophenylmethyl, 2-nitrophenylmethyl, furan-2-methyl, thiophene-2-methyl, 4-methyl-1,2,3-thiadiazole-5-methyl, 5-methyl-1,2,3-thiadiazole-4-methyl, or 3,4-dichloroisothiazol-5-methyl; the substituted piperidin-1-yl is preferably 4-hydroxypiperidin-1-yl, 4-hydroxy-4-(4'-bromophenyl)-piperidin-1-yl 4-hydroxy-4-phenylpiperidin-1-yl, or 4-(4'-hydroxymethyl) thiazol-2-ylpiperidin-1-yl; the substituted tetrahydropyrrole-1-yl is preferably 2-methoxycarbonyltetrahydropyrrole-1-yl;

Optionally, the double bond connected to R² is a single bond.

In the above definition, halogen is fluorine, chlorine, bromine or iodine.

The alkyl, alkenyl or alkynyl may be linear or branched;

Depending on the number of carbon atoms mentioned, the alkyl group itself or as part of another substituent is methyl, ethyl, propyl, butyl, pentyl, hexyl and its isomers or isopropyl, isobutyl, sec-butyl, tert-butyl, isopentyl or tert-pentyl;

The haloalkyl group may contain one or more of the same or different halogen atoms, and the representative group is $CH_2Cl$, $CHCl_2$, $CCl_3$, $CH_2F$, $CHF_2$, $CF_3$, $CF_3CH_2$, $CH_3CF_2$, $CF_3CF_2$ or $CCl_3CCl_2$.

Depending on the number of carbon atoms mentioned, the cycloalkyl group itself or as part of another substituent is cyclopropyl, cyclobutyl, cyclopentyl or cyclohexyl;

Depending on the number of carbon atoms mentioned, the alkenyl group itself or the part as other substituent is, for example, vinyl, allyl, 1-propenyl, buten-2-yl, butene-3-yl, pentene-1-yl, penten-3-yl, hexen-1-yl or 4-methyl-3-pentenyl.

Depending on the number of carbon atoms mentioned, the alkyne group itself or part of other substituents is for example ethynyl, propyn-1-yl, propyn-2-yl, butyn-1-yl, butyn-2-yl, 1-methyl-2-butynyl, hexyn-1-yl, or 1-ethyl-2-butynyl;

The presence of one or more possible asymmetric carbon atoms in the formula I which is α-amino acrylic derivative means that the compound can occur in the form of optical isomers, the optical isomers comprises enantiomers and diastereo-isomers constituency. Due to the existence of possible aliphatic C═C double bonds, geometric isomerism, that is, cis-trans or (Z)-(E) isomerism; atropisomers may also occur due to restricted rotation around single bonds; the formula I is intended to include all these possible isomeric forms and mixtures thereof. The present invention is intended to include all these possible isomeric forms of compounds of formula I and mixtures thereof.

The group definition of the preferred α-amino acrylic derivative of the general formula I of the present invention is as follows:

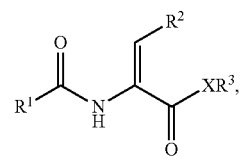

wherein:

R¹ is methyl, cyclopropyl, cyclohexyl, 1-tert-butoxycarbonyl-4-piperidinyl, chloro-4-piperidinyl, 4-methoxyphenyl, 4-fluorophenyl, 4-chlorobenzene, 4-bromophenyl, 4-trifluoromethylphenyl, 4-nitrophenyl, 3-nitrophenyl, 2-nitrophenyl, 2-furanyl, 2-thienyl, or phenyl;

R² is phenyl, 4-methylphenyl, 4-methoxyphenyl, 4-fluorophenyl, 4-chlorophenyl, 4-bromophenyl, 4-trifluoromethylphenyl, 3-trifluoromethylphenyl, 2-trifluoromethylphenyl, 4-phenylnitro, 4-trifluoromethylphenyl, furyl-2-yl, thienyl-2-yl, 1H-imidazolyl, 4-methyl-1,2,3-thiadiazol-5-yl, 5-methyl-1,2,3-thiadiazol-4-yl, or 4-(2-(1-tert-butoxycarbonyl-4)-piperidinyl) thiazol-4-yl);

R³ is methyl, methoxy, difluoroethyl, (R)-2-propanoic acid methyl ester, 1-propionic acid methyl ester, 1-butyric acid methyl ester, cyclopropyl, cyclohexyl, 4-bromobenzyl, 3-bromobenzyl, 2-bromobenzyl, benzyl, 4-methoxybenzyl, 4-fluorobenzyl, 4-chlorobenzyl, 4-trifluoromethylbenzyl, 2-thiophenebenzyl, 4-bromophenylmethoxy, or thienylmethyl;

X is N; or

XR³ is methyl pyrrolate, (R)-(2-methoxycarbonyl)pyrrolidin-1-yl, 4-hydroxypiperidin-1-yl, morpholin-1-yl, [4-(4-bromobenzene)-4-hydroxy]-1-piperidinyl, [4-[2-(4-thiazoleacetate)]]-1-piperidinyl, or [4-[2-(4-hydroxymethylthiazole))]]-1-piperidinyl, (4-phenyl)-1-piperidinyl.

Optionally, the double bond connected to R² is a single bond.

DETAILED DESCRIPTION OF THE PREFERRED EMBODIMENT (1) A Method for Synthesizing a α-Amino Acrylic Derivative of the Present Invention The general method of synthesizing the α-amino acrylic derivative I of the present invention is as follows:

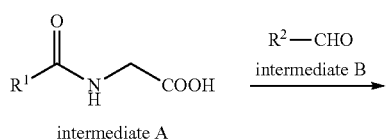

intermediate A

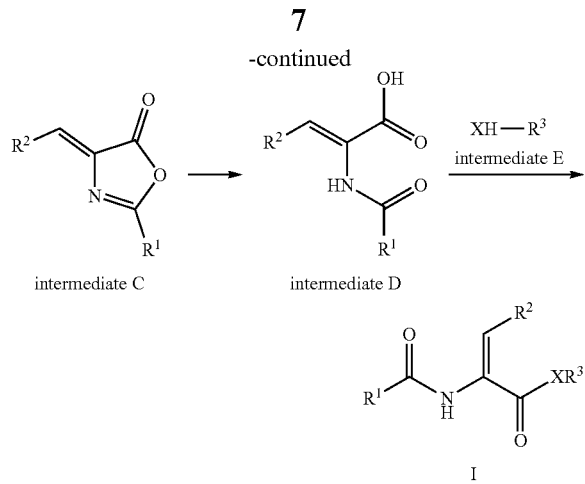

intermediate C    intermediate D

I

The definition of substituent groups R', R² and R³ is as mentioned above.

(A) General Procedure for the Synthesis of an Intermediate A:

The intermediate A is prepared from the reaction of corresponding acids R¹COOH or acid chloride R¹COCl with α-aminocarboxylic acid or corresponding ester of α-aminocarboxylic acid. If the ester is used as a raw material, the ester of intermediate A is obtained, and then the intermediate A is obtained through hydrolyzing the ester. The substituent R¹ is defined as above.

(B) General Procedure for the Synthesis of an Intermediate B:

The intermediate B is obtained by the oxidation reaction of corresponding alcohol R²—CH₂OH. The substituent R² is defined as above.

(C) General Procedure for the Synthesis of an Intermediate C:

The intermediate C is synthesized by heating reaction of the intermediates A with B, its detailed steps are described below:

In a two-necked round bottom flask, the intermediate A (10 mmol) and AcONa (12 mmol) were added under nitrogen atmosphere, and then Ac₂O (15 mL) was added to obtain a mixture. Then the mixture was stirred at room temperature for half an hour. Then the intermediate B (10 mmol) was added, and the temperature was increased to 60° C. for 4 h. After the reaction was completed, the reaction mixture was cooled to room temperature, and then the reaction mixture was transferred the beaker, water (150 mL) was added and stirred for 3 h at room temperature, and the yellow solid was precipitated. By filtration, the filter cake was washed with a small amount of water, dried under infrared light to obtain the intermediate C. And then, the mass of the intermediate C was weighed, its yield was calculated and its physicochemical characteristics including melting point, NMR and MS were determined. The amount of each raw material in each reaction, the amount of the intermediate C prepared and the volume of each reactor are appropriately increased or decreased according to the specific conditions; the substituents R¹ and R² in the intermediate C are described as above.

(D) General Procedure for the Synthesis of an Intermediate D:

The intermediate D is obtained by acidification after hydrolysis of the intermediate C, and the specific steps are described below:

The intermediate C (1.38 g) was added to a 1000 mL round bottom flask with THF (200 mL) as a solvent, and then an aqueous solution (200 mL) of sodium hydroxide (9.88 mmol) was added, and stirred at room temperature for 4 h. After the reaction was completed, THF was removed via rotavaper, and the insoluble material was filtered. pH was adjusted to 1-2 with concentrated hydrochloric acid, and the solid was precipitated. After filtration and drying under the ultra-IR light, the intermediate D was obtained. And then, the mass of the intermediate D was weighed, its yield was calculated and its physicochemical characteristics including melting point, NMR and MS were determined. The amount of each raw material in each reaction, the amount of the intermediate D prepared and the volume of the reactor are appropriately increased or decreased depending on the specific conditions; the substituents R¹ and R² in the intermediate D are defined as above.

(E) General Procedure for the Synthesis of the α-Amino Acrylic Derivative I:

The α-amino acrylic derivative I was synthesized by the reaction of the intermediates D and E, the specific steps are described below:

The intermediate D (0.27 g) was added to a 50 mL round bottom flask, DMF (about 10 mL) was added. Then PyBOP (0.95 mmol), the intermediate E (1.08 mmol, HX-R³) and DIPEA (2.25 mmol) were added for stirring at room temperature overnight. After the reaction was completed, and then the reaction mixture was transferred the 100 mL beaker, brine (about 80 mL) was added, and a large amount of white solid was precipitated. After filtration, the solid was dissolved in ethyl acetate, dried over anhydrous sodium sulfate, and then subjected to column chromatography to obtain the final product α-amino acrylic derivative I. And then, the mass of the final product α-amino acrylic derivative I was weighed, its yield was calculated and its physicochemical characteristics including melting point, NMR and MS were determined. The amount of each raw material in each reaction, the amount of the α-amino acrylic derivative I and the volume of each reactor are appropriately increased or decreased according to the specific conditions. The definitions of the substituents R¹, R², R³ and XR³ in the α-amino acrylic derivative I and the intermediate E (HX-R³) are defined as above.

Preparation of Compounds

The present invention explains the synthesis, biological activities and applications of α-amino acrylic derivative I more specifically through specific preparation and biological activity measurement examples. The examples are only used to specifically illustrate the present invention and not to limit the present invention, especially biological activities which are only illustrative and not the limitation of the present invention. The synthetic methods of some compounds are described in detail below. Unless otherwise specified, the definitions of the substituents R¹, R², R³, and XR³ are as described above.

When XR³ constitutes a substituted piperidine, its chemical structure IA is as follows:

IA

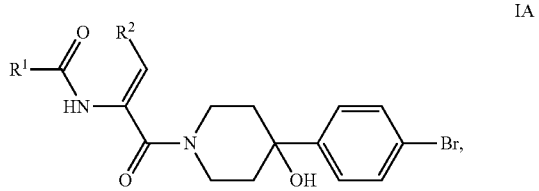

wherein: the substituents represented by $R^1$ and $R^2$ are as described above, and preferably, when $R^2$ is phenyl, $R^1$ is methyl, cyclopropyl, cyclohexyl, 1-tert-butoxycarbonyl-4-piperidyl, chloro-4-piperidinyl, 4-methoxyphenyl, 4-fluorophenyl, 4-chlorophenyl, 4-bromophenyl, 4-trifluoromethylphenyl, 4-nitrophenyl, 3-nitrophenyl, 2-nitrophenyl, 2-furanyl, 2-thienyl, or phenyl.

When $R^1$ is phenyl, the piperidine derivative IA of the present invention is specifically represented by compound g, and its synthesis method is as follows:

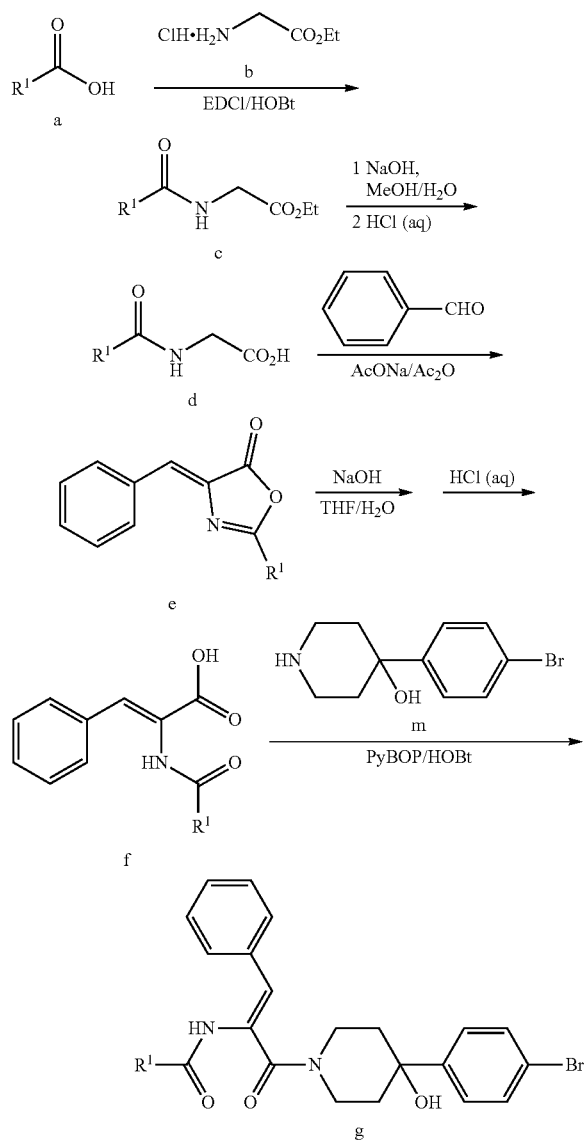

Synthesis Example 1: General Procedure for the Synthesis of Compound 5

The compound 5: (Z)—N-[1-[[4-(4-bromophenyl)-4-hydroxy]-1-piperidinyl]carbonyl]-2-phenylvinyl]-1-piperidine-4-methoxybenzamide When $R^1$ is methoxyphenyl, the synthesis of compound 5 was as follow; and at this condition, the compound g is just the compound 5.

4-Methoxybenzoic acid a (2.00 g) was added to a 200 mL round bottom flask, and then DCM (60 mL) was added; 13.80 mmol EDCI, 13.80 mmol HOBt, 15.77 mmol b, 45.99 mmol Et$_3$N were added dropwise in sequence to obtain a mixture. The mixture was then stirred at room temperature overnight. After the reaction was completed, the reaction mixture was separated to two layers; the organic layer was washed with water, saturated ammonium chloride solution and saturated brine, dried over anhydrous sodium sulfate, and then concentrated under reduced pressure. The residue was purified by column chromatography with a mixture of petroleum ether/ethyl acetate/5:1-2:1, v/v) to give 1.80 g of compound c with yield 62.7%. And then, to a solution of compound c in MeOH (45 mL), 15.19 mmol sodium hydroxide aqueous solutions (45 mL) were added. The reaction mixture was then stirred under reflux for 3 h. After cooling the reaction mixture to the room temperature, the solvent was removed via rotavapor, and then a small amount of water was added. The mixture was transferred to the beaker and adjusted to a pH value of 1-2 with concentrated hydrochloric acid solution, the mixture was then extracted with ethyl acetate, the organic layer was washed with brine, and then was dried over anhydrous sodium sulfate, after filtration, the organic layer was concentrated under the reduced pressure to give 1.22 g white solid of compound d with yield 76.5%. $^1$H NMR (400 MHz, DMSO) δ 12.59 (s, 1H), 8.71 (t, J=5.8 Hz, 1H), 7.85 (d, J=8.8 Hz, 2H), 7.02 (d, J=8.8 Hz, 2H), 3.90 (d, J=5.9 Hz, 2H), 3.82 (s, 3H).

The compound d (1.20 g) and 6.89 mmol AcONa were added to a 100 mL two-necked flask, and Ac$_2$O (20 mL) under nitrogen atmosphere was added to obtain a mixture, the mixture was stirred at room temperature for 0.5 h, and then 5.74 mmol benzaldehyde was added. The mixture was stirred at 60° C. for 4 h. After cooling the mixture to the room temperature, the substance in the flask was transferred to the beaker, and then 120 mL water was added and stirred at room temperature for 3 h. A yellow solid was precipitated and filtrated to give 1.39 g (yield 86.3%) of compound e by dryness under the IR light. $^1$H NMR (400 MHz, CDCl$_3$) δ 8.25-8.11 (m, 4H), 7.52-7.41 (m, 3H), 7.20 (s, 1H), 7.03 (d, J=8.9 Hz, 2H), 3.92 (s, 3H). To a 1000 mL round-bottomed flask, the compound e (1.38 g), tetrahydrofuran (THF) (200 mL) and 9.88 mmol sodium hydroxide solutions were added to obtain a mixture. The mixture was stirred at room temperature for 4 h. The tetrahydrofuran was removed by distillation, the insoluble matter was filtered off, and a pH value of the filtrate was adjusted to 1-2 with concentrated hydrochloric acid and filtrated to give 1.15 g (yield 78.2%) of compound f by dryness under the IR light. $^1$H NMR (400 MHz, DMSO) δ 12.74 (s, 1H), 9.82 (s, 1H), 7.97 (d, J=8.7 Hz, 2H), 7.66 (d, J=6.9 Hz, 2H), 7.38 (dd, J=14.0, 6.4 Hz, 4H), 7.06 (d, J=8.8 Hz, 2H), 3.84 (s, 3H).

The compound f (0.27 g) was added to a 50 mL round-bottomed flask, and then DMF (about 10 mL) was added; 0.95 mmol PyBOP, 1.08 mmol the compound m, 2.25 mmol DIPEA were added in sequence to obtain a mixture. The mixture was stirred at room temperature for overnight. After transfer the mixture to 100 mL beaker, 80 mL brine was added and a white solid was precipitated. After filtration, the solid was then dissolved in ethyl acetate and dried over anhydrous sodium sulfate, purified by column chromatography with a mixture of petroleum ether/ethyl acetate/3:1-1:2, v/v) as an eluent to give 0.45 g (yield 93.8%) of the final product g, that is, the compound 5: (Z)—N-[1-[[4-(4-bromophenyl)-4-hydroxy]-1-piperidinyl]carbonyl]-2-phenylvinyl]-1-piperidine-4-methoxybenzamide. The structural parameters are shown in Table 1.

Specifically: when R¹ is methyl or phenyl, the intermediate product of d in the second synthetic step can be purchased directly at low cost; when R¹ is cyclopropyl, the synthesis of the intermediate d in the second synthetic step is synthesized as follows, and other intermediate compounds d can also be synthesized by the following method too:

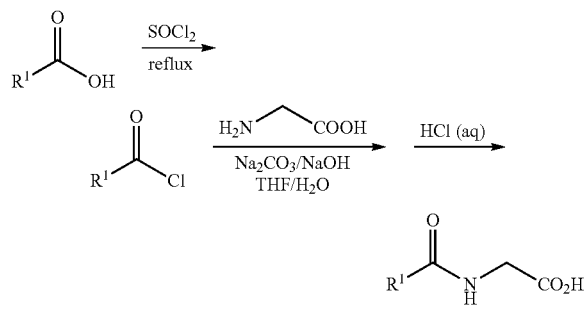

When R¹ is a phenyl group, R² is 4-methylphenyl, 4-methoxyphenyl, 4-fluorophenyl, 4-chlorophenyl, 4-bromophenyl, 4-trifluoromethylphenyl, 3-trifluoromethylphenyl, 2-trifluoromethylphenyl, 4-phenylnitro, 2-furyl, 2-thifenyl, 1H-imidazolyl, 4-methyl-1,2,3-thiadiazol-5-yl, 5-methyl-1,2,3-thiadiazol-4-yl, or 4-(2-(1-tert-butoxycarbonyl-4-piperidinyl))thiazol-4-yl).

When R¹ is a methyl and R² is a 4-trifluoromethylphenyl, the synthesis of the piperidine derivative IA was shown as described below:

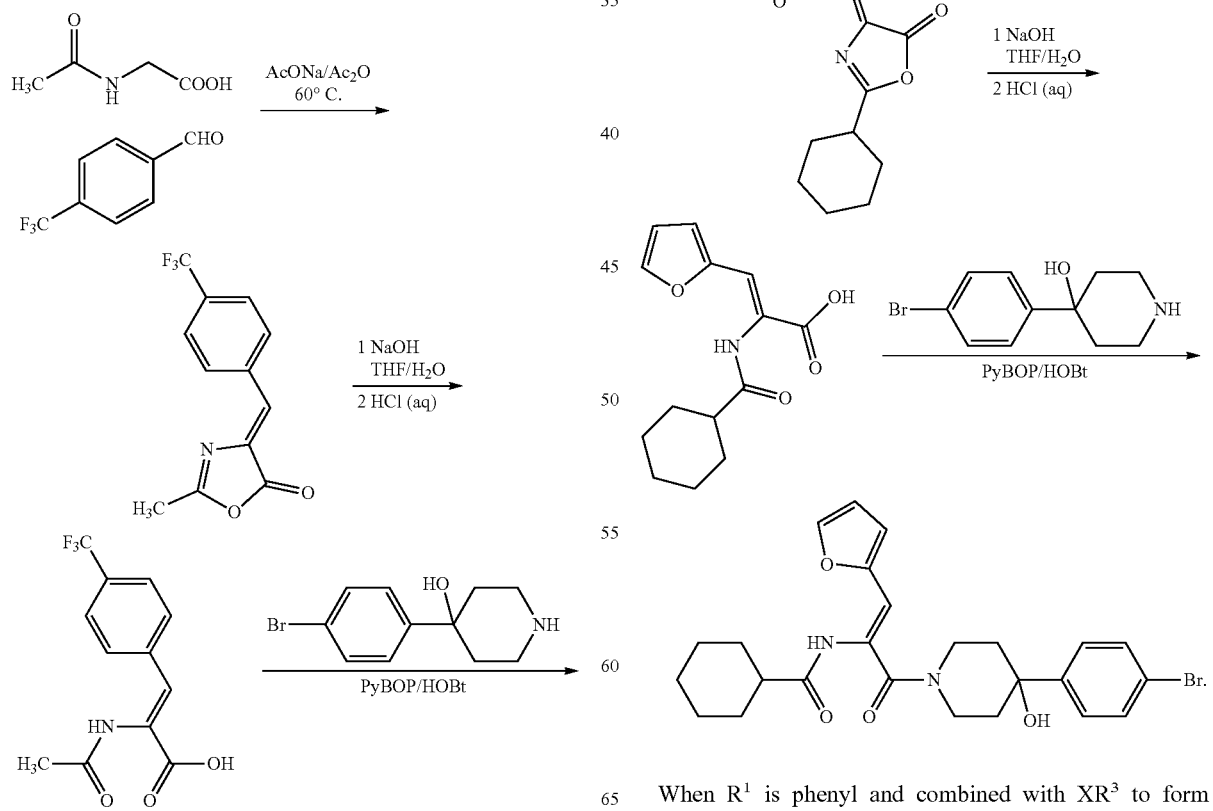

When R¹ is a cyclohexyl and R² is a furan-2-yl, the synthesis of the piperidine derivative IA was shown as bellow:

When R¹ is phenyl and combined with XR³ to form substituted piperidines, the chemical structures of the target molecules were shown as IB:

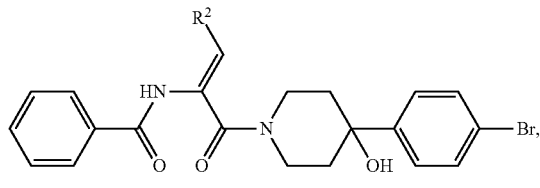

wherein: the substituent of $R^2$ is defined as above, and preferably $R^2$ is: 4-methoxyphenyl, 4-fluorophenyl, 4-chlorophenyl, 4-bromophenyl, 4 trifluoromethylphenyl, 3-trifluoromethylphenyl, 2-trifluoromethylphenyl, 4-phenylnitro, furan-2-yl, thiophen-2-yl, 1H-imidazolyl, 4-methyl-1,2,3-thiadiazolyl, 5-1,2,3-thiadiazolyl, or 4-(2-(1-tert-butoxycarbonyl-4-piperidyl)thiazol-4-yl).

The synthesis of piperidine-containing α-amino acrylic derivative 1B was as follows:

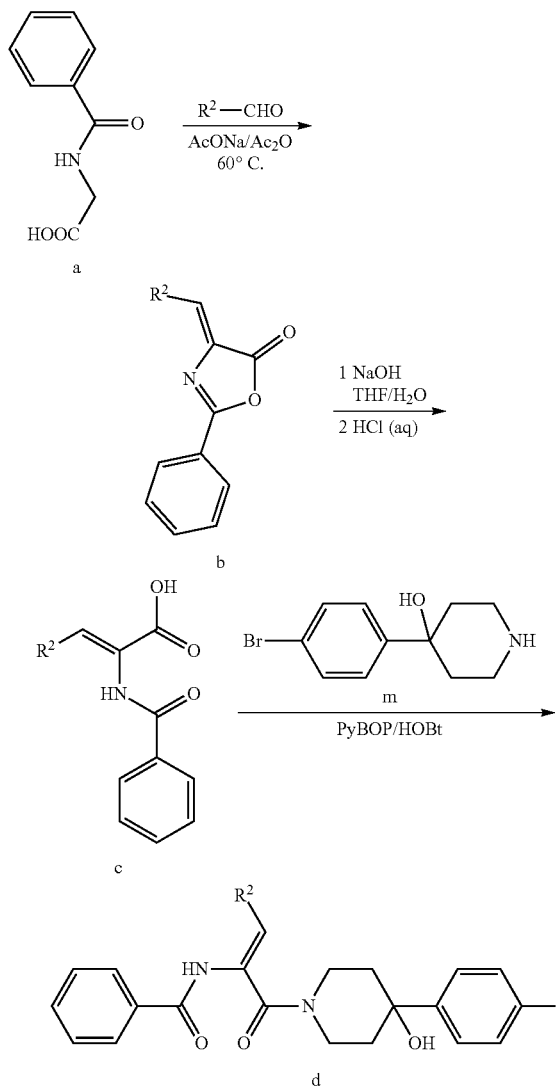

Specifically, when $R^2$ is 4-methyl-1,2,3-thiadiazol-5-yl, 5-methyl-1,2,3-thiadiazol-4-yl, 2-(1'-tert-butoxycarbonylpiperidin-4-yl)thiazol-4-yl, one starting material was an aldehyde $R^2$—CHO, and their preparation routs were described below:

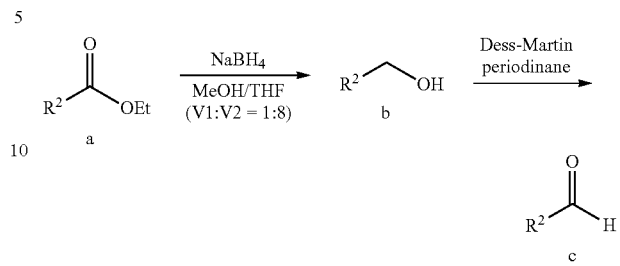

Synthesis Example 2: General Procedure for the Synthesis of Compounds b and c When $R^2$ is 2-(1'-tert-butoxycarbonylpiperidin-4-yl) thiazol-4-yl, the synthesis of the compounds b and c was as follows:

To a solution of the compound a (5.00 g) in THF (160 mL) and MeOH (20 mL), 44.06 mmol-117.50 mmol NaBH$_4$ were added to obtain a mixture. The mixture was then stirred at room temperature. After the reaction was completed, the mixture was transferred to beaker and dissolved in water, then it was extracted with ethyl acetate, the combined organic layers were washed with saturated brine, dried over anhydrous sodium sulfate, and the residue was purified by column chromatography on silica gel with a mixture of ethyl acetate/petroleum ether (60-90° C. fraction) (1:4-1:1, v/v) to give 3.36 g (yield 76.7%) of the compound b. $^1$H NMR (400 MHz, CDCl$_3$) δ 7.10 (s, 1H), 4.76 (s, 2H), 4.21 (s, 2H), 3.14 (ddd, J=11.7, 8.0, 3.7 Hz, 1H), 2.87 (s, 2H), 2.09 (d, J=12.9 Hz, 2H), 1.72 (dd, J=12.6, 3.9 Hz, 2H), 1.48 (s, 9H).

To a solution of the compound b (0.95 g) in DCM (30 mL), and then 3.18 mmol of Dess-Martin oxidant was added in portions, and stirred at room temperature. The suspension was filtered and concentrated under reduced pressure after the reaction was completed. The residue was purified by silica gel column chromatography with ethyl acetate/petroleum ether (60-90° C. fraction) (1:6-1:3, v/v) as an eluent to give 0.81 g (yield 86.2%) of the compound c. $^1$H NMR (400 MHz, CDCl$_3$) δ 10.02 (s, 1H), 8.12 (s, 1H), 4.25 (s, 2H), 3.25 (ddd, J=15.2, 7.6, 3.7 Hz, 1H), 2.92 (s, 2H), 2.16 (d, J=12.5 Hz, 2H), 1.79 (qd, J=12.4, 4.1 Hz, 2H), 1.47 (d, J=18.4 Hz, 9H). The compound a thiazolpiperidine ester is prepared by the laboratory of inventors.

Synthesis Example 3: General Procedure for the Synthesis of the Compound 16

Compound 16: (Z)—N-[1-[[4-(4-bromophenyl)-4-hydroxy]piperidinyl]carbonyl]-2-(4-methoxyphenyl)ethene benzoylamide When $R^2$ is 4-methoxyphenyl, d is the compound 16, and the synthesis of compound 16 was described as follows:

of the compound a (1.00 g) and 6.70 mmol AcONa were added to a 100 mL two-necked flask, and then Ac$_2$O (20 mL) was added under nitrogen atmosphere to obtain a mixture, the mixture was stirred at room temperature for 0.5 h, and then 5.58 mmol benzaldehyde was added. Then the mixture was stirred at 60° C. for 4 h. After cooling the mixture to the room temperature, the substance in the flask was transferred to the beaker, 120 mL water was added and stirred at room temperature for 3 h. A solid was precipitated and filtrated to give 0.96 g (yield 61.5%) of the compound b by washing it with small amount of water and dryness under the IR light after filtration. ¹H NMR (400 MHz, CDCl₃) δ 8.18 (dd, J=11.1, 8.2 Hz, 4H), 7.56 (dt, J=29.3, 7.3 Hz, 3H), 7.24 (d, J=17.8 Hz, 1H), 7.00 (d, J=8.8 Hz, 2H), 3.89 (s, 3H). To a 100 mL round-bottomed flask, the compound b (0.94 g), tetrahydrofuran (THF) (30 mL) and 6.73 mmol sodium hydroxide solution were added to obtain a mixture. The mixture was stirred at room temperature for 4 h. The tetrahydrofuran was removed by distillation, and the insoluble matter was filtered off. Then a pH value of the filtrate was adjusted to 1-2 with concentrated hydrochloric acid and after filtration and drying under the IR light to give 0.89 g (yield 89.0%) of the compound c. ¹H NMR (400 MHz, DMSO) δ 12.67 (s, 1H), 9.90 (s, 1H), 8.02 (d, J=7.4 Hz, 2H), 7.75-7.43 (m, 6H), 6.97 (d, J=8.8 Hz, 2H), 3.76 (s, 3H).

The compound c (0.17 g) was added to a 50 mL round-bottomed flask, and then DMF (10 mL) was added; 0.60 mmol PyBOP, 0.68 mmol the compound m and 1.43 mmol DIPEA were added in sequence to obtain a mixture. The mixture was stirred at room temperature for overnight. And then, the reaction mixture was transferred to 100 mL beaker, 80 mL brine was added and a white solid was precipitated. After filtration, the solid was dissolved in ethyl acetate and dried over anhydrous sodium sulfate, purified by column chromatography with ethyl acetate/petroleum ether (60-90° C. fraction) (1:2-1:0, v/v) as an eluent to give the compound d, that is, the compound 16: (Z)—N-[1-[[4-(4-bromophenyl)-4-hydroxy]piperidinyl]carbonyl]-2-(4-methoxyphenyl)ethene benzoylamide. The structural parameters were shown in Table 1.

Compound 30: piperidine α-amino acrylic derivative containing thiazole, whose chemical structure is as follows:

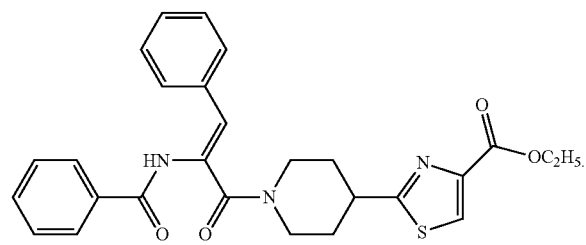 [SMILES: CCOC(=O)c1csc(C2CCN(C(=O)/C(=C/c3ccccc3)NC(=O)c3ccccc3)CC2)n1]

The synthesis method of the compound 30 piperidine α-amino acrylic derivative containing thiazole is as follows:

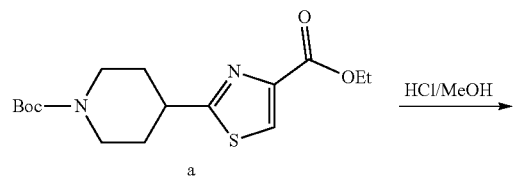

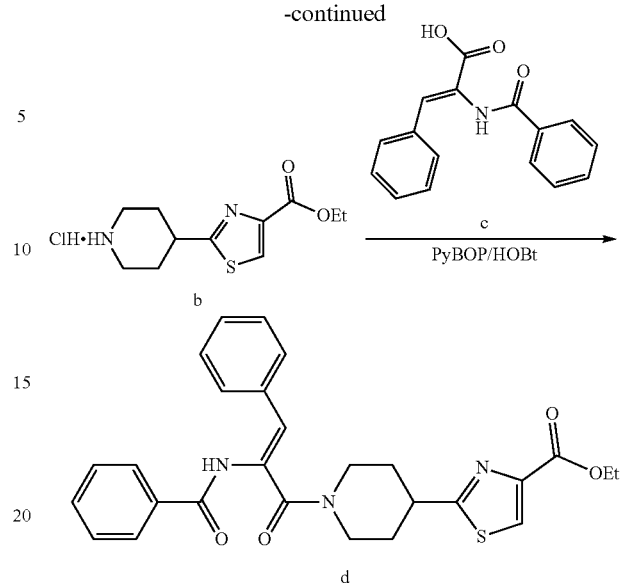

Synthesis Example 4: Preparation of Compound 30

Compound 30: (Z)—N-[1-[[[4-[2-(4-thiazolylacetate)]]-1-piperidinyl]carbonyl]-2-phenylvinyl]benzamide.

The compound a (1.81 g) was added to a 100 ml round-bottomed flask, then 20 mL of 3 Mol/mL HCl/MeOH was added. After stirring at room temperature for 2 h, a large amount of white solid was formed, which was filtered and dried to give 1.37 g (yield 96.5%) of the compound b.

The compound c (0.83 g) was added to a 100 ml round-bottomed flask, then 30 mL, DCM was added; and then 3.27 mmol PyBOP, 3.73 mmol b and 7.78 mmol DIPEA were added in sequence to obtain a mixture. The mixture was stirred at room temperature for overnight. The organic layers of the mixture was washed with water, saturated ammonium chloride solution and saturated brine in sequence, dried over anhydrous sodium sulfate, and then concentrated under reduced pressure. The residue was purified by column chromatography on silica gel with a mixture of ethyl acetate and petroleum ether (1:5-1:3, v/v) to give a 1.44 g (yield 94.7%) of the compound d as a white solid. The compound d was just the compound 30: (Z)—N-[1-[[[4-[2-(4-thiazolylacetate)]]-1-piperidinyl]carbonyl]-2-phenylvinyl]benzamide, the structural parameters were shown in Table 1.

Hydroxymethylthiazolidine-containing α-amino acrylic derivative is compound 31 with a formula as below:

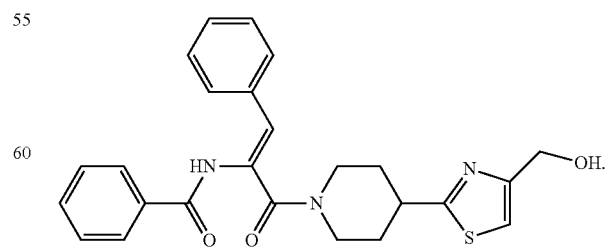

The synthesis method of the piperidine derivative compound 31 is as follows:

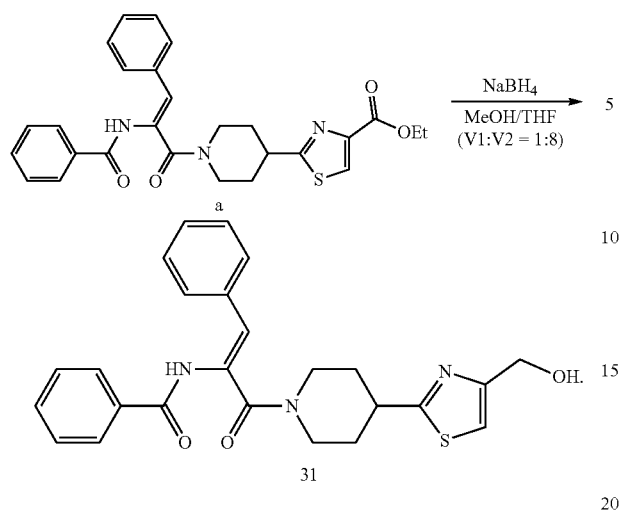

Synthesis Example 5: Preparation of Compound 31

Compound 31: (Z)—N-[1-[[[4-[2-(4-thiazolylacetate)]]-1-piperidinyl]carbonyl]-2-phenylvinyl]benzamide The compound a (1.15 g) was added to a 100 ml round-bottomed flask, then 40 mL of dried THF and 5 mL of dried MeOH were added, 18.79 mmol $NaBH_4$ was added in batches for many times to obtain a mixture. The mixture was then stirred at room temperature for 5 h. After the reaction was completed, the mixture was dissolved in saturated ammonium chloride solution and extracted with ethyl acetate, the organic layers was washed with saturated brine, dried over anhydrous sodium sulfate, and the residue was purified by column chromatography on silica gel with a mixture of petroleum ether and ethyl acetate (1:3-0:1, v/v) to give 0.90 g (yield 85.7%) of the white solid IV as the compound 31, (Z)—N-[1-[[[4-[2-(4-thiazolylacetate)]]-1-piperidinyl]carbonyl]-2-phenylvinyl]benzamide, the structural parameters were shown in Table 1.

The general structure formula of the aryl containing α-amino acrylic derivative IC was as follow:

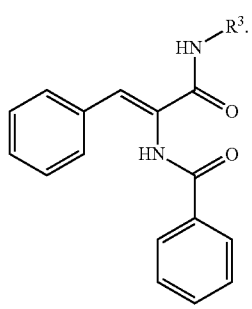

IC

The substituent of $R^3$ is as follows: methyl, methoxy, methyl (R)-2-propionate, methyl 1-propionate, methyl 1-butyrate, cyclopropyl, cyclohexyl, 4-bromobenzyl, 3-bromobenzyl, 2-bromobenzyl, benzyl, 4-methoxybenzyl, 4-fluorobenzyl, 4-chlorobenzyl, 4-trifluoromethylbenzyl, or 2-thienylbenzyl.

The synthesis method of the aryl containing α-amino acrylic derivative IC is as follow:

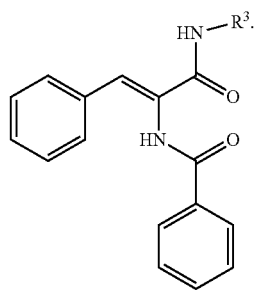

Synthesis Example 6: Preparation of Compound 36

Compound 36: (Z)—N-[1-[[1-(4-methylbutanoate)-amino]carbonyl]-2-phenylvinyl]benzamide When $R^3$ is methyl 1-butyrate-1-yl, the synthesis method of the compound IC is as follow:

To a 50 mL round-bottomed flask equipped, 0.20 mmol the compound a and 30 mL, DCM were added, and then 0.79 mmol PyBOP, 0.90 mmol $H_2N$—$R^3$, and 1.98 mmol DIPEA were added step by step to obtain a mixture, and the mixture was stirred at room temperature overnight. After completion, the mixture was washed with water, saturated ammonium chloride solution, and saturated brine in sequence, was dried with anhydrous $Na_2SO_4$ and purified by column chromatography with a mixed solution as eluent of petroleum ether and ethyl acetate with a volume ratio in a range of 5:1-1:1, to give the white solid IC that is the compound 36: (Z)—N-[1-[[1-(4-methylbutanoate)-amino]carbonyl]-2-phenylvinyl]benzamide with yield 92.6%. The structural properties were listed in Table 1.

The general structure formula of aryl and heterocyclic containing α-amino acrylic derivative ID is described as following structure:

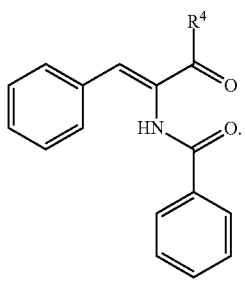

ID

When $R^4$ is $NR^3$, and $NR^3$ together constitutes a five- or six-membered heterocyclic ring selected from substituted 1 or 2 N atoms.

R[4] is preferably: (R)-(2-methoxycarbonyl)pyrrolidin-1-yl, 4-hydroxypiperidin-1-yl, morpholin-1-yl.

The synthesis method of aryl and heterocyclic containing α-amino acrylic derivative ID is as follows:

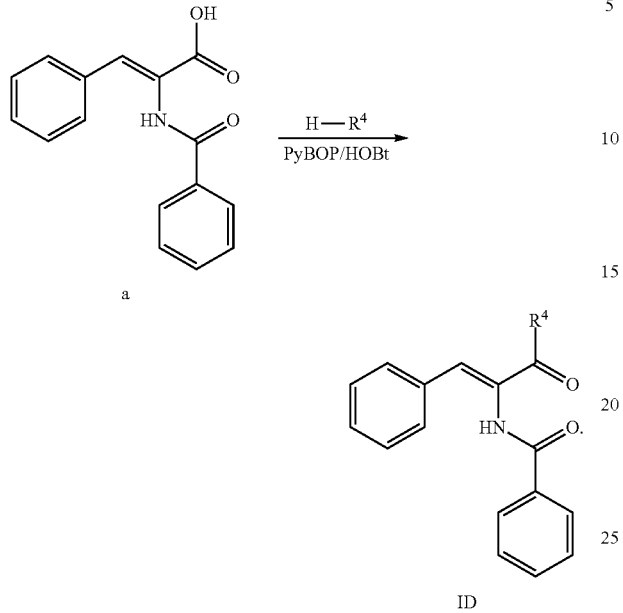

Synthesis Example 7: Preparation of Compound 37

Compound 37: (R,Z)—N-[1-[(2-Pyrrolidinemethyl)-carbonyl]-2-phenylvinyl]benzamide When R[3] is (R)-(2-methoxycarbonyl)pyrrol-1-yl, the synthesis method of the compound ID is as follow:

To a 50 mL round-bottomed flask, 0.20 mmol the compound a and 30 mL DCM were added, and then 0.79 mmol PyBOP, 0.90 mmol H—R[4], and 1.98 mmol DIPEA were added step by step to obtain a mixture and the mixture was stirred at room temperature overnight. After completion, the mixture was washed with water, saturated ammonium chloride solution, and saturated brine in sequence, was dried with anhydrous $Na_2SO_4$ and purified by column chromatography with a mixed solution as eluent of petroleum ether and ethyl acetate with a volume ratio in a range of 5:1-1:1, to give the white solid ID that is the compound 37: (R,Z)—N-[1-[(2-pyrrolidinemethyl)-carbonyl]-2-phenylvinyl]benzamide with yield 85.7%, and the structural properties were listed in Table 1.

The general structure formula of the thiazole-piperidine containing α-amino acrylic derivative IE is as follow:

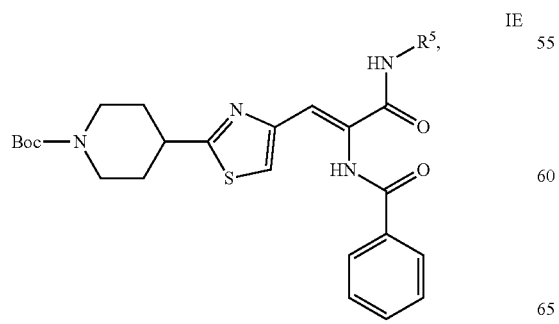

wherein: R[5] is methyl, methoxy, difluoroethyl, or 4-bromobenzyl.

The synthesis method of thiazole-piperidine containing α-amino acrylic derivative IE is as follows:

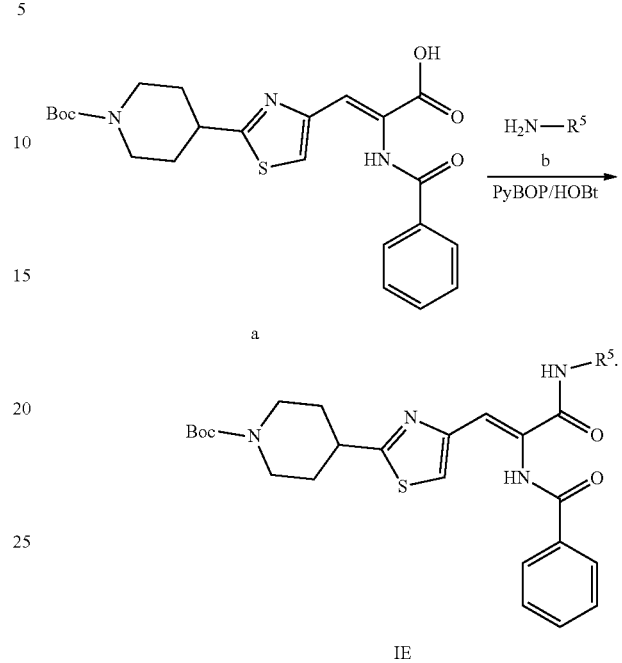

Synthesis Example 8: Preparation of Compound 43

Compound 43: (Z)—N-[1-[(2,2-difluoroethylamino)carbonyl]-2-[4-[2-[4-(1-tert-butoxycarbonylpiperidine)]thiazole]]vinyl]benzamide.

When R[3] is difluoroethyl, the synthesis method of the compound IE was as follow:

To a 50 mL round-bottomed flask, 0.30 mmol the compound a and 30 mL DCM were added, and then 0.69 mmol PyBOP, 0.79 mmol the compound b, 1.65 mmol DIPEA were added step by step to obtain a mixture, and the mixture was stirred at room temperature overnight. After completion, the mixture was washed with water, saturated ammonium chloride solution, and saturated brine in sequence, was dried with anhydrous $Na_2SO_4$ and purified by column chromatography with a mixed solution as eluent of petroleum ether and ethyl acetate with a volume ratio of 5:1-1:1, to give the compound IE that is the compound 43: (Z)—N-[1-[(2,2-difluoroethylamino)carbonyl]-2-[4-[2-[4-(1-tert-butoxycarbonylpiperidine)]thiazole]]vinyl]benzamide with yield 67.6%, and the structural properties were listed in Table 1.

The general structure formula of the α-amino acrylic derivative substituted with piperidine IF is as follow:

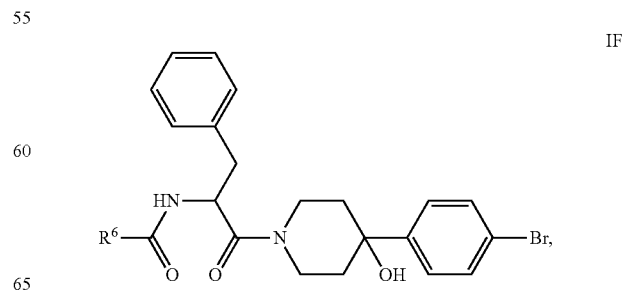

Wherein, R[6] is cyclopropyl or cyclohexyl.

The synthesis method of the α-amino acrylic derivative substituted with piperidine IF is as follows:

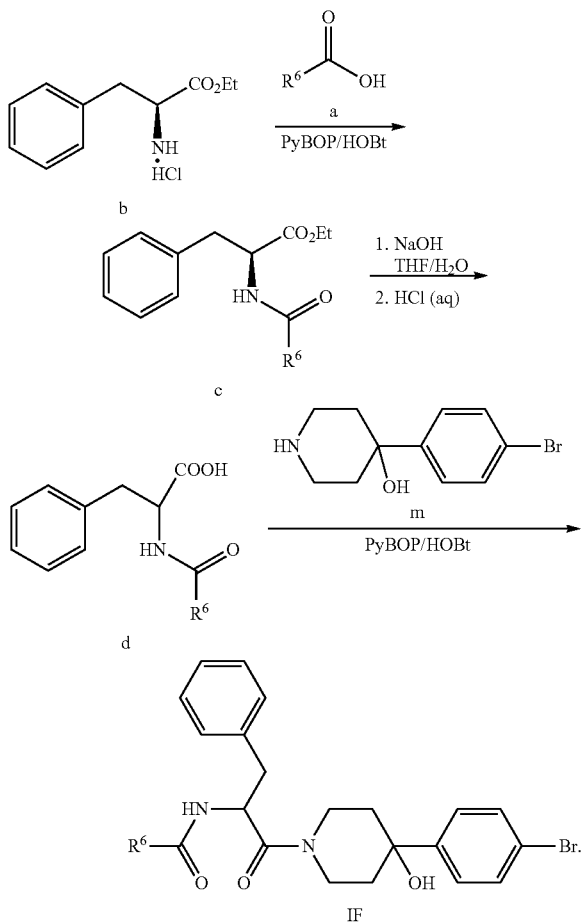

Synthesis Example 9: Preparation of Compound 50

Compound 50: N-[1-[[4-(4-bromophenyl)-4-hydroxy]-1-piperidinyl]carbonyl]-2-phenylethyl]cyclohexylcarboxamide When $R^1$ is a cyclohexyl, the compound IF is the compound 50, and the synthesis method was shown as follow:

To a 100 mL round-bottomed flask, 0.50 mmol the compound a and 60 mL DCM were added, and then 4.10 mmol PyBOP, 4.68 mmol the compound b, and 13.65 mmol DIPEA were added step by step to obtain a mixture, and the mixture was stirred at room temperature overnight. After completion, the mixture was washed with water, saturated ammonium chloride solution, and saturated brine in sequence, was dried with anhydrous $Na_2SO_4$ and purified by column chromatography with a mixed solution as eluent of petroleum ether and ethyl acetate with a volume ratio of 7:1-4:1, to give a white solid which is the compound C with yield 68.1%.

Then, the obtained compound c was directly added to 15 mL MeOH, and then 5.32 mmol of sodium hydroxide aqueous solution (15 mL) was added to obtain a mixture, and the mixture was heated under reflux for 3 hours. After cooling to room temperature, the solvent MeOH was distillated, and a small amount of water was added and transferred to a beaker. The pH was adjusted to 1-2 with concentrated hydrochloric acid solution, and a large amount of white solid was precipitated, filtered, and dried under infrared light to obtain a white solid that is the compound d 0.55 g (yield: 75.3%).

To a 50 mL round-bottomed flask, 0.20 g the compound d and 10 mL DMF were added, and then 0.77 mmol PyBOP, 0.88 mmol m, and 1.83 mmol DIPEA were added step by step to obtain a mixture, and the mixture was stirred at room temperature overnight, and then was transferred to a beaker, and 80 mL brine was added. A large amount of white solid was precipitated, and then filtered. The solid was dissolved in ethyl acetate, dried over anhydrous sodium sulfate, and the mixture was purified by column chromatography with a mixed solution as eluent of petroleum ether and ethyl acetate with a volume ratio in a range of 7:1-2:1 to give the final product IF, that is the compound 50: N-[1-[[4-(4-bromophenyl)-4-hydroxy]-1-piperidinyl]carbonyl]-2-phenylethyl]cyclohexylcarboxamide with yield 97.3%, and the structural properties are listed in Table 1.

The chemical structure of the substituted piperidine α-amino acrylic derivative was shown as follow:

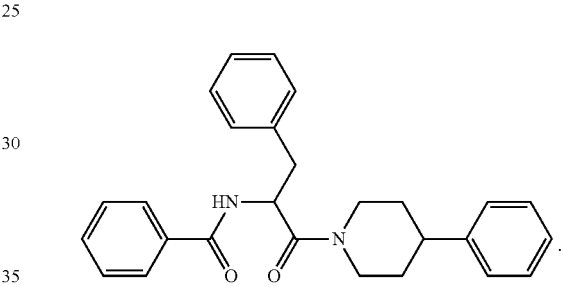

The synthesis method of the substituted piperidine α-amino acrylic derivative of the above formula was shown as bellow:

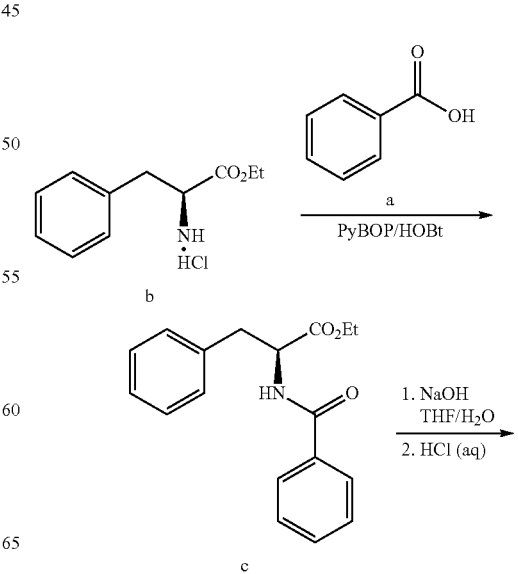

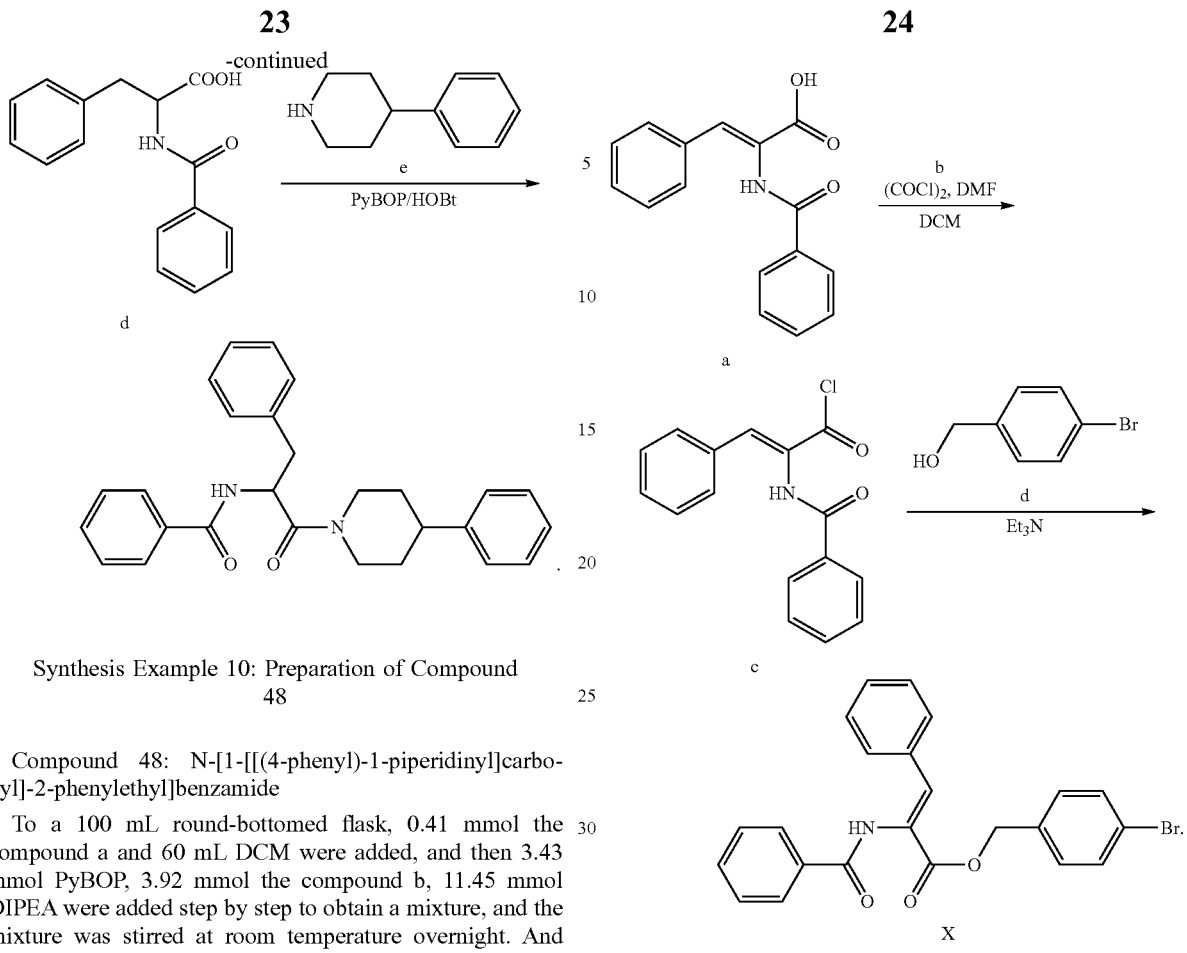

Synthesis Example 10: Preparation of Compound 48

Compound 48: N-[1-[[(4-phenyl)-1-piperidinyl]carbonyl]-2-phenylethyl]benzamide

To a 100 mL round-bottomed flask, 0.41 mmol the compound a and 60 mL DCM were added, and then 3.43 mmol PyBOP, 3.92 mmol the compound b, 11.45 mmol DIPEA were added step by step to obtain a mixture, and the mixture was stirred at room temperature overnight. And then, the mixture was washed with water, saturated ammonium chloride solution, and saturated brine in sequence; was dried with anhydrous $Na_2SO_4$ and purified by column chromatography with a mixed solution as eluent of petroleum ether and ethyl acetate with a volume in range of 7:1-4:1, to give a white solid that is the compound c 0.90 g (yield: 92.8%).

Then, the obtained 0.70 g compound c is added to 30 mL MeOH, and then 30 mL 4.94 mmol of sodium hydroxide aqueous solution was added to obtain a mixture, and the mixture was heated under reflux for 3 hours. After cooling to room temperature, the solvent was evaporated in vacuum, and a small amount of water was added and transferred to a beaker. The pH was adjusted to 1-2 with concentrated hydrochloric acid solution, and a large amount of white solid was precipitated, filtered, and dried under infrared light to obtain a white solid that is the compound d 0.54 g (yield: 80.6%).

To a 50 mL, round-bottomed flask, 0.19 g the compound d and 30 mL DCM were added, and then 0.75 mmol PyBOP, 0.85 mmol the compound e, and 1.78 mmol DIPEA were added step by step to obtain a mixture, and the mixture was stirred at room temperature overnight. And then, the mixture was washed with water, saturated ammonium chloride solution, and saturated brine in sequence, was dried with anhydrous $Na_2SO_4$ and purified by column chromatography with a mixed solution as eluent of petroleum ether and ethyl acetate with a volume ratio of 7:1-3:1, to obtain a white solid that is the compound 48 (yield: 96.8%), and the structural properties are listed in Table 1.

The chemical structure and synthetic route of the α-amino acrylate derivative X was shown as follow:

Synthesis Example 11: Preparation of Compound 61

Compound 61: N-[(1Z)-2-phenyl-1-[(4-bromophenylmethoxy)carbonyl]vinyl]benzamide 1.47 g of the compound a and two drops of DMF were added to dried dichloromethane, and then under an nitrogen atmosphere, 6.10 mmol of the compound b was added drop by drop in ice bath, and then the ice bath is removed, and a mixture is obtained. The mixture was gradually warmed to room temperature and stirred at room temperature for 2 h. After completion, 3.70 mmol d and 2.75 mmol of triethylamine were added to the mixture. The mixture was stirred at room temperature, and monitored by TLC. After the reaction was completed, the mixture was washed with water, saturated ammonium chloride solution and saturated brine, and dried with sodium sulfate, column chromatography, eluent:petroleum ether: ethyl acetate=20:1-10:1, to give the final product compound 61 with yield 47.9%, and the structural properties were listed in Table 1.

The representative compounds of the present invention were shown in Table 2.

(2) Biological Activity of α-Amino Acrylic Derivative I of the Present Invention (2-1) The Anti-Tobacco Mosaic Virus Activity of the α-Amino Acrylic Derivative I of the Present Invention is Determined as Follows:

The screening method for the anti-tobacco mosaic virus (TMV) activity of the α-amino acrylic derivative I of the invention is as follows:

Treatment Mode:

Screening method for the anti-TMV curative activity of α-amino acrylic derivative I: using live friction inoculation method, the ordinary tobacco seedlings with the same seedling age were rubbed with TMV on the first day, and brushed the medicine on the third day. Treatment method: drug test compound solution 2 to 3 times, 10 ml each time, the determination concentration is 100 μg/mL, check the incidence on the seventh day. The comprehensive number of lesions was calculated by the following formula to calculate the antiviral effect of the test compound on TMV. Each treatment was repeated 3 times. Blank control and standard drug control are selected separately as water and ribavirin, BTH, TDL, ningnanmycin. Lead compounds of the present invention: compound 76 and compounds similar in structure to the compounds of the present invention: compound 24, compound 25, compound 32, compound 38, compound 39, compound 40, compound 45, compound 53; Calculate the treatment effect based on the inspection results after 7 days:

$$R = \frac{CK - I}{CK} \times 100,$$

wherein: R is the antiviral effect of the test compound on TMV, unit: %; CK is the average number of blight spots on the leaves of the control water, unit: piece; I is the average number of blight spots on the leaves after treatment with the test compound, unit: piece.

Protection Mode:

Screening method for the anti-TMV protective activity of α-amino acrylic derivative I: using live friction inoculation method, the ordinary tobacco seedlings with the same seedling age were brushed the medicine on the first day, and TMV was rubbed with emery abrasive on the third day. Treatment method: drug test compound solution 2 to 3 times, 10 ml each time, the determination concentration is 100 μg/mL, check the incidence on the seventh day. The comprehensive number of lesions was calculated by the following formula to calculate the antiviral effect of the test compound on TMV. Each treatment was repeated 3 times. Blank control and standard drug control are selected separately as water and ribavirin, BTH, TDL, ningnanmycin. Lead compounds of the present invention: compound 76 and compounds similar in structure to the compounds of the present invention: compound 24, compound 25, compound 32, compound 38, compound 39, compound 40, compound 45, compound 53; Calculate the treatment effect based on the inspection results after 7 days:

$$R = \frac{CK - I}{CK} \times 100,$$

wherein: R is the antiviral effect of the test compound on TMV, unit: %; CK is the average number of blight spots on the leaves of the control water, unit: piece; I is the average number of blight spots on the leaves after treatment with the test compound, unit: piece.

Inactivation Mode:

Screening method for the anti-TMV inactivation activity of α-amino acrylic derivative I: using live friction inoculation method, first, the new compound and the target compound of the present invention are mixed with TMV virus for about 5 hours, and ordinary tobacco seedlings with the same seedling age are selected. Then 10 ml of the target compound and TMV virus mixture were rubbed with diamond to inoculate 3 tobacco leaves. The concentration of the test compound in the mixture is 100 μg/mL, check the incidence on the seventh day. The comprehensive number of lesions was calculated by the following formula to calculate the antiviral effect of the test compound on TMV. Each treatment was repeated 3 times. Blank control and standard drug control are selected separately as water and ribavirin, BTH, TDL, ningnanmycin. Lead compounds of the present invention: compound 76 and compounds similar in structure to the compounds of the present invention: compound 24, compound 25, compound 32, compound 38, compound 39, compound 40, compound 45, compound 53; Calculate the treatment effect based on the inspection results after 7 days:

$$R = \frac{CK - I}{CK} \times 100,$$

wherein: R is the antiviral effect of the test compound on TMV, unit: %; CK is the average number of blight spots on the leaves of the control water, unit: piece; I is the average number of blight spots on the leaves after treatment with the test compound, unit: piece.

Induction Mode:

Screening method for the anti-TMV inducing activity of α-amino acrylic derivative I: the living body was measured by the leaf dipping method. The ordinary tobacco seedlings with the same seedling age were brushed with drugs on the first day, on the third day, and on the fifth day. On the seventh day, the virus was added to the new long leaves. Treatment method: drug test compound solution 2 to 3 times, 10 ml each time, the determination concentration is 100 μg/mL, check the incidence on the seventh day. The comprehensive number of lesions was calculated by the following formula to calculate the antiviral effect of the test compound on TMV. Each treatment was repeated 3 times. Blank control and standard drug control are selected separately as water and ribavirin, BTH, TDL, ningnanmycin. Lead compounds of the present invention: compound 76 and compounds similar in structure to the compounds of the present invention: compound 24, compound 25, compound 32, compound 38, compound 39, compound 40, compound 45, compound 53; Calculate the treatment effect based on the inspection results after 7 days:

$$R = \frac{CK - I}{CK} \times 100,$$

wherein: R is the antiviral effect of the test compound on TMV, unit: %; CK is the average number of blight spots on the leaves of the control water, unit: piece; I is the average number of blight spots on the leaves after treatment with the test compound, unit: piece.

(2-2) Determination of Fungicide Activities of the α-Amino Acrylic Derivative I of the Present Invention:

The bactericidal or fungicidal activity of the α-amino acrylic derivative I of the present invention is determined by a fungi growth rate method. The specific steps are: Weigh 1.8 mg of the sample and dissolve it in an appropriate amount of dimethylformamide, and then dilute it to 500 μg/mL with a certain amount of Tween 20 aqueous solution as an emulsifier. Put 1 ml of the test compound under sterile conditions into the petri dish, and then add 9 ml of PDA culture medium, shake it to make 50 μg/ml drug-containing plate, and use a plate with 1 ml of sterilized water as a blank control. Use a hole punch with a diameter of 4 mm to cut the mycelium disc along the outer edge of the mycelium, move it to the medicine-containing plate, and place it in an equilateral triangle. Repeat each treatment 3 times. Place the petri dish in a 24±1 degree Celsius incubator. After the diameter of the control colony has expanded to 2-3 cm, investigate the expanded diameter of each treated bacteria dish and find the average value. Calculate the relative bacteriostatic rate compared with the blank control. The test bacteria are the species of most typical plant pathogens that actually occur in the field in China's agricultural production. Their codes and names are as follows: AS: *Alternaria solani*, BC: *Botrytis cinerea*, CA: *Cercospora arachidicola*, GZ: wheat *Gibberella zeae*, PI: *Phytophthora infestans* (Mont) de Bary, PP: *Physalospora piricola*, PS: *Pellicularia sasakii*, RC: *Rhizoctonia cerealis*, SS: *Sclerotinia sclerotiorum*. A compound with an activity of about 100% was subjected to a precise virulence measurement and its $EC_{50}$ value was calculated.

In the present invention, the structure of the α-amino acrylic derivative I is pilot-optimized, a novel compound is prepared, the preparation method of the above compound is studied, and it is unexpectedly found that the α-amino acrylic derivative I has fungicide activity.

Biological Activity Example 1

Anti-TMV Activity of the α-Amino Acrylic Derivative I of the Present Invention:

Anti-TMV treatment mode determination results: the results of anti-TMV treatment mode determination are shown in Table 3. Table 3 shows:

The curative activities of the positive control drugs were: ribavirin (28%) had no curative effect, BTH (50.00%), TDL (49%) and ningnanmycin (63%) showed some curative activity, among them, ningnanmycin has the highest activity.

The lead compound 76, which is structurally similar to the target compound of the present invention, has almost no curative activity. Control compound: compounds similar in structure to the present invention, such as compound 24, compound 32, compound 38, compound 39, compound 40, have almost no curative activity, and compound 45 (30%) exhibits lower curative activity against the compound, compound 25 (55%) and compound 53 (55%) exhibited moderate levels of resistance to curative activity.

While the target compound designed and synthesized by the present invention: compound 11 (78%), compound 44 (83%), and compound 59 (80%) exhibited extremely high curative activity, the curative activity was 10% higher than that of the positive control agent with the highest activity. Its curative activity is more than 20% higher than that of the structurally similar compounds 25 and 53 of the present invention. Thus, the overall effect of these compounds due to changes in substituents has shown unexpectedly outstanding curative effects. compound 1 (53%), compound 2 (50%), compound 3 (59%), compound 9 (50%), compound 12 (56%), compound 47 (56%), compound 57 (52%) showed Similar curative activity as structural analog compound 25 and compound 53. Surprisingly, compound 64 (58%) and compound 67 (52%), which were synthesized in the present invention, also exhibited moderate curative activity.

Anti-TMV inactivation mode measurement results: the results of anti-TMV inactivation mode measurement were shown in Table 3. Table 3 shows:

The inactivating activities of the positive control drugs were: ribavirin (81%), BTH (63%), TDL (55%) and ning- nanmycin (58%) showed good inactivation activity. Among them, ribavirin activity is the best.

The lead compound 76 (29%) which is structurally similar to the target compound of the present invention exhibited lower inactivation activity, and the control compound: structurally similar compound 24, compound 38, compound 39, and compound 40 had almost no inactivation activity. Structurally similar compounds 25 (31%) and 32 (25%) and 45 (22%) showed lower inactivation activity, and structurally similar compounds 53 (58%) showed moderate resistance to inactivation.

In the target compound designed and synthesized by the present invention, compound 1 (83%), compound 2 (81%), and compound 62 (86%) exhibit excellent inactivation activity. Its inactivation activity is more than 50% higher than the activity of a similar compound of the present invention. Compound 10 (62%), compound 11 (71%), compound 13 (69%), compound 46 (64%), compound 51 (69%), compound 57 (61%) exhibited high inactivation activity. Compound 10 (62%), compound 11 (71%), compound 13 (69%), compound 46 (64%), compound 51 (69%), compound 57 (61%) exhibited high inactivation activity. Compound 6 (50%), compound 21 (58%), compound 22 (58%), compound 55 (59%), compound 56 (58%), compound 60 (53%), compound 63 (50%) exhibited moderate inactivation activity. Its inactivation activity is more than 20% higher than the activity of a similar compound of the present invention. The target molecule obtained by the above-mentioned compound as a whole molecular design exhibits an extremely high inactivation activity unexpectedly with the lead compound and the structural analog, and has outstanding effects and remarkable technical progress. It is very surprising that the intermediate compound 71 (67%) designed and synthesized by the present invention exhibits high inactivation activity, intermediate compound 67 (57%) and compound 73 (59%) and compound 75 (53%) exhibits high inactivation activity.

Anti-TMV Protection Mode Measurement Results: The Anti-TMV Protection Mode Measurement Results are Shown in Table 3, Table 3 Shows:

The protective activities of the positive control drugs were: ribavirin (58%), BTH (76%), TDL (32%), and ningnanmycin (71%). Ribavirin and BTH and ningnanmycin have good protective activity, and TDL has weak protective activity.

The lead compound 76 (38%) structurally similar to the target compound of the present invention exhibited lower protective activity, and the control compound: structurally similar compound 40 had almost no protective activity, and compound 24 (36%), compound 25 (46%), compound 38 (38%), compound 39 (10%), compound 53 (33%) showed lower protective activity, and compound 32 (58%) and compound 45 (54%) showed better antiviral protective activity.

In the target compound designed and synthesized by the present invention: compound 9 (60%), compound 3 (51%), compound 7 (50%), compound 16 (57%), compound 20 (52%), compound 23 (59%) compound 45 (54%) and compound 63 (53%) showed higher protective activity, comparable to the structurally similar compound 32. Fortunately, the intermediate compound 66 (83%) and compound 67 (78%) designed and synthesized by the present invention showed very good protective activity, and the compound 71 (53%) showed good protective activity.

Anti-TMV induction mode determination results: the results of anti-TMV induction mode measurement were shown in Table 3, and Table 3 shows:

The induction activities of the positive control drugs were: ribavirin (4%), BTH (96%), TDL (73%), and ningnanmycin (82%). The induction activities of BTH, TDL and ningnanmycin were very good, BTH is the highest.

The lead compound 76 (15%) which is structurally similar to the target compound of the present invention has almost no inducing activity, and the control compound: structurally similar compound 53 has almost no activity, and compound 24 (11%), compound 25 (37%), and compound 32 (10%), compound 38 (46%), compound 39 (34%), compound 40 (45%) showed lower inducing activity, and compound 45 (52%) showed moderate induction activity.

Among the target compounds designed and synthesized by the present invention, compound 2 (77%) showed excellent induction activity, and compound 14 (52%), compound 20 (53%), and compound 47 (53%) showed moderate inducing activity, it is very gratifying that the intermediate compound 75 (78%), compound 74 (63%) designed and synthesized by the present invention also exhibited excellent inducing activity, and compound 64 (51%) showed moderate inducing activity.

In addition to the above-mentioned tobacco mosaic virus disease, the compounds of the present invention are against rice dwarf disease, yellow dwarf disease, stripe leaf blight, tomato fern leaf virus disease, pepper mosaic virus disease, tobacco vein necrosis virus disease, corn dwarf leaf disease, cauliflower mosaic virus, citrus virus disease, mustard leaf virus, mustard ring spot virus also have good direct antiviral activity and induce antiviral activity.

Intermediate 77 is a 4-methyl-1,2,3-thiadiazole anti-hepatitis B virus compound (CN101260091) reported in the literature. The present invention finds that it has no curative and inactivation activity against TMV, and has moderate protection and the inducing activities were 40% and 44% respectively, and the corresponding 5-methyl derivative 78 had good inactivation activity and good inducing activity 47% and 68% respectively. The activity of the compound 78 was higher than that reported in the literature by more than 20% due to a change in the substituent. The target compound 27 derived from the intermediate 77 has no curative activity, and the target compound 28 synthesized from the intermediate 78 synthesized in the present invention has an induction activity higher than that of the compound 27 at 40%. The inactivation activity of the target compound 27 derived from the intermediate 77 was 34%. On the other hand, the target compound 28 synthesized by the intermediate 78 synthesized in the present invention had no inactivation activity, and the two compounds of the target compounds, compounds 27 and 28, had no inducing activity, and their protective activities were basically the same, 37% and 36%, respectively.

Biological Activity Example 2

The Fungicidal Activity of the α-Amino Acrylic Derivative I of the Present Invention is Measured:

The code and name of the common phytopathogenic fungi tested in the present invention are as follows: AS: *Alternaria solani*, BC: *Botrytis cinerea*, CA: *Cercospora arachidicola*, GZ: wheat *Gibberella zeae*, PI: *Phytophthora infestans* (Mont.) de Bary, PP: *Physalospora piricola*, PS: *Pellicularia sasakii*, RC: *Rhizoctonia cerealis*, SS: *Sclerotinia sclerotiorum*. These strains are well represented and represent the species of most pathogens that occur in the field in agricultural production. The results of the growth inhibition rate of the α-amino acrylic derivative I of the present invention are shown in Table 4. Table 4 shows that at 50 ng/mL, all the compounds synthesized by the present invention have different degrees of bactericidal activity.

For AS: *Alternaria solani*, the azoxystrobin has a fungicidal activity of 79%. The fungicidal activity of the lead compound 76 having a structure similar to the target compound of the present invention is 14%. The fungicidal activity of comparative compound 24, compound 25, compound 32, compound 38, compound 39, compound 45, compound 40, and compound 53 which are closest to the structure of the present invention was less than 30%. The target compound 18, the compound 42 of the present invention exhibited good bactericidal activities of 43%, 63%, respectively.

For CA: *Cercospora arachidicola*, the assay results showed that the fungicidal activity of azoxystrobin was 81%. The fungicidal activity of the lead compound 76 which is structurally similar to the target compound of the present invention was 24%. The control compound closest to the structure of the present invention: compound 24, compound 25, compound 32, compound 38, compound 39, compound 45, compound 40, compound 53 were all less than 25%. The target compound 6 (49%), the compound 16 (55%), and the compound 42 (44%) of the present invention exhibited moderate fungicidal activity.

For GZ: wheat *Gibberella zeae*, the activity test results showed that the fungicidal activity of azoxystrobin was 100%, and the fungicidal activity of the lead compound 76 having a structure similar to the target compound of the present invention was 43%. The control compound closest to the structure of the present invention: compound 24, compound 25, compound 32, compound 38, compound 39, compound 45, compound 40, and compound 53 all had a 45% lower fungicidal activity. The object compound 7 (71%), the compound 26 (77%) and the compound 71 (86%) of the present invention exhibited excellent fungicidal activity.

For PP: *Physalospora piricola*, the inhibitory activity showed that the azoxystrobin had an fungicidal activity of 81%, and the lead compound 76 having a structure similar to the target compound of the present invention had an fungicidal activity of 15%. The control compound closest to the structure of the present invention: compound 24, compound 25, compound 32, compound 38, compound 39, compound 45, compound 40, compound 53 were all 20% less active. The target compound 42 of the present invention was 44%, and the target compound 6 had the highest fungicidal activity of 49%, and exhibited moderate fungicidal activity.

For BC: *Botrytis cinerea*, the activity test showed that the azoxystrobin had a fungicidal activity of 78%, and the lead compound 76 having a structure similar to the target compound of the present invention had an fungicidal activity of 18%. The control compound closest to the structure of the present invention: compound 24, compound 25, compound 32, compound 38, compound 39, compound 40, compound 53 had no fungicidal activity of more than 20%. The target compound 6 (48%), the compound 41 (52%), the compound 42 (53%), and the compound 74 (41%) of the present invention exhibited moderate fungicidal activity.

For SS (*Sclerotinia sclerotiorum*), azoxystrobin showed fungicidal activity of 100%, and the control compound 76 (50%) closest to the structure of the present invention exhibited moderate activity. The control compound closest to the structure of the present invention, compound 25 showed fungicidal activity of 100% and exhibits excellent activity; Compound 24 (67%), compound 32 (80%), compound 38 (77%), compound 39 (67%), compound 53 (75%)

showed excellent activity, and compound 40 (56%) showed moderate activity, while the compound 45 (38%) showed weak activity. The target compound 2, compound 9, compound 11, compound 12, compound 22 and compound 56 of the present invention showed excellent activities of 100%; The activities of compound 1, compound 10, compound 14, compound 30, compound 47, compound 73, and compound 74 were between 80% and 95%. The activities of compound 3, compound 5, compound 21, compound 26, compound 28, compound 54, compound 55, compound 59, compound 68, and compound 69 all exhibited moderate activity between 60% and 80%.

For RC (*Rhizoctonia cerealis*), the fungicidal activity of azoxystrobin was 67%, and the fungicidal activity of lead compound 76, which is structurally similar with the target compounds of the present invention, was 15%. The closest control compound to the structure of the present invention, Compound 25 (36%) exhibited moderate fungicidal activity. Compound 24, compound 32, compound 38, compound 39, compound 45, compound 40, and compound 53 were all showed weak activities, less than 20%; Compound 28 (62%) of the present invention exhibited good fungicidal activity. Compound 42 (45%), compound 43 (38%), and compound 74 (44%) of the present invention exhibited moderate fungicidal activity.

For PS (*Pellicularia sasakii*), the fungicidal activity of azoxystrobin was 92%, and the fungicidal activity of lead compound 76, which is structurally similar with the target compound of the present invention, was 14%. The closest control compound to the structure of the present invention, compound 24, compound 25, compound 32, compound 38, compound 39, compound 45, compound 40, and compound 53 were all showed weak activities, less than 30%. Target compound 6 (54%) and compound 42 (43%) of the present invention exhibited moderate fungicidal activity.

For PI (*Phytophthora infestans* (Mont) de Bary), the fungicidal activity of azoxystrobin was 91%, and the fungicidal activity of lead compound 76, which is structurally similar with the target compounds of the present invention, was 24%. The closest control compounds to the structure of the present invention, compound 24, compound 25, compound 32, compound 38, compound 39, compound 45, compound 40, and compound 53 all showed activities less than 25%. Target compound 6 (50%), compound 16 (33%), compound 42 (44%), compound 43 (38%) and compound 74 (40%) of the present invention exhibited moderate fungicidal activity.

The intermediate 77 was a 4-methyl-1,2,3-thiadiazole anti-hepatitis B virus compound reported in the literature (CN101260091). The present invention showed that intermediate 77 exhibited weak fungicidal activity, only with moderate activity (47%) against *Sclerotinia sclerotiorum*. The corresponding 5-methyl derivative 78 showed the fungicidal activities against AS (*Alternaria solani*), GZ (*Gibberella zeae*), BC (*Botrytis cinerea*) and PI (*Phytophthora infestans* (Mont.) de Bary) with 29%, 57%, 26% and 26%, respectively. The change of the substituent resulted in that the activities of the compound 78 against the above four fungi were higher than that reported compound 77 in the literature over 10%, and the activities against the other fungi were comparable, less than 25%. The target compound 27 derived from the reported intermediate 77 and the target compound 28 synthesized from the intermediate 78 in the present invention, showed comparable fungicidal activities (about 20%) against BC (*Botrytis cinerea*), PS (*Pellicularia sasakii*) and PI (*Phytophthora infestans* (Mont.) de Bary). The fungicidal activities of the target compound 28 synthesized from the intermediate 78 in the present invention against the other 6 tested fungi were higher than the target compound 27 derived from the reported intermediate 77 over 10%, even over 39% (as showed in Table 4). Therefore, the change in the position of a substituent will result in a dramatic change in biological activity.

The $EC_{90}$ value can well be used to compare the activity of the compounds. The results of $EC_{90}$ against *S. sclerotiorum* were showed in Table 5. The results of Table 5 indicated that the compounds of the present invention exhibited various degrees of fungicidal activity due to the change of the substituent.

The compound 25, the structure of which most similar with the compounds of the present invention and the best fungicidal activity ($EC_{90}$=221.17 μg/mL), was used as a control compound. The activity of the compound 2, compound 9, compound 18, compound 41 and compound 56 of the present invention showed lower activity than that of compound 25, which is the closest to the structure of the present invention; Among them, the activity of compound 2 was 0.39 times than that of the control compound 25 closest to the structure of the present invention; The activity of compound 9 was 0.81 times than that of control compound 25. The activity of compound 18 was 0.58 times than that of control compound 25. The activity of compound 41 was 0.59 times than that of control compound 25. The activity of compound 56 was 0.18 times than that of control compound 25.

The compound 6, compound 12, compound 13 and compound 22 of the present invention showed slightly higher activity than the control compound 25 closest to the structure of the present invention. Among them, the activity of compound 6 was 1.01 times than that of the control compound 25. The activity of compound 12 was 1.15 times than that of control compound 25. The activity of compound 13 was 1.13 times than that of control compound 25. The activity of compound 22 was 1.11 times than that of control compound 25.

The activity of compound 11, compound 42 and compound 43 of the present invention showed significantly higher than that of the control compound 25 closest to the structure of the present invention. Among them, the activity of the compound 11 was 1.73 times than that of the control compound 25. The activity of compound 42 was 1.43 times than that of control compound 25. The activity of compound 43 was 1.44 times than that of control compound 25.

The present invention also relates to a pesticide composition containing a α-amino acrylic derivative I as an active ingredient. The above-mentioned pesticide composition generally comprises 0.1 to 99% by weight, preferably 0.1 to 95% by weight of a compound of formula I, 99.9 to 1% by weight, preferably 99.8 to 5% by weight of a solid or liquid pesticide adjuvant, and 0 to 25% by weight, preferably 0.1 to 25% by weight of a surfactant. For the pesticide composition containing the α-amino acrylic derivative I as an active ingredient, the suitable dosage form was selected from the group consisting of a seed treatment emulsion, an aqueous emulsion, a large granule, a microemulsion, a water-soluble granule, a soluble concentrate, and a water-dispersible granule. Poison valley, aerosol, block bait, slow-release block, concentrated poison bait, capsule granules, microcapsule suspension, dry seed powder, emulsifiable concentrate, wettable powder electrostatic spray, water-in-oil emulsion, oil-in-water emulsions, aerosol cans, fine granules, aerosol candles, aerosol cans, aerosol sticks, seed treatment suspensions, aerosol tablets, aerosol pills, granular poisonous baits, thermal aerosols, paints, fine particles, oil suspensions, oil-dispersible powder, Flake bait, thick glue, pouring agent, seed coating agent, spreading agent, suspension emulsion, film-forming oil agent, soluble powder, water soluble powder for seed treatment, ultra-low capacity suspension agent, tracking powder, ultra-low capacity liquid agent, or a water-dispersible powder for wet dressing.

Although commercial product formulations are preferably formulated as concentrates, end users typically use dilute formulations.

The α-amino acrylic derivative I of the present invention is in combination with a commercial insecticide for controlling plant pests in agriculture, forestry and horticulture.

The α-amino acrylic derivative I of the present invention is in combination with agriculturally acceptable auxiliaries and one or more of the following commercial insecticides for preparing compound insecticides.

The commercial insecticide was at least one member selected from the group consisting of chlorpyrifos, diazepam, acetamiprid, methylaminoavermectin, mibemycin, avermectin, spinosyn, fenvalerate, esfenvalerate, cypermethrin, beta-cypermethrin, cyhalothrin, deltamethrin, fenpropathrin, cyfluthrin, permethrin, permethrin, S-Bioallethrin, bifenthrin, permethrin, etofenprox, flumethrin, fluvalinate, imidacloprid, acetamiprid, nitenpyram, chlorothiazoline, thiacloprid, thiamethoxam, clothianidin, dinotefuran, clonidine, dinotefuran, diflubenzuron, chlorfenuron, flubendicarb, diflubenzuron, flubenzuron, fluﬂudicarb, acetamiprid, fenflubenzuron, chlorflubenzuron, fluflubenzuron, Noviflumuron (CAS No. 121451-02-3), flufenazone, novaluron, fluoxuron, Bay sir 6874 {1-[(3,5-dichloro-4) 4-nitrophenoxyphenyl3-3-(2-chlorobenzene)-urea], Bay SIR-8514 {1-(4-trifluoromethoxyphenyl)-3-(2-chlorobenzene)-urea}, pyraclostrobin, bistrifluron, fufenozide, tebufenozide, halofenozide, methoxyfenozide, chromafenozide, dimethoate, omethoate, dichlorvos, methamidophos, triazophos, quintiophos, pyridaphenthion, isazophos, isoprocarb, tricarnam, pirimicarb, tsumacide, isoprocarb, carbendazim, fenobucarb, N-methyl 2,3-dimethylphenyl carbamate, carbaryl, benfuracarb, carbosulfan, fenitrothion, bromopropylate, hexythiazox, fenpyroximate, pyridaben, tetrabenazine, propargite, diafenthiuron, benfuracarb, pymetrozine, spirodiclofen, spiromesifen, spirotetramat, butenafipronil, azacyclotin, buprofezin, ethoprophos, Fipronil, monosultap, bisultap, chlorantraniliprole, flubendiamide, tetraniliprole, cyantraniliprole, tolfenpyrad, tebufenpyrad, chlorfenapyr, pyrazinone, etoxazole, tebufenpyrad, pyridone, pyriproxyfen, and emamectin;

the mass percentage of the α-amino acrylic derivative I of the present invention in the compound insecticide is 1%-90%, and the mass ratio of the α-amino acrylic derivatives I to the above described commercial insecticides was from 1%:99% to 99%:1%;

the formulation suitable for the compound insecticide was seed treatment emulsion, water emulsion, large granule, microemulsion, water-soluble granule, soluble concentrate, water-dispersible granule, poisonous valley, aerosol, and block poison bait., Slow-release blocks, concentrated poison bait, capsule granules, microcapsule suspensions, dry seed powders, emulsifiable concentrates, wettable powders, electrostatic sprays, water-in-oil emulsions, oil-in-water emulsions, smoke cans, fine granules, smoke candles, smoke tube, smoke stick, seed treatment suspension agent, smoke tablet, smoke pill, granular poison bait, hot aerosol, medicinal paint, fine particles, oil suspension, oil dispersible powder, flake poison bait, thick glue, splash pouring Agent, seed coating agent, spreading agent, suspension emulsion, film-forming oil agent, soluble powder, seed treatment water-soluble powder, ultra-low-capacity suspending agent, tracking powder, ultra-low-volume liquid agent, or wet-seed water-dispersible powder;

the plant suitable for the compound insecticide was rice, wheat, barley, oats, corn, sorghum, sweet potato, potato, cassava, soybean, pea, broad bean, pea, mung bean, adzuki bean, cotton, silkworm, peanut, rape, Sesame, sunflower, beet, sugar cane, coffee, cocoa, *ginseng*, fritillary, rubber, coconut, oil palm, sisal, tobacco, tomato, pepper, radish, cucumber, cabbage, celery, mustard, shallot, garlic, watermelon, melon, cantaloupe, *papaya*, apple, citrus, peach tree, tea, wild vegetables, bamboo shoots, hops, pepper, banana, *papaya*, orchid, or bonsai;

insect pests controlled by the compound insecticide were *asiatic migratory locusts, gastrimargus marmoratus, Oxya chinensis Thunberg, Patanga japonca Bolivar, Gryllotlp unispin Sussure, Gryllotalpa orientalis Burmeister, Chloethrips oryzae, Thrips alliorum* (Priesner), *Hercinothrips femoralis, Haplothnps aculeatus, Haplothrips tritici, Trialeurodes vaporariorum* (Westwood), *Bemisia tabaci, Nephotettix bipunctatus* (Fabricius), *Cicadella viridis, Empoasca biguttula* (Ishida), *Lycorma delicatula, Nilaparvata lugens* (Stal), *Sogatella furcifera* (Horváth), *Laodelphax striatellus* (Fallén), *Perkinsiella saccharicida* (Kirkaldy), *Aphis gossypii* Glover, *Schizaphisgraminum, Sitobion avenae* (Fabricius), *Myzus persicae* (Sulzer), *Melanaphis sacchari, Lipaphis erysimi, Icerya purchasi, Pseudaulacaspis pentagona, Unaspis yanonensis, Quadraspidiotus pemiciosus* (Comstock), *Ericerus pela Chavannes, Ceroplastes rubens* (Maskell), *Didesmococcus koreanus Borchsenius, Stephanitis nashi* Esaki et Takeya, *Slephanitis typical* (Distant), *Lyctocoris, Oriu minuius Linnaeus, Ochrochira camelina, Leptocorisa acuta* (Thunberg), *Niphe elongata* (Dallas), *Scotinophara lurida* (Burmeister), *Nezara viridula* Linnaeus, *Lygocoris lucorum* (Meyer-Dur.), *Adelphocoris suturalis, Chrysopa septempunctata, Chrysopa formosa Brauer, Chrysoperla sinica* Tjeder, *Tineidae, Tinea pellionella, Cnidocampa flavescens* (Walker), *Setora postornata, Thosea sinensis, Sitotroga cerealella* Olivier, *Pectinophora gossypiella, Brachmia macroscopa, Plutella xylostella, Carposina niponensis* Walsingham, *Leguminivora glycinivorella* (Matsumura), *Carposina niponensis* Walsingham, *Spilonota lechriaspis, Hornona coffearia* (Meyrick), *Adoxophyes cyrtosema, Chilo suppressalis, Etiella zinckenella, Ostrinia nubilalis, Tryporyza incertulas, Hellula undalis* Fabricius, *Cnaphalocrocis medinalis, Proceras venosatum* (Walker), *Sylepta derogata* Fabricius, *Dichocrocis punctiferalis, Mythimna separata* (Walker), *Spodoptera litura* (Fabricius), *Naranga aenescens* Moore, *Anomis flava* (Fabricius), *Asparagus caterpillar, Sesamia inferens, Helicoverpa armigera, Earias cupreoviridis* Walker, *Agrotis ipsilon, Agrotis tokionis, Agrotis segetum, Porthesia similis* (Fueszly), *Lymantria dispar, Agrius convolvuli, Clanis bilineata, Parnara guttata* Bremer et Grey, *Pelopidas mathias* (Fabrieius), *Papilio xuthus, Papilio polytes, Pieris rapae, Pyrameis indica* Herbst, *Acraca issorie* (Hubner), *Epicauta gorhami, Calosoma auropunctatum, Cychrus convexus, Anisodactylus signatus, Pleonomus canaliculatus, Agriotes subrittatus* Motschulsky, *Trogoderma granarium, Attagenus minutus* Olivier, *Papilio xuthus, Lampra limbata* Gebler, *Tenebrio molitor, Tenebrio obscurus, Tribolium castaneum, Tribolium confusum, Verdigris aureus, Holotrichia parallela, Holotrichia oblita, Apriona germari, Anoplophora chinensis, Nadezhdilla cantori* (Hope), *Aromia bungii, Colaphellus bowringi* Baly, *Phaedon brassicae, Aulacophora femoralis, Phyllotreta striolata, Callosobruchus chinensis, Bruchus pisorum* (Linnaeus), *Bruchus rufimanus,*

*Sitophilus zeamais Motschusky, Sitophilus oryzae, Dolerus tritici, Hoplocampa pyricola, Pteroconnus generosus, Vulgichneumon leucaniae Uchida, Charops* bicolor (Szepligeri), *Campoletis chorideae Uchida, Xanthopimpla stemmator Thunberg,* mosquitoe, fly, horsefly, *Sitodiplosis mosellana Gehin, Contarinia tritici, Orseoia oryzae, Tetradacus citri, Bactrocera cucurbitae, Agromyza cinerascens Macquart, Liriomyza sativae, Melanagromyza sojae, Meromyza saltatrix, Hylemyia platura Meigen, Delia antigua Meigen, Phorbia brassicae, Exorista civilis, Lydella grisescens,* or *Mythimna seperata* (Walker).

The α-amino acrylic derivative I of the present invention is in combination with a commercial acaricide for controlling phytophagous mites in agriculture, forestry and horticulture.

The α-amino acrylic derivative I of the present invention is combined with any agriculturally acceptable pesticidal adjuvant agent and any one or more of the following commercial acaricides to prepare a compound acaricide and to be applied to control plant mites;

the commercial acaricide was azacyclotin, cyhexatin, fenbutatin, phoscyclotin, chlorfenvinphos, dimethylvinphos, crotoxyphos, dichlorvos, heptenophos, mevinphos, monocrotophos, orthodibrom, chlorpyrifos, pyrimithate, chloromethimthion, omethoate, dioxathion, ethionphos, malathion, methacrifos, fenthion, phoxim, silcsan, quinalphos, sulfotep, triazophos, aphid, vamidothion, isocarbophos, methamidophos, amiprophos, chloroimidophos, imithion, acrinathrin, bifenthrin, cyfluthrin, gamma cyhalothrin, fenpropathrin, flucythrinate, flumethrin, fluvalinate, broflu-thrinate, bifenazate, fenothiocarb, aldicarb, butocarboxim, oxamyl, thiocarboxime, thiofanox, benomyl, carbanolate, carbofuran, carbosulfan, tsumacide, promacyl, formetanate, semiamitraz, formetanate, amitraz, chlordimeform, benzyl benzoate, bromopropylate, cyflumetofen, acequinocyl, acarioquinone, fluoroaphis acari, fluorozorea, liuyangmycin, abamectin, doramectin, eprinomectin, ivermectin, seramin, moxidectin, pyrethrin, nicotine, matrine, azadirachtin, rotenone, tebufenpyrad, pyridaben, fenpyroximate, clofentezine, propargite, hexythiarizonaox, spirodiclofen, fluacrypyrim, chlorfenson, propargite, or pyridaben;

the mass percentage of the α-amino acrylic derivative I of the present invention in the mixed acaricide is 1%-90%, and the mass ratio of the α-amino acrylic derivatives I to the above described commercial acaricide was from 1%:99% to 99%:1%;

the formulation of the compound acaricide was wettable powder, microcapsule suspension, dispersible liquid preparation, dispersible solid preparation, seed treatment emulsion, water emulsion, large granule, microemulsion, oil suspension agent, pesticide package Coated seeds, water-soluble granules, soluble concentrates, water-dispersible granules, poison valley, aerosol, block poison bait, slow-release block, concentrated poison bait, capsule granules, dry seed powder, emulsifiable concentrate, wettable powder electrostatic spray, water-in-oil emulsion, oil-in-water emulsion, aerosol cans, fine granules, aerosol candles, aerosol cans, aerosol sticks, seed treatment suspensions, aerosol tablets, aerosol pills, granular poisonous bait, hot aerosols, medicines Lacquer, seed treatment liquid, granules, oil-dispersible powder, flake poison bait, thickening agent, pouring agent, spreading agent, suspension emulsion, film-forming oil agent, soluble powder, seed treatment water-soluble powder, ultra-low capacity suspending agent, tracking powder, ultra-low-volume liquid, or water-dispersible powder for wet dressing;

the plant suitable for the compound acaricide was rice, wheat, barley, oats, corn, sorghum, sweet potato, potato, cassava, soybean, pea, broad bean, pea, mung bean, adzuki bean, cotton, silkworm, peanut, rape, Sesame, sunflower, beet, sugar cane, coffee, cocoa, *ginseng,* fritillary, rubber, coconut, oil palm, sisal, tobacco, tomato, pepper, radish, cucumber, cabbage, celery, mustard, shallot, garlic, watermelon, melon, Cantaloupe, *papaya,* apple, citrus, peach tree, tea, wild vegetables, bamboo shoots, hops, pepper, banana, *papaya,* orchid, or bonsai;

The mites suitable for the compounds as acaricide were *Tetranychidae, Tenuipalpidae, Trichofurus furus, Eriophyidae, Tetranychus,* or *Eriophyidae,* which were worldwide agricultural spider mites, forestry spider mites, horticultural spider mites and health spider mites.

The α-amino acrylic derivative I of the present invention is in combination with a commercial fungicide for controlling plant diseases in agriculture, forestry and horticulture.

The α-amino acrylic derivative I of the present invention is in combination with any one or more of agriculturally acceptable auxiliaries and the following commercial fungicides for preparing a compound fungicide;

the commercial fungicide was benzothiadiazole, tiadinil, methiadinil, 4-methyl-1,2,3-thiadiazole-5-carboxylic acid, sodium 4-methyl-1,2,3-thiadiazole-5-carboxylate, ethyl 4-methyl-1,2,3-thiadiazole-5-carboxylate, ethyl 4-bromomethyl-1,2,3-thiadiazole-5-carboxylate, ethyl 4-iodomethyl-1, 2,3-thiadiazole-5-carboxylate, 4-bromomethyl-5-methyl-1, 2,3-thiadiazole, 4-iodomethyl-5-methyl-1,2,3-thiadiazole, ethyl 4,4-dibromomethyl-1,2,3-thiadiazole-5-carboxylate, 3,4-dichloroisothiazole-5-carboxylic acid, sodium 3,4-dichloroisothiazol-5-carboxylate, ethyl 3,4-dichloroisothiazol-5-carboxylate, DL-β-aminobutyric acid, isotianil, ribavirin, antofin, ningnanmycin, methionil, salicylic acid, cytosinpeptidemycin, dichloroisonicotinic acid, probenazole, cymoxanil, formex, ziram, mancozeb, aliette, methylthiocarb, chlorothalonil, fenaminosulf, procymidone, fenpropidin, thiophanate methyl, topsin, mefenoxam, salicylic acid, flumorph, dimethomorph, metalaxyl-M, metalaxyl-M, diclocymet, flusulfamide, tolylfluanid, thifluzamide, flutolanil, tecloftalam, carpropamid, cyflufenamid, fenhexamid, fenoxanil, silthiopham, furametpyr, penthiopyrad, mandipropamid, zoxamide, fenfuram, carboxin, chlozolinate, iprodione, azoxystrobin, dimoxystrobin, fluoxastrobin, kresoxim-methyl, metominostrobin, orysastrobin, picoxystrobin, pyraclostrobin, trifloxystrobin, enestroburin, fenaminstrobin, azaconazole, bromuconazole, cyproconazole, difenoconazole, diniconazole, diniconazole-M, epoxiconazole, fenbuconazole, fluoroquinazole, flusilazole, flutriafol, hexaconazole, imidazole, ipconazole, metconazole, myclobutanil, penconazole, propiconazole, prothioconazole, simeconazole, tebuconazole, tetraconazole, triadimenol, triticonazole, bitertanol, thiabendazole, furidazol, imazalil, imazalil-M, prochloraz, triflumizole, cyazofamid, fenamidone, oxpoconazole, pefurazoate, famoxadone, pyrisoxazole, hymexazol, oxadixyl, ethaboxam, etridiazole, octhilinone, benthiazole, dodemorph, fenpropimorph, tridemorph, fenpiclonil, fludioxonil, fluazinam, pyrifenox, boscalid, fluopicolide, cyprodinil, diflumetorim, ferimzone, mepanipyrim, pyrimethanil, fenarimol, chinomethionate, dithianon, ethoxyquinoline, hydroxyquinoline, proquinazid, quinoxyfen, diethofencarb, iprovalicarb, benthiavalicarb-isopropyl, propamocarb, methasulfocarb, ediphenphos, Iprobenfos, pyrazophos, tolclofos-methyl, blastidin, kasugamycin, polyoxins, polyoxin, validamycin, validamycin, streptomycin, metalaxyl, furaxyl, benalaxyl, furamide, Mepronil, carbendazim, benomyl, methylthiocarb, triazolone, bupirimate, dimethirimol, ethellorimol, captafol, captan, folpet, vinclozolin, *Fluorochlorine sclerotium*, dimethachlon, isoprothiolane, kitazin, bismerthiazol, quintozene, mancozeb, propineb, phosethyl-al, Sulphur, Bordeaux solution, copper sulfate, copper oxychloride, cuprous oxide, copper hydroxide, metrafenone, pencycuron, diclomezine, phthalide, pyroqmlon, spiroxamine, tricyclazole, triforine, dofidine, guazatine, guazatine, dicloran, elvaron, tolylfluanid, indoxyl ester, fenaminosulf, oxolinic acid, probenazole, bronopol, iodomethane, metham, methyl isothiocyanate, dazomet, Nemamort, lythidathion, cadusafos, fensulfothion, weibaimu, dilinyl ester, cotton wool, dichloroisopropyl ether, thiazol, thiophosphine, fossophos, thionazin, fenamiphos, ethoprophos, dichlofenthion, isazofos, fosthietan, oxamyl, aldicarb, carbofuran, sulfuryl fluoride, dichloropropene, dichloroisonicotinic acid, or probenazole;

the mass percentage of the α-amino acrylic derivative I of the present invention in the compound fungicide was 1%-90%, and the mass ratio of the α-amino acrylic derivatives I to the above described commercial fungicide was from 1%:99% to 99%:1%;

the formulation suitable for the compound fungicide was wettable powder, microcapsule suspension, dispersible liquid preparation, dispersible solid preparation, seed treatment emulsion, water emulsion, large granule, microemulsion, oil suspensions, pesticide-coated seeds, water-soluble granules, soluble concentrates, water-dispersible granules, poison valleys, aerosols, block poison baits, slow-release blocks, concentrated poison baits, capsule granules, dry seed dressing powder, emulsifiable concentrate, electrostatic spray of wettable powder, water-in-oil emulsion, oil-in-water emulsion, aerosol cans, fine granules, aerosol candles, aerosol cans, aerosol sticks, seed treatment suspensions, aerosol tablets, aerosol pills, granular poison bait, hot aerosol, medicinal lacquer, seed treatment liquid, fine particles, oil-dispersible powder, flake poison bait, thick glue, pouring agent, spreading agent, suspension emulsion, film-forming oil agent, soluble powder, seed treated with water-soluble powders, ultra-low-volume suspensions, tracking powders, ultra-low-volume liquids, or water-dispersed powders for wet dressing;

the plant suitable for the compound fungicide was rice, wheat, barley, oats, corn, sorghum, sweet potato, potato, cassava, soybean, pea, broad bean, pea, mung bean, adzuki bean, cotton, silkworm, peanut, rape, sesame, sunflower, beet, sugar cane, coffee, cocoa, *ginseng*, fritillary, rubber, coconut, oil palm, sisal, tobacco, tomato, pepper, radish, cucumber, cabbage, celery, mustard, shallot, garlic, watermelon, melon, cantaloupe, *papaya*, apple, citrus, peach tree, tea, wild vegetables, bamboo shoots, hops, pepper, banana, *papaya*, orchid, or bonsai;

the disease controlled by the compound fungicide was *Puccinia striiformis* West; *FusaHum graminearum* Sehw. or *F. ardenaceum* (Fr.) Sacc.; *Blumeria graminis* F. sp. *Tritici*; Wheat yellow mosaic virus, WYMV; *Gerlachia nivalis*; *Bipolaris sorokiniana* (Sacc. ex Sorok.) Shoem; *Tilletia caries* or *Toilletia foetida*; *Gaeumannomyces graminis* var; *Rhizoctonia cereadis* van der Hoeven apud. Boerema & Verhoeven; *Sclerophthora macrospora* (Sacc.) Thrium., Shaw et *Narasimhan* var. *triticina* Wang & Zhang, J. Yunnan Agr.; *Phytophthora infestans* (Mont.) de Bary; *Synchytrium endobioticum* (Schilberszky) percivadl; *Streptomyces scabies* (Thaxter) Waks. et Henvici; *Alternaria solani*. Sorauer; *Clavibacter michiganensis* subsp. *sepedonicus*; *Ralstonia solanacearum* E. F. Smith; *Erwinia carotovora* subsp. *Atroseptica* (Van Hall) Dye; Potato virus and viroid disease including Pottao Virus Y, PVY; *Pectobacterium carotovorum* subsp. *carotovorum*, *P. atrosepticum* or *Dickeya chrysanthemi*; *Fusarium* spp., *Fusarium sambicinum*, *Fusarium solani*, *Fusarium solani* var. *coeruleum*, *Fusarium avenaceum*, *Fusarium sulphureum*, *Fusarium oxysporum*, *Fusarium equiseti*, *Fusarium acuminatum*, *Fusarium graminearum*, *Fusarium scirpi*, *Fusarium crookwellense*, *Fusarium trichothecioides*, *Fusarium sporotrichioides*, *Fusarium redolens*, *Fusarium moniliforme*, *Fusarium moniliforme* var. *intermedium*, *F. moniliforme* var. *zhejiangense*, *Fusarium culmorum*, *Fusarium tricinctum* or *Fusarium semitectum*; *Verticillium dahliae* Kleb.; *Rhizoctonia solanikuhn*; *Ralstonia solanacearum* E. F. Smith; *Clavibacter michiganense* subsp. *sepedonicum* (Spieckermann & Kotthoff) Davis, Gillaspie, Vidaver and Harris.; *Erwinia carotovora* subsp. *atroseptica* (Van Hall) Dye; *Erwinia carotovora* subsp. *carotovora* (Jones) Bergeyetal, *Erwinia carotovora* subsp. *atroseptica* (VanHall) Dye or *Erwinia chrysanthemi* Burkholder, McFaddenet Dimock; *Fusarium oxysporum* f. sp. *vesinfectum* (Atk.) Snyder et Hansen; *Verticillium dahliae* Kleb. or *Verticillium alboatrum* Reinke et Berthold; *Xanthomonas campestris* pv *malvacearum* (E F Smith) Dowson; Cotton red leaf blight disease; *Rhizoctonia solani* Kohn; *Fusarium* spp., or *Phythium aphanidermatum* (Eds.) Fitzp.; *Colletotrichum gossypii* South W.; *Fusarium oxysporum* f. sp. *vesinfectum* (Atk.) Snyder et Hansen, *Verticillium dahliae* Kleb.; *Mygnaporthe grasea*; *Rhizoctonia solani* Kuhn; *Bipolaris oryzae*; *Sclerotium oryzae*; *Gibberella fujikuroi*; *Sclerophthora macrospora* (Saccardo) Thirumalachar, Shaw & Narasimhan var. *oryzae* Zhang & Liu; *Ustilaginoidea virens* (Cooke) P. Henn); *Sarocladium oryzae* (Sawada) W. Gams. et Webster; *Xanthomonas oryzae* pv. *oryzae*; *Xanthomonas oryzae* pv. *oryzicola*; *Erwinia chrysanthemi* pv. *zeae* (Sabet) Victria, Arboleda et Munoz.; Rice stripe virus, RSV; Rice black streaked dwarf virus, RBSDV; *Helminthosporium sigmoideum* var. Irregulare Crall. EtTull.; *Setosphaeria turcica*; *Bipolaris maydis* Nisik & Miyake; *Bipolaris carbonum* Wilson; *Physodenna maydis* Miyabe; *Rhizoctonia solani* Kühn; *Puccinia sorghi* Schw.; *Sphacelotheca reiliana* (Kuhn) Clint.; *Fusarium* spp. or *Pythium* spp.; *Ustilago maydis* (DC.) Corda.; *Stenocarpell maydis* (Berk) Sutton, macrospora (Earle) Sutton or *Diplodia frumenti* Ell. et Ev.; Maize rough dwarf virus and *Fusarium moniliforme*; *Sclerotinia sclerotiorum* (Lib.) de Bary; Rape virus diseases caused by TuMV, CMV, YoMV; *Hyaloperonospora parasitica*; *Albugo candida* (Pers.) Kuntze; *Phytophthora sojae*, *Fusarium* spp., *Pythium* spp. or *Rhizoctoni solani*; *Sclerotinia sclerotiorum* (Lib.) de Bary; *Cercospora sojina*; Soybean mosaic virus, SMV; *Heterodera glycines* Ichinohe; *Heferodera glycines* Inhinohe, *Meloidogyne* spp., *Rotylenchulus reniformis, Belonolaimus gracilis B. longicaudatus, Hoplolaimus Columbus, Pratylenchus* or *Tylenchorhynchus* spp.; *Phakopsora pachyrhizi* Sydow; *Glomerella glycines* (Hori) Lehman et Wolf; *Xanthomonas campestris* pv; *Septoria glycines* Hemmi; *Peronospora manschurica* (Naum.) Syd.; *Pseudomonas solanacearum* (Smith); *Diplodia gossypina* Cooke; *Fusarium* spp.; *Mycosphaerella arachidicola* (Hori) Jenk; *Phoma arachidicola* Marass; *Mesocriconema ornata*; *Sphaceloma arachidis* Bitaucourtet Jenkins; *Ralstonia solanacearum* Yabuuhi et al.; *Pseudomonas syringae* pv. *tabaci*; *Erwinia carotovora* subsp. *carotovora*; *Pseudomonas angulata*; *Phytophthora parasitica* var. *nicotianae* (Breda de Hean) Tucker; Alter aria *alternata* (Fries) Keissler; *Cercospora nicotianae* Ell. & Ev.; *Colletotrichum micotianae* Averna; *Thielaviopsis basicola* (Berk. & Br.) Ferr.; *Fusarium oxyporum*, *F. solani*; *Pythium* spp.; *Rhizoctonia solani* Kuhn; *Ascochyta gossypii* Syd.; *Erysiphe cicho-*

*racearum* DC.; *Sclerotium rolfsii* Sacc; *Sclerotium rolfsii* Sacc.; Tobacco mosaic virus, TMV; Cucumber mosaic virus, CMV; Tobacco etch virus, TEV; *Peronospora parasitica* (Persoon: Fries) Fries; *Erwinia carotovora* subsp. *Carotovora*; Heart disease caused by dried cabbage; Cabbage virus disease caused by TuMV, CMV, TMV; *Alternaria brassicae* (Berk.) Sace.; *Xanthomonas campestris* pv. *campestris; Colletotrichum higginsianum* Sacc.; *Plasmodiophora brassicae* Woron; *Pseudomonas syringae* pv. tomato; *Phytophthora infestans*; Tomato stalk rot; *Leveillula taurica* (Lev.); Am. *Oidium lycopersici* Cooke et Mass.; *Pythium* spp., *Phytophthora capsici* Leonian; Tomato spotted wilt virus, TSWV; *Pseudomonas syringae* pv. tomato; Tomato yellow leaf curl China virus, TYLCCNV; *Fulvia fulva* (Cooke) Cif; Tomato virus disease caused by TMV, ToMV, CMV; *Phytophthora infestans; Rhizoctonia solani, Phytophthora parasitica* Dast.; Tomato fruit deformation disease; Tomato perforator disease; Tomato black ring nepovirus, TBRV; *Ditylenchus destructor* Thorne; *Phytophthora nicotianae* van Breda de Haan; *Colletotrichum atramentarium* (Berkeley et Broome) Taubenhaus; *Colletotrichum atramentarium* (Berkeley et Broome) Taubenhaus; *Rhizopus stolonifera* (Ehrenb.) Lind; Tomato heart rot disease; *Rhizopus stolonifer* (Ehrenb.) Lind; Tomato hypothermia disorder disease; Tomato giant bud disease; Tomato Physiological leaf curling disease; Tomato cataplexy disease; Tomato falling flower and fruit disease; Tomato bud blight disease; *Pectobacterium carotovorum* subsp. *carotovorum; Fusarium solani; Rhizoctonia colani* Kuhn.; Tomato sunburn disease; *Xanthomonas gardneri; Trichothecium roseurn* Link; Tomato dehiscence disease; *Clavibater michiganensis* (Smith) Davis et al., subsp. *michiganensis* (Smith) Davis et al.; Tomato navel rot disease; *Helminthosporium carposaprum; Pseudomonas syringae* pv. tomato (Okabe) Young, Dye & Wilkie; TMV, CMV; Tomato Yellow Leaf Curl Disease, TYLCD; *Phytophthora capsici* or *Phytophthora parasitica; Sclerotinia sclerotiorum* (Lib.) De Bary.; *Ralstonia solanacearum; Phomopsis vexans* (Sacc. Et Syd.) Harter.; *Verticillium dahliae* Kleb.; *Corynespora cassiicola; Alternaria solani* (E11. et Mart.) Jones et Grout; Eggplant mosaic virus, EMV; *Phyllosticta melongenae* Sawada; *Fulvia fulva* (Cooke) Cif.; *Sphaerotheca fuliginea* (Schlecht) Poll.; *Phyllosticta melongenae* Sawada; *Pseudocercospora deightonii* Minter; *Cercospora solani-melongenae* Chupp or *C. melongenae* Welles; *Corynespora cassiicola* (Berk. et Curt.) Wei.; *Phytophthora infestans* de Bary; *Colletotrichum truncatum* (Schw.) Andrus et Moore; *Rhizopus nigricans* Ehrenb.; *Fusarium oxysporum* f. sp. *melongenae* Matuo et lshigami Schlecht.; *Botrytis cinerea* Per.; *Rhizoctonia solani* Kuhn; Capsicum mottle virus, CaMV; *Alternaria solani* (E11. Et Mart.) Jones et Grout; *Stemphylium lycopersici* (Enjoji) Yamamoto; *Phyllosticta capsici* Speg.; *Phaeoramularia capsicicola* (Vassiljevskiy) Deighton; *Fusarium* sp., *Alternaria alternata* or *Penicillium* sp.; *Cladosporium capsici* (March et Stey.) Kovachersky; *Fusarium oxysporum* f. sp. *Vasinfectum* (Atk.) Synder et Hansen; *Sclerotinia sclerotiorum* (Libert) de Bery; Hot pepper sunburn; *Capsicum* mottle virus; *Capsicum* malformed fruit disease; Pepper navel rot disease; *Erwinia carotovora* subsp.; *Xanthomonas campestris* pv. *Vesicatoria; Capsicum* mottle virus; *Pythium aphanidermatum* (Eds.) Fitzp.; *Drechslera ellisii* Danguah; *Septoria lycopersici* Speg; *Alternaria alternata; Verticillium dahliae* Kleb; *Pseudomonas syringae* pv. aptata Young. Dye & wilkie; *Choanephora manshurica* (Saito. et Nagamoto) Tai; *Fusarium vasinfectum* Atk.; *Rhizoctonia solani; Colletotrichum acutatum; Cercospora capsica* HealdetWolf; *Peronospora capsici* Tao et Li sp. nov.; *Botrytis cinerea* Pers or *Sclerotinia fuckeliana* (de Bary) Whetzel; *Stemphylium solani* Weber; *Fulvia fulva* (Cooke) Cif.; *Pythium aphanidermatum; Phytophthora capsici* Leonian; *Plasmopara viticola* (Berk. dt Curtis) Berl. Et de Toni; *Uncinula necator; Phaeoisariopsis vitis* (Lev.); Grapevine leafroll lassociated virus, GLRaVs; Grapevine fan leaf disease, GFLV; *Phakopsora ampelopsidis* Diet. et Syd.; *Acrospermum viticola* IKata; *Septoria ampelina* Berk & Curt; *Cercospora roesle, Cercospora truncata; Acrospermun viticola; Cristulariella moricola*; Grape new shoot wasting disease; Grape spotted wilt virus, GSWV; Grape wasting disease, GSV; Grape stripe disease; Grapevine flavescence doree virus, GFDV; Grape infection necrosis disease; Grape yellow spot disease; Grapevine enation disease virus, GEDV; Grape veinal necrosis; Grapevine fleck virus, GFkV; Grapecine asteroid mosaic virus, GAMY; *Xyllela fastidiosa*, Wells et al; *Coniothyrium diplodiella* (Speq.) Sacc; *Colletotrichum gloeosporioides* Penz; *Guignardia baccae* (Cay.) Trcz; *Botrytis cinereal* Pers.; *Elsinoe ampelina* (de Bary) Shear; *Guignardia bidwellii; Pestalotia uvicola* Speg; *Leptothyrium pomi* Sacc.; *Cladosporium herbarum; Leptoth triumpomi; Melanoconium fuligineum* (Schr. et viala) Cavara; Grape *cladosporium* rot disease; *Penicillium; Alternaria viniferae; Valsa mali* Miyabe et Yamada, *Cytospora mandshurica* Miura; *Botryosphaeria berengeriana* (Moug. ex fr). Ces. etdeNot; *Botryospuaeria berengeriana* de Not. t. sp. *Piricola* (Nose) Kogonezawa et Sukuma; *Nectria galligena; Nummularia discreta* (Schw.) Tul.; *Corticium salmonicolor* Berk. et Br.; *Diaporthe eres* Nitschke; *Lasiodiplodia pseudotheobromae; Colletotrichum gloeosporioides* (Penz.) Penz. et Sacc.; *Alternaria alternate, Trichothecium roseum; Gymnosporangium yamadai* Miyabe; *Monilinia mali* (Takab.) Whetzel; *Monilinia fructigena; Physalospora obtuse* Schw. Cooke; *Phytophthora cactorum* (Leb. et Cohn.) Schrot.; *Gloeodes pomigina* (Schw) Colby; *Diplocarpon mali* Y. Harada & Sawamura or *Marssonina coronaria* (Ell. & J. J. Davis) J. J. Davis, syn. *Marssonina mali* (Henn) S. Ito) Davis, *Diplocarpon mali* Harada et Sawamura; *Alternaria alternaria* f. sp *mali; Alternaria mali* Roberts; *Phyllosticta pirina* Sacc., *Coryneum foliicolum; Podosphaera leucotricha* (Ell. et Ev.) Salm; *Fusicladium dendriticum* (wallr.) Fuck.; *Chondrosiereum pur-puteum* (Pers. Fr.) Pougar; *Fusarium solani* (Mart.) App. Et, *Fusarium camptoceras*; Apple armillariella root rot disease; *Rmillariella tabescens* (Scop., Fr.) Sing.; *Sclerotium rolfsii* Sacc.; *Heliocobasidium brebissonini; Rosellinia necatrix; Agrobacterium tumefaciens*; Stem pitting virus, SPV; Apple scar skin viroid, ASSVd; Apaya ring spot virus, PRSV); Apple green crinkle virus, APCV; Apple fruit shrink disease; Apple little leaf disease; Apple yellow leaf disease; Apple bitter rot disease; Apple water heart disease; Apple Superficial Scald disease; Hongyu apple spot disease; Golden delicious rust disease; *Penicillium expansum* (Link) Thom; *Rhizopus oryzae*; Apple sarcocarp pink disease; Apple sarcocarp flesh browning disease; Apple brown heart disease; *Venturia piritna* Aderh or *Venturia nashicola* Tanak et Yamamota or *Fusicladium plrinum* (Lib) Fuck; *Physalospora piricola* Nose, *Macrophoma kuwatsukai* Hara; *Valsa mali* Miyabe et Yamada var. pyri Y. J. Lu; *Athelia rolfsii* Tu et Kim.; *Fomes truncatospora* (Lloyd) Teng, *Fomes marginatus* (Eers. ex Fr) Gill, *Phellinus pomacens* (Pers. es Grag) Quel or *Pyropolyporus fomentarius* (L. ex Fr.) Teng; *Bacillus atrophaeus; Gymnosporangium asiaticum* Miyabe ex Yamada; *Alternaria kikuchiana* Tanaka; *Phyllosticta pirina* Sacc.; *Mycosphaerella sentina* (Fr.) Schr ter or *Septoria piricola* Desm.; *Gloeodes pomigena* (Schw)Colby; Pear top rot disease; Pear shrink disease; Pear yellow-leaf disease;

*Colletotrichum gloeosporioides; Phomopsis amygdalina* Canonaco; *Macrophoma kawatsukai* Hara; *Aspergillus aculeatus; Phomopsis amygdali; Podosphaera tridactyta, Sphaerotheca pannosa; Monilinia laxa; Cladosporium carpophilum; Eriophyes catacardiae* Keifer; *Clasdosporium hergbrum; Taphrina deformans; Clasterosporium carpophilum* and *Pseudocercospora circumscissa; Xanthomonas arboricola* pv. *pruni;* Peach leaf spot; *Puccinia striiformis;* Peach mosaic-associated virus, PMV; Prunus necrotic ringspot virus; *Valsa leucostoma; Botryosphaeria dothidea; Fomes fulvus, Trametes hispida* or *Polystictus unicolor; Cytospora leucostma* Sace.; *Agrobacterium tumefaciens; Fusarium solani* (Mart.) APP. et wollenw.; *Meloidogyne* spp.; *Candidatus Liberibacter* spp.; Citrus excocortis virus; Citrus tatter leaf virus, CTLV; Citrus tristeza virus, CTV; Satsuma dwarf virus, SDV; *Xanthomonas citri* subsp. *citri; Elsinoe* few cetti; *Colletotrichum gloeosporioides* Penz; *Phytophthora parasitica* (Dastur); *Diaporthe medusaea* (Nitsehke); *Phytophthora* sp., *Fusarium* sp., *Diplodia* sp.; *Capnodium citri* (Mont.); *Mycosphaerlla citri; Mycosphaerella citri* Whit.; *Mycosphaerella citri* Whit.; *Corticum salmonicolor* Berk.; *Helicobasidium* sp.; *Rhizoctonia solani; Phytophthora* spp.; Banana bunchy top virus, BBTV; Heart rot disease of banana leaves and flowers; *Fusarium oxysporun* f. sp. *Cubense; Cercosproa musae; Mycosphaerella. musicola* J. L. Mulder; *Helminthosporium torulosum* (Syd.) Ashby; *Marcophoma musae* (Cooke) Berl. et Vogl; *Pyricularia grise; Colletotrchum musae* (Berk. etCurt) v. Arx; *Fusarium semitectum; Pseudomonas symngae* pv. *maculicola* (McCulloch) Young; *Sclerotinia sclerotiorum* (Libert) de Bery; *Xanthomonas canpestris* (Panmmel) Dowson; *Alternaria brassicae* (Berk.) Sacc; *Alternaria brassicae* Sacc; Cabbage split ball disease; Cabbage virus disease caused by TuMV, CMV, TMV; *Erwinia carotovora* pv. *carotovora* Dye; Cabbage early bolting; *Hyaloperonospora parasitica; Colletotrichum truncatum; Phoma lingam* (Tode ex Schw.) Desm.; *Ceratocystis paradoxa* Moreau; *Sporisorium scitamineum* (Syd.); *Clavibacter xyli* subsp Xyli Davis et al); *Cochliobolus stenospilus* (Drechs) Mats et Yam and *Bipolaris stenospila* (Drechs) Shoemaker; *Puccinia melanocephala* Sydow or *Puccinia kuehnii* Butl.; *Sphaceloothea cruenta* (Kudhn) Potter; *Mycosphaerella holci* Tehon; *Colletotrichum graminicola* (Cesati) Wilson.; *Setosphaeria turcica* (Luttr.) Leonard & Suggs; Sugarcane mosaic virus, SMV.

The α-amino acrylic derivative I of the present invention is in combination with a commercial antiviral agent for controlling agricultural, forestry and horticultural plant virus diseases.

The α-amino acrylic derivative I of the present invention was in combination with any agriculturally acceptable pesticidal adjuvant agent and any one or more of the following commercial antiviral agents for preparing a compound antivirus agent and a compound plant activator;

the commercial antiviral agent was benzothiadiazole, tiadinil, methiadinil, 4-methyl-1,2,3-thiadiazole-5-carboxylic acid, Sodium 4-methyl-1,2,3-thiadiazole-5-carboxylate, ethyl 4-methyl-1,2,3-thiadiazole-5-carboxylate, ethyl 4-bromomethyl-1,2,3-thiadiazole-5-carboxylate, ethyl 4-iodomethyl-1,2,3-thiadiazole-5-carboxylate, 4-bromomethyl-5-methyl-1,2,3-thiadiazole, 4-iodomethyl-5-methyl-1,2,3-thiadiazole, ethyl 4,4-dibromomethyl-1,2,3-thiadiazole-5-carboxylate, 3,4-dichloroisothiazole-5-carboxylic acid, sodium 3,4-dichloroisothiazole-5-carboxylate, ethyl 3,4-dichloroisothiazole-5-carboxylic acid, DL-β-aminobutyric acid, virazole, antofine, ningnanmycin, methiadinil, salicylic acid, cytosinpeptidemycin, dichloroisonicotinic acid, probenazole, validoxylamine, or validamycin;

the mass percentage of the α-amino acrylic derivative I of the present invention in the compound antivirus agent or compound plant activator was 1%-90%, and the mass ratio of the α-amino acrylic derivatives I to the above described commercial antivirus agent was from 1%:99% to 99%:1%;

the formulation of the compound antivirus agent and compound plant activator was wettable powder, microcapsule suspension, dispersible liquid preparation, dispersible solid preparation, seed treatment emulsion, water emulsion, large granule, microemulsion, oil suspension Agents, pesticide-coated seeds, water-soluble granules, soluble concentrates, water-dispersible granules, poisonous grains, aerosols, block poison bait, slow-release block, concentrated poison bait, capsule granules, dry seed powder, emulsifiable concentrate, electrostatic spray for wettable powder, water-in-oil emulsion, oil-in-water emulsion, aerosol can, fine granules, smoke candle, smoke tube, smoke stick, seed treatment suspension agent, smoke flake, smoke pill, granular poisonous bait, Thermal mist, paint, seed treatment liquid, microparticle, oil-dispersible powder, flake poison, thick glue, pouring agent, spreading agent, suspension emulsion, film-forming oil agent, soluble powder, seed treatment water-soluble powder, ultra-low-capacity suspending agent, tracking powder, ultra-low capacity liquid, or water-dispersible powder for wet dressing;

the plant suitable for the compound antivirus agent and plant activator was rice, wheat, barley, oats, corn, sorghum, sweet potato, potato, cassava, soybean, pea bean, broad bean, pea, mung bean, adzuki bean, cotton, silkworm, Peanut, rapeseed, sesame, sunflower, beet, sugar cane, coffee, cocoa, *ginseng*, fritillary, rubber, coconut, oil palm, sisal, tobacco, tomato, pepper, radish, cucumber, cabbage, celery, mustard, shallot, garlic, watermelon, melon, cantaloupe, *papaya*, apple, citrus, peach tree, tea, wild vegetables, bamboo shoots, hops, pepper, banana, *papaya*, orchid, or bonsai;

the virus disease controlled by the compound antivirus agent and the compound plant activator was rice dwarf disease, yellow dwarf disease, stripe leaf blight, tomato fern leaf virus disease, pepper mosaic virus disease, tobacco vein necrosis virus disease, corn dwarf mosaic virus, cauliflower mosaic virus, citrus virus disease, orchid flower mosaic virus, or orchid ring spot virus.

The abbreviations of some compound names described in the present invention are listed as follows:

$Ac_2O$: Acetic anhydride;
AcONa: Sodium acetate;
BTH: Acibenzolar-S-Methyl;
DCM: Dichloromethane;
DIPEA: Ethyldiisopropylamine;
DMF: N,N-Dimethylformamide;
EA: Ethyl acetate;
EDCI: 1-Ethyl-3-(3-N-(3-dimethylaminopropyl)-N'-ethylcarbodiimide hydrochloride;
$Et_3N$: Triethylamine;
HOBt: 1-Hydroxybenzotriazole;
MeOH: Methanol;
PDA Culture: Potato Dextrose Agar Culture;
PyBOP: Benzotriazole-1-yl-oxytripyrrolidinophosphonium hexafluorophosphate;
TDL: Tiadinil;
THF: Tetrahydrofuran;
TMV: Tobacco mosaic virus.

TABLE 1

Structure and physical and chemical parameters of the α-amino acrylic derivatives I and intermediates of the present invention

| Number | m.p./° C. | Structure | ¹H NMR | Yield % | Shape |
|---|---|---|---|---|---|
| 1 | 163-164 | 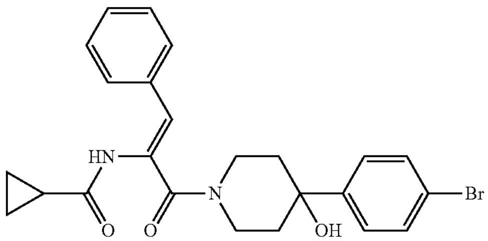 [SMILES: O=C(N/C(=C\c1ccccc1)C(=O)N1CCC(O)(c2ccc(Br)cc2)CC1)C1CC1] | ¹H NMR (400 MHz, DMSO) δ 10.05 (s, 1H), 7.70-7.17 (m, 9H), 6.17 (s, 1H), 5.25 (s, 1H), 4.21 (s, 1H), 4.02 (s, 1H), 3.45 (s, 1H), 3.06 (s, 1H), 2.08 (s, 1H), 1.87 (s, 2H), 1.60 (d, J = 38.9 Hz, 2H). | 66.7 | White solid |
| 2 | 124-126 | 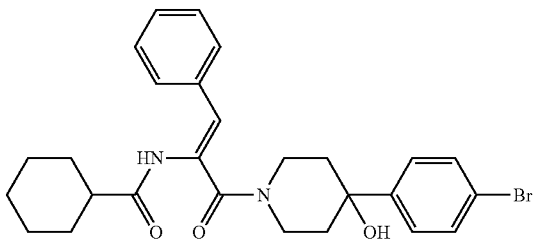 [SMILES: O=C(N/C(=C\c1ccccc1)C(=O)N1CCC(O)(c2ccc(Br)cc2)CC1)C1CCCCC1] | ¹H NMR (400 MHz, DMSO) δ 9.67 (d, J = 25.8 Hz, 1H), 7.52 (dd, J = 34.5, 14.0 Hz, 9H), 6.22 (d, J = 26.2 Hz, 1H), 5.29 (d, J = 26.8 Hz, 1H), 4.17 (d, J = 80.8 Hz, 2H), 3.46 (s, 1H), 3.11 (s, 1H), 2.10 (d, J = 25.0 Hz, 1H), 1.80 (s, 8H), 1.33 (d, J = 46.4 Hz, 6H). | 71.4 | Light yellow solid |
| 3 | 145-147 | 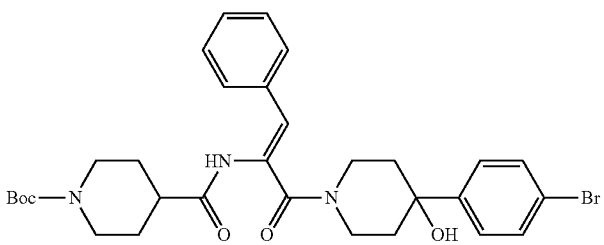 [SMILES: CC(C)(C)OC(=O)N1CCC(C(=O)N/C(=C\c2ccccc2)C(=O)N2CCC(O)(c3ccc(Br)cc3)CC2)CC1] | ¹H NMR (400 MHz, DMSO) δ 9.79 (s, 1H), 7.66-7.24 (m, 9H), 6.21 (s, 1H), 5.29 (s, 1H), 4.22 (s, 1H), 3.99 (s, 3H), 3.47 (s, 1H), 3.08 (s, 1H), 2.76 (s, 2H), 2.58 (s, 1H), 2.12 (s, 1H), 1.86 (s 1H) 1.76 (s 2H) 1.64 (d, J = 11.7 Hz, 1H), 1.56 (s, 1H), 1.46 (s, 2H), 1.41 (s, 9H). | 62.5 | Light yellow solid |
| 4 | 147-149 | 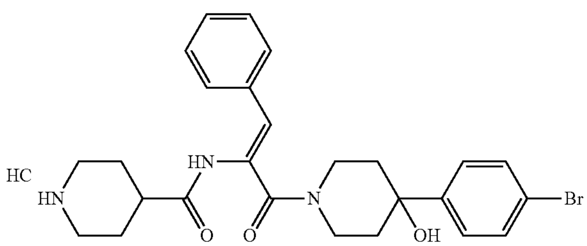 | ¹H NMR (400 MHz, D₂O) δ 7.27-6.84 (m, 9H), 5.78 (s, 1H), 3.72 (d, J = 28.1 Hz, 2H), 3.21 (s, 2H), 2.91 (s, 4H), 2.10-1.51 (m, 8H). | 96.3 | Orange solid |
| 5 | 195-197 | 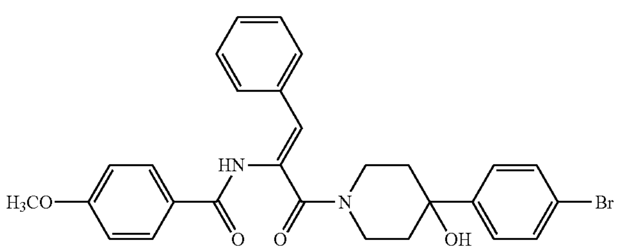 [SMILES: COc1ccc(C(=O)N/C(=C\c2ccccc2)C(=O)N2CCC(O)(c3ccc(Br)cc3)CC2)cc1] | ¹H NMR (400 MHz, DMSO) δ 10.14 (s, 1H), 8.02 (d, J = 8.6 Hz, 2H), 7.66-7.23 (m, 9H), 7.07 (d, J = 8.6 Hz, 2H), 6.43 (s, 1H), 5.28 (s, 1H), 4.23 (d, J = 23.7 Hz, 2H), 3.85 (s, 3H), 3.53 (s, 1H), 3.12 (s, 1H), 2.16 (s, 1H), 1.89 (s, 1H), 1.75-1.46 (m, 2H). | 93.8 | White solid |
| 6 | 129-130 | 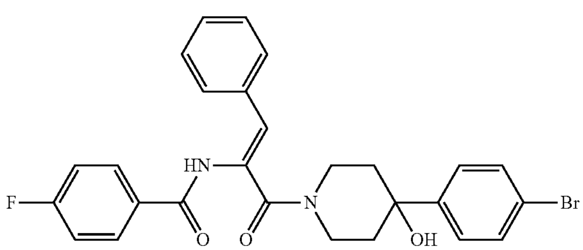 [SMILES: O=C(N/C(=C\c1ccccc1)C(=O)N1CCC(O)(c2ccc(Br)cc2)CC1)c1ccc(F)cc1] | ¹H NMR (400 MHz, DMSO) δ 10.35 (s, 1H), 8.21-7.06 (m, 13H), 6.48 (s, 1H), 5.30 (s, 1H), 4.73-4.08 (m, 2H), 3.56 (t, J = 34.2 Hz, 1H), 3.15 (s, 1H), 2.17 (d, J = 21.3 Hz, 1H), 1.92 (d, J = 9.5 Hz, 1H), 1.79-1.52 (m, 2H). | 63.8 | Light yellow solid |

TABLE 1-continued

Structure and physical and chemical parameters of the α-amino acrylic derivatives I and intermediates of the present invention

| Number | m.p./°C. | Structure | ¹H NMR | Yield % | Shape |
|---|---|---|---|---|---|
| 7 | 193-194 | (4-Cl-C6H4-C(O)NH-C(=CH-Ph)-C(O)-N-piperidine-4-OH-4-(4-Br-C6H4)) | ¹H NMR (400 MHz, DMSO) δ 10.40 (s, 1H), 8.05 (d, J = 8.5 Hz, 2H), 7.65-7.29 (m, 11H), 6.48 (s, 1H), 5.31 (s, 1H), 4.26 (s, 1H), 4.18 (s, 1H), 3.56 (s, 1H), 3.14 (s, 1H), 2.17 (s, 1H), 1.89 (s, 1H), 1.77-1.62 (m, 1H), 1.59 (s, 1H). | 83.3 | White solid |
| 8 | 186-188 | (4-Br-C6H4-C(O)NH-C(=CH-Ph)-C(O)-N-piperidine-4-OH-4-(4-Br-C6H4)) | ¹H NMR (400 MHz, DMSO) δ 10.39 (s, 1H), 7.96 (d, J = 8.5 Hz, 2H), 7.75 (d, J = 8.4 Hz, 2H), 7.65-7.27 (m, 9H), 6.47 (s, 1H), 5.30 (s, 1H), 4.22 (d, J = 24.7 Hz, 2H), 3.54 (s, 1H), 3.13 (s, 1H), 2.16 (s, 1H), 1.88 (s, 1H), 1.66 (d, J = 11.3 Hz, 1H), 1.56 (d, J = 11.2 Hz, 1H). | 44.1 | White solid |
| 9 | 130-131 | (4-F3C-C6H4-C(O)NH-C(=CH-Ph)-C(O)-N-piperidine-4-OH-4-(4-Br-C6H4)) | ¹H NMR (400 MHz, DMSO) δ 10.60 (s, 1H), 8.25 (d, J = 8.0 Hz, 1H), 7.98-7.24 (m, 13H), 6.53 (s, 1H), 5.34 (d, J = 13.2 Hz, 1H), 4.49 (d, J = 9.5 Hz, 1H), 4.38-4.15 (m, 1H), 3.52 (dd, J = 32.9, 20.0 Hz, 1H), 3.29-3.08 (m, 1H), 2.21 (s, 1H), 1.94 (d, J = 9.8 Hz, 1H), 1.71 (d, J = 11.8 Hz, 1H), 1.53 (d, J = 13.0 Hz, 1H). | 71.4 | Light yellow solid |
| 10 | 130-132 | (4-O2N-C6H4-C(O)NH-C(=CH-Ph)-C(O)-N-piperidine-4-OH-4-(4-Br-C6H4)) | ¹H NMR (400 MHz, DMSO) δ 10.67 (s, 1H), 8.52-7.10 (m, 13H), 6.53 (s, 1H), 5.33 (d, J = 15.4 Hz, 1H), 4.60-4.10 (m, 2H), 3.59 (s, 1H), 3.19 (d, J = 11.6 Hz, 1H), 2.32-2.11 (m, 1H), 1.92 (s, 1H), 1.78-1.49 (m, 2H). | 70.0 | Yellow solid |
| 11 | 128-129 | (3-O2N-C6H4-C(O)NH-C(=CH-Ph)-C(O)-N-piperidine-4-OH-4-(4-Br-C6H4)) | ¹H NMR (400 MHz, DMSO) δ 10.72 (s, 1H), 8.87 (s, 1H), 8.45 (t, J = 7.2 Hz, 2H), 7.85 (t, J = 8.0 Hz, 1H), 7.62 (d, J = 7.6 Hz, 2H), 7.57-7.36 (m, 7H), 7.32 (d, J = 7.3 Hz, 1H), 6.53 (s, 1H), 5.32 (s, 1H), 4.27 (s, 1H), 4.22 (s, 1H), 3.57 (s, 1H), 3.16 (d, J = 10.6 Hz, 1H), 2.18 (s, 1H), 1.91 (d, J = 8.0 Hz, 1H), 1.67 (d, J = 10.9 Hz, 1H), 1.60 (s, 1H). | 62.9 | Light yellow solid |

TABLE 1-continued

Structure and physical and chemical parameters of the α-amino acrylic derivatives I and intermediates of the present invention

| Number | m.p./°C. | Structure | ¹H NMR | Yield % | Shape |
|---|---|---|---|---|---|
| 12 | 122-124 | 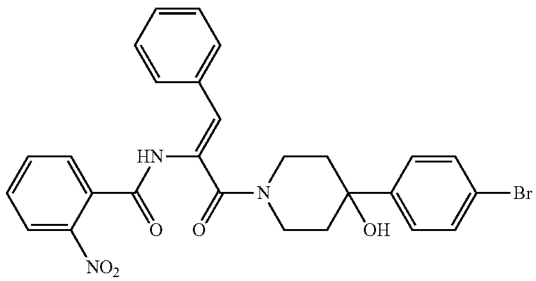 [SMILES: O=C(N/C(=C\c1ccccc1)C(=O)N1CCC(O)(c2ccc(Br)cc2)CC1)c1ccccc1[N+](=O)[O-]] | ¹H NMR (400 MHz, DMSO) δ 10.65 (s, 1H), 8.12 (d, J = 8.0 Hz, 1H), 7.86 (t, J = 7.4 Hz, 1H), 7.75 (t, J = 7.2 Hz, 1H), 7.69 (d, J = 7.2 Hz, 1H), 7.62 (d, J = 7.5 Hz, 2H), 7.50 (dd, J = 21.4, 8.1 Hz, 4H), 7.39 (t, J = 7.3 Hz, 2H), 7.30 (t, J = 7.1 Hz, 1H), 6.45 (s, 1H), 5.33 (s, 1H), 4.29 (s, 1H), 4.19 (d, J = 10.1 Hz, 1H), 3.60 (s, 1H), 3.16 (s, 1H), 2.20 (s, 1H), 2.02-1.82 (m, 1H), 1.65 (d, J = 20.7 Hz, 2H). | 71.9 | Yellow solid |
| 13 | 138-140 | 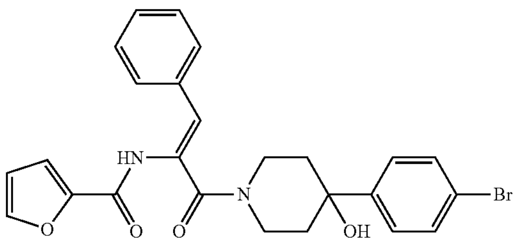 [SMILES: O=C(N/C(=C\c1ccccc1)C(=O)N1CCC(O)(c2ccc(Br)cc2)CC1)c1ccco1] | ¹H NMR (400 MHz, DMSO) δ 10.18 (s, 1H), 7.96 (s, 1H), 7.68-7.24 (m, 10H), 6.70 (d, J = 1.6 Hz, 1H), 6.44 (s, 1H), 5.29 (s, 1H), 4.21 (d, J = 42.6 Hz, 2H), 3.54 (s, 1H), 3.13 (s, 1H), 2.15 (s, 1H), 1.88 (s, 1H), 1.76-1.45 (m, 2H). | 70.5 | White solid |
| 14 | 134-136 | 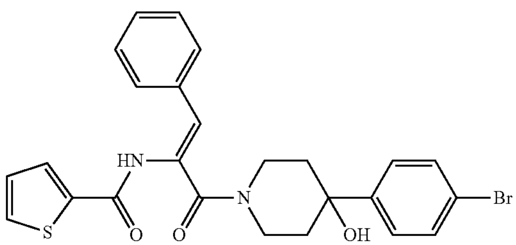 | ¹H NMR (400 MHz, DMSO) δ 10.36 (s, 1H), 8.07 (d, J = 3.1 Hz, 1H), 7.88 (d, J = 4.4 Hz, 1H), 7.67-7.16 (m, 10H), 6.46 (s, 1H), 5.30 (s, 1H), 4.21 (dd, J = 47.7, 10.3 Hz, 2H), 3.54 (t, J = 11.6 Hz, 1H), 3.13 (t, J = 11.2 Hz, 1H), 2.28-2.19 (m, 1H), 2.13 (s, 1H), 1.88 (s, 1H), 1.62 (dd, J = 40.0, 12.0 Hz, 2H). | 93.1 | Light yellow solid |
| 15 | 234-236 | 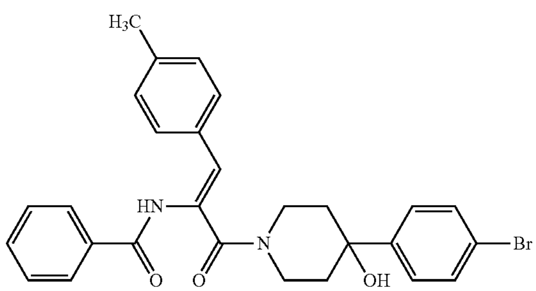 [SMILES: Cc1ccc(/C=C(\NC(=O)c2ccccc2)C(=O)N2CCC(O)(c3ccc(Br)cc3)CC2)cc1] | ¹H NMR (400 MHz, DMSO) δ 10.29 (s, 1H), 8.04 (d, J = 7.1 Hz, 2H), 7.65-7.43 (m, 9H), 7.20 (d, J = 8.0 Hz, 2H), 6.44 (s, 1H), 5.31 (s, 1H), 4.24 (d, J = 22.5 Hz, 2H), 3.54 (s, 1H), 3.13 (s, 1H), 2.30 (s, 3H), 2.17 (s, 1H), 1.89 (s, 1H), 1.73-1.50 (m, 2H). | 82.8 | White solid |
| 16 | 208-210 | 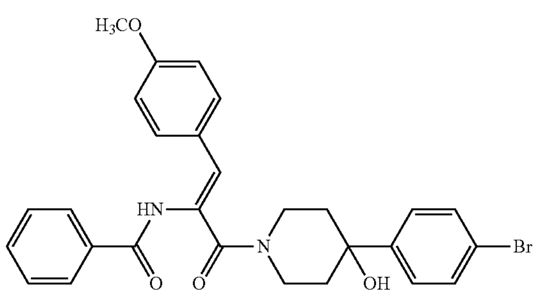 | ¹H NMR (400 MHz, DMSO) δ 10.26 (s, 1H), 8.06 (d, J = 7.1 Hz, 2H), 7.81-7.38 (m, 9H), 6.97 (d, J = 8.2 Hz, 2H), 6.46 (s, 1H), 5.30 (s, 1H), 4.25 (s, 2H), 3.76 (s, 3H), 3.55 (s, 1H), 3.15 (s, 1H), 2.17 (s, 1H), 1.89 (s, 1H), 1.61 (s, 2H). | 83.3 | Light yellow solid |

TABLE 1-continued

Structure and physical and chemical parameters of the α-amino acrylic derivatives I and intermediates of the present invention

| Number | m.p./ °C. | Structure | ¹H NMR | Yield % | Shape |
|---|---|---|---|---|---|
| 17 | 266-268 | (structure with 4-F phenyl) | ¹H NMR (400 MHz, DMSO) δ 10.34 (s, 1H), 8.06 (d, J = 7.3 Hz, 2H), 7.76-7.42 (m, 9H), 7.24 (t, J = 8.8 Hz, 2H), 6.50 (s, 1H), 5.32 (s, 1H), 4.26 (d, J = 22.4 Hz, 2H), 3.59 (s, 1H), 3.17 (s, 1H), 2.33-2.10 (m, 2H), 1.90 (s, 1H), 1.64 (dd, J = 35.1, 11.5 Hz, 2H). | 96.6 | White solid |
| 18 | 210-212 | (structure with 4-Cl phenyl) | ¹H NMR (400 MHz, DMSO) δ 10.35 (s, 1H), 8.04 (d, J = 7.4 Hz, 2H), 7.77-7.37 (m, 11H), 6.47 (s, 1H), 5.32 (s, 1H), 4.24 (dd, J = 41.5, 10.2 Hz, 2H), 3.57 (t, J = 11.2 Hz, 1H), 3.15 (t, J = 10.8 Hz, 1H), 2.20 (s, 1H), 1.91 (d, J = 10.4 Hz, 1H), 1.63 (dd, J = 38.0, 12.3 Hz, 2H). | 93.3 | White solid |
| 19 | 147-148 | (structure with 4-Br phenyl) | ¹H NMR (400 MHz, DMSO) δ 10.36 (s, 1H), 8.05 (d, J = 7.4 Hz, 2H), 7.55 (tt, J = 29.9, 8.5 Hz, 11H), 6.47 (s, 1H), 5.34 (s, 1H), 4.30 (d, J = 10.0 Hz, 1H), 4.19 (d, J = 10.4 Hz, 1H), 3.56 (d, J = 11.1 Hz, 1H), 3.16 (s, 1H), 2.25 (d, J = 19.4 Hz, 1H), 1.91 (s, 1H), 1.69 (d, J = 11.6 Hz, 1H), 1.59 (d, J = 12.1 Hz, 1H). | 77.4 | Light yellow solid |
| 20 | 137-139 | (structure with 4-CF₃ phenyl) | ¹H NMR (400 MHz, DMSO) δ 10.43 (d, J = 11.7 Hz, 1H), 8.20-7.28 (m, 13H), 6.54 (s, 1H), 5.32 (d, J = 7.0 Hz, 1H), 4.25 (d, J = 47.0 Hz, 2H), 3.60 (s, 1H), 3.18 (s, 1H), 2.22 (s, 1H), 1.92 (s, 1H), 1.65 (d, J = 41.2 Hz, 2H). | 95.7 | White solid |
| 21 | 118-120 | (structure with 3-CF₃ phenyl) | ¹H NMR (400 MHz, DMSO) δ 10.44 (s, 1H), 8.04-7.95 (m, 3H), 7.89 (d, J = 6.4 Hz, 1H), 7.62 (dd, J = 13.3, 6.8 Hz, 3H), 7.53 (t, J = 7.7 Hz, 4H), 7.48 (d, J = 8.5 Hz, 2H), 6.58 (s, 1H), 5.33 (s, 1H), 4.30 (d, J = 10.7 Hz, 1H), 4.19 (d, J = 12.0 Hz, 1H), 3.56 (t, J = 12.0 Hz, 1H), 3.15 (t, J = 11.5 Hz, 1H), 2.19 (s, 1H), 1.97-1.81 (m, 1H), 1.68 (d, J = 12.4 Hz, 1H), 1.58 (d, J = 12.4 Hz, 1H). | 93.8 | Light yellow solid |

TABLE 1-continued

Structure and physical and chemical parameters of the α-amino acrylic derivatives I and intermediates of the present invention

| Number | m.p./ °C. | Structure | ¹H NMR | Yield % | Shape |
|---|---|---|---|---|---|
| 22 | 149-151 | 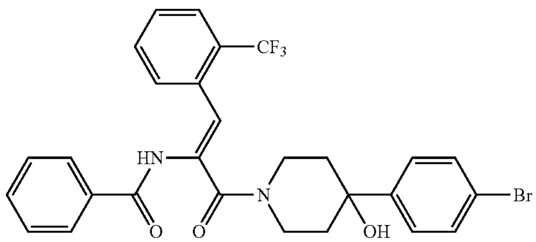 | ¹H NMR (400 MHz, DMSO) δ 10.24 (s, 1H), 8.34-7.28 (m, 14H), 6.41 (s, 1H), 5.33 (s, 1H), 4.29 (d, J = 11.0 Hz, 1H), 4.16 (d, J = 11.2 Hz, 1H), 3.56 (t, J = 11.8 Hz, 1H), 3.16 (t, J = 11.8 Hz, 1H), 2.11 (s, 1H), 1.90 (d, J = 10.0 Hz, 1H), 1.67 (d, J = 12.7 Hz, 1H), 1.58 (d, J = 12.5 Hz, 1H). | 87.5 | Light yellow solid |
| 23 | 186-188 | 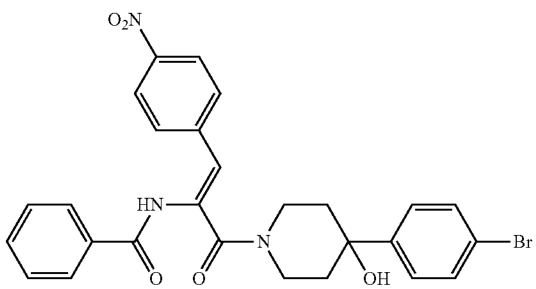 | ¹H NMR (400 MHz, DMSO) δ 10.54 (s, 1H), 8.25 (d, J = 8.6 Hz, 2H), 8.05 (s, 2H), 7.86 (s, 2H), 7.69-7.43 (m, 7H), 6.58 (s, 1H), 5.33 (d, J = 6.2 Hz, 1H), 4.32 (s, 1H), 4.18 (s, 1H), 3.61 (s, 1H), 3.18 (d, J = 10.4 Hz, 1H), 1.96 (d, J = 25.5 Hz, 2H), 1.69 (s, 1H), 1.59 (s, 1H).. | 90.3 | Orange solid |
| 24 | 180-182 | 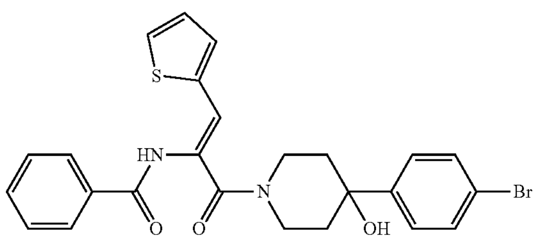 [SMILES: O=C(N/C(=C\c1ccco1)C(=O)N1CCC(O)(c2ccc(Br)cc2)CC1)c1ccccc1] | ¹H NMR (400 MHz, DMSO) δ 10.18 (d, J = 7.4 Hz, 1H), 8.22-6.85 (m, 12H), 5.30 (d, J = 4.7 Hz, 1H), 4.22 (s, 2H), 3.52 (s, 1H), 3.17 (s, 1H), 1.96 (d, J = 29.7 Hz, 2H), 1.62 (s, 2H). | 86.2 | Yellow solid |
| 25 | 134-135 | 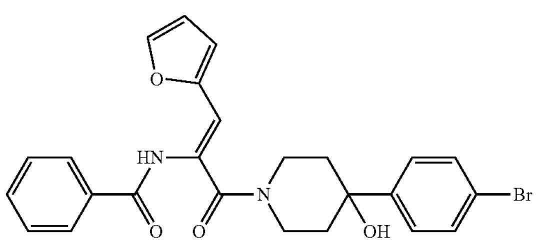 | ¹H NMR (400 MHz, DMSO) δ 10.13 (s, 1H), 8.07 (s, 2H), 7.82 (s, 1H), 7.72-7.33 (m, 7H), 6.65 (d, J = 35.5 Hz, 2H), 6.36 (s, 1H), 5.31 (d, J = 6.4 Hz, 1H), 4.18 (d, J = 81.7 Hz, 2H), 3.50 (s, 1H), 3.14 (s, 1H), 2.10 (s, 1H), 1.92 (s, 1H), 1.61 (d, J = 32.7 Hz, 2H). | 89.3 | Orange solid |
| 26 | 176-178 | 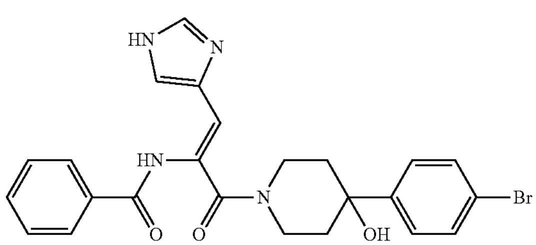 [SMILES: O=C(N/C(=C\c1c[nH]cn1)C(=O)N1CCC(O)(c2ccc(Br)cc2)CC1)c1ccccc1] | ¹H NMR (400 MHz, DMSO) δ 12.78-12.32 (m, 2H), 8.02 (d, J = 17.2 Hz, 3H), 7.86-7.43 (m, 7H), 7.35 (s, 1H), 5.93 (d, J = 6.3 Hz, 1H), 5.30 (s, 1H), 4.36 (s, 1H), 3.87 (s, 1H), 3.13 (s, 1H), 2.01 (d, J = 17.0 Hz, 2H), 1.58 (dd, J = 62.1, 12.4 Hz, 2H), 1.36-1.01 (m, 1H). | 60.7 | Gray solid |
| 27 | 212-214 | 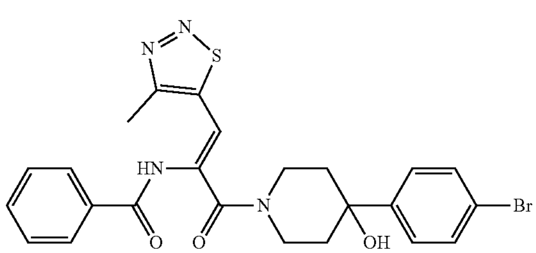 [SMILES: Cc1nnsc1/C=C(\NC(=O)c1ccccc1)C(=O)N1CCC(O)(c2ccc(Br)cc2)CC1] | ¹H NMR (400 MHz, DMSO) δ 10.50 (s, 1H), 8.05 (t, J = 15.7 Hz, 2H), 7.74-7.41 (m, 7H), 6.93 (d, J = 22.1 Hz, 1H), 5.34 (s, 1H), 4.31 (d, J = 10.7 Hz, 1H), 4.07 (d, J = 11.5 Hz, 1H), 3.58 (t J = 11.9 Hz 1H) 3.18 (t J = 11.6 Hz 1H) 2.76 (s 3H) 2.15 (s 1H) 1.93 (s 1H) 1.68 (d, J = 12.4 Hz, 1H), 1.58 (d, J = 12.2 Hz, 1H). | 62.6 | Yellow solid |

TABLE 1-continued

Structure and physical and chemical parameters of the α-amino acrylic derivatives I and intermediates of the present invention

| Number | m.p./°C. | Structure | ¹H NMR | Yield % | Shape |
|---|---|---|---|---|---|
| 28 | 231-233 | 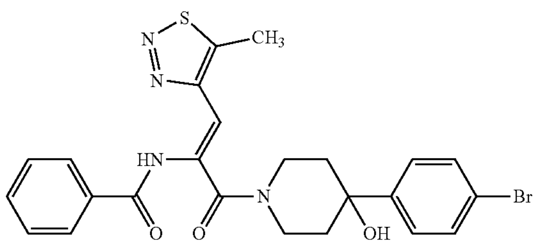 [SMILES: Cc1snnc1/C=C(\NC(=O)c1ccccc1)C(=O)N1CCC(O)(c2ccc(Br)cc2)CC1] | ¹H NMR (400 MHz, DMSO) δ 11.37 (s, 1H), 8.24-7.28 (m, 9H), 6.16 (s, 1H), 5.32 (s, 1H), 4.39 (s, 1H), 3.97 (d, J = 36.1 Hz, 2H), 3.18 (s, 1H), 2.06 (s, 3H), 1.61 (d, J = 65.9 Hz, 2H), 1.19 (s, 2H). | 47.2 | Yellow solid |
| 29 | 166-168 | 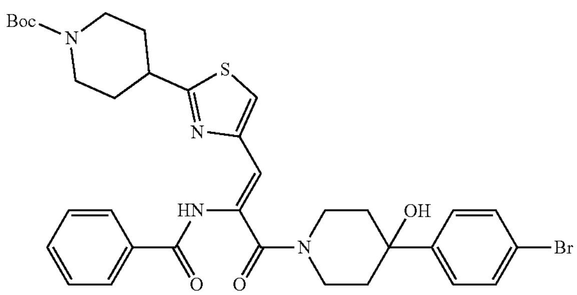 [SMILES: CC(C)(C)OC(=O)N1CCC(c2nc(/C=C(\NC(=O)c3ccccc3)C(=O)N3CCC(O)(c4ccc(Br)cc4)CC3)cs2)CC1] | ¹H NMR (400 MHz, DMSO) δ 11.90 (s, 1H), 8.35-6.98 (m, 10H), 6.04 (s, 1H), 5.30 (s, 1H), 4.07 (t, J = 100.7 Hz, 4H), 3.13 (s, 1H), 2.89 (s, 2H), 2.03 (s, 4H), 1.54 (d, J = 87.7 Hz, 15H). | 86.0 | Yellow solid |
| 30 | 114-115 | 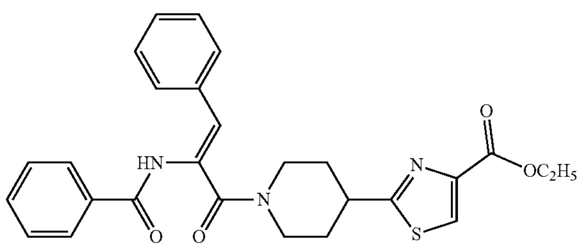 [SMILES: CCOC(=O)c1csc(C2CCN(C(=O)/C(=C/c3ccccc3)NC(=O)c3ccccc3)CC2)n1] | ¹H NMR (400 MHz, CDCl₃) δ 8.93 (s, 1H), 8.11 (s, 1H), 7.88-7.80 (m, 2H), 7.53-7.28 (m, 9H), 6.12 (s, 1H), 4.48 (s, 1H), 3.38 (ddd, J = 15.3, 7.7, 3.7 Hz, 2H), 2.89 (s, 1H), 2.21 (d, J = 11.3 Hz, 2H), 2.04 (t, J = 15.3 Hz, 1H), 1.84 (s, 1H), 1.74 (s, 1H), 1.41 (t, J = 7.1 Hz, 3H). | 94.7 | Light yellow solid |
| 31 | 118-120 | 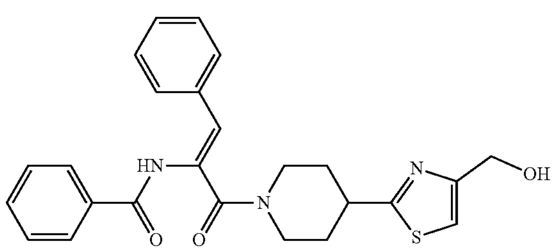 [SMILES: O=C(N/C(=C\c1ccccc1)C(=O)N1CCC(c2nc(CO)cs2)CC1)c1ccccc1] | ¹H NMR (400 MHz, CDCl₃) δ 8.95 (s, 1H), 7.85 (d, J = 7.5 Hz, 2H), 7.53-7.31 (m, 8H), 7.11 (s, 1H), 6.15 (s, 1H), 4.77 (s, 2H), 4.46 (s, 2H), 3.38 (s, 1H), 3.27 (t, J = 11.3 Hz, 1H), 2.94 (s, 1H), 2.17 (d, J = 12.1 Hz, 2H), 2.06-1.95 (m, 1H), 1.85 (s, 1H). | 85.7 | White solid |
| 32 | 185-187 | 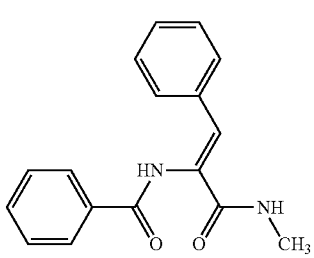 [SMILES: CNC(=O)/C(=C/c1ccccc1)NC(=O)c1ccccc1] | ¹H NMR (400 MHz, DMSO) δ 9.96 (s, 1H), 8.08 (dd, J = 33.9, 5.7 Hz, 3H), 7.56 (dt, J = 15.1, 7.7 Hz, 5H), 7.46-7.19 (m, 4H), 2.71 (d, J = 4.3 Hz, 3H). | 73.1 | White solid |

TABLE 1-continued

Structure and physical and chemical parameters of the α-amino acrylic derivatives I and intermediates of the present invention

| Number | m.p./ °C. | Structure | ¹H NMR | Yield % | Shape |
|---|---|---|---|---|---|
| 33 | 166-168 | 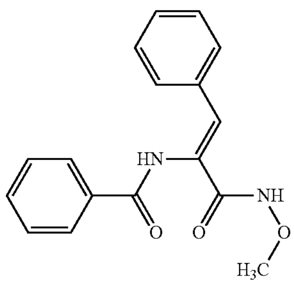 [SMILES: CONC(=O)/C(=C/c1ccccc1)NC(=O)c1ccccc1] | ¹H NMR (400 MHz, DMSO) δ 11.56 (d, J = 12.2 Hz, 1H), 10.02 (d, J = 11.3 Hz, 1H), 8.02 (d, J = 7.7 Hz, 2H), 7.56 (dt, J = 14.4, 6.7 Hz, 5H), 7.34 (dt, J = 22.4, 6.9 Hz, 3H), 7.10 (d, J = 10.7 Hz, 1H), 3.67 (d, J = 5.0 Hz, 3H). | 75.0 | Yellow solid |
| 34 | 147-148 | 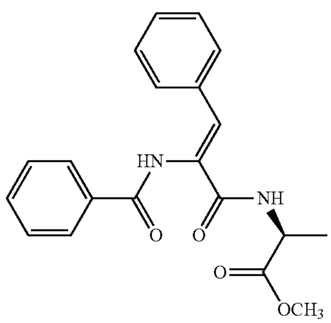 [SMILES: COC(=O)[C@H](C)NC(=O)/C(=C/c1ccccc1)NC(=O)c1ccccc1] | ¹H NMR (400 MHz, CDCl₃) δ 8.44 (s, 1H), 7.84 (d, J = 7.3 Hz, 2H), 7.49 (t, J = 7.3 Hz, 1H), 7.38 (t, J = 7.2 Hz, 4H), 7.32-7.22 (m, 4H), 7.04 (s, 1H), 4.61-4.50 (m, 1H), 3.65 (s, 3H), 1.39 (d, J = 7.1 Hz, 3H). | 61.5 | White solid |
| 35 | 139-141 | 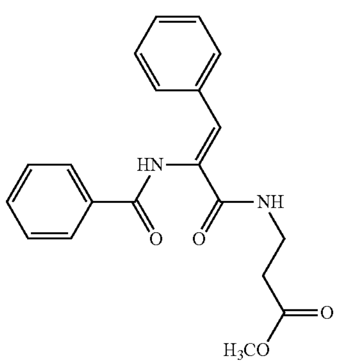 [SMILES: COC(=O)CCNC(=O)/C(=C/c1ccccc1)NC(=O)c1ccccc1] | ¹H NMR (400 MHz, CDCl₃) δ 8.30 (s, 1H), 7.87 (d, J = 7.3 Hz, 2H), 7.54 (t, J = 7.3 Hz, 1H), 7.48-7.39 (m, 4H), 7.38-7.28 (m, 3H), 7.06 (s, 1H), 6.95 (s, 1H), 3.67 (s, 3H), 3.55 (dd, J = 12.0, 6.0 Hz, 2H), 2.56 (t, J = 5.8 Hz, 2H). | 50.8 | White solid |
| 36 | 110-111 | 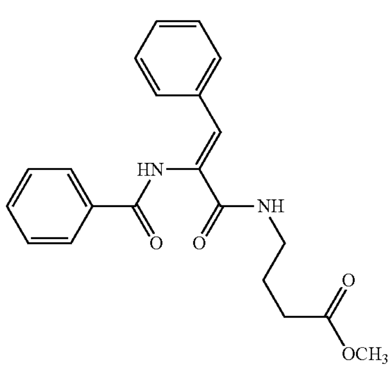 [SMILES: COC(=O)CCCNC(=O)/C(=C/c1ccccc1)NC(=O)c1ccccc1] | ¹H NMR (400 MHz, CDCl₃) δ 8.97 (d, J = 11.9 Hz, 1H), 7.85 (d, J = 7.5 Hz, 2H), 7.45 (t, J = 7.2 Hz, 1H), 7.31 (t, J = 12.6 Hz, 5H), 7.26-7.14 (m, 3H), 6.69 (s, 1H), 3.59 (s, 3H), 3.10 (s, 2H), 2.24 (t, J = 6.6 Hz, 2H), 1.78-1.59 (m, 2H). | 92.6 | Light yellow solid |

TABLE 1-continued

Structure and physical and chemical parameters of the α-amino acrylic derivatives I and intermediates of the present invention

| Number | m.p./ °C. | Structure | ¹H NMR | Yield % | Shape |
|---|---|---|---|---|---|
| 37 | 155-157 | 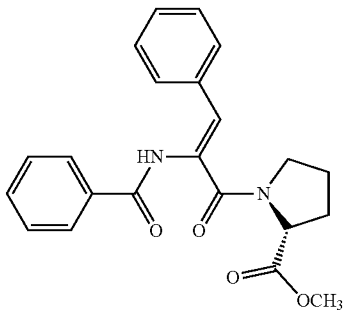 | ¹H NMR (400 MHz, DMSO) δ 10.35 (s, 1H), 8.06 (d, J = 7.3 Hz, 2H), 7.72-7.51 (m, 5H), 7.50-7.33 (m, 3H), 6.62 (s, 1H), 4.43 (dd, J = 8.1, 5.9 Hz, 1H), 3.84 (d, J = 5.3 Hz, 1H), 3.72 (s, 3H), 3.56 (s, 1H), 2.41-2.16 (m, 1H), 2.13-1.85 (m, 3H). | 85.7 | Light yellow solid |
| 38 | 147-149 | 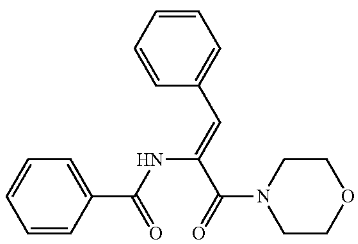 [SMILES: O=C(N/C(=C\c1ccccc1)C(=O)N1CCOCC1)c1ccccc1] | ¹H NMR (400 MHz, CDCl₃) δ 10.08-9.76 (m, 1H), 7.88 (d, J = 7.4 Hz, 2H), 7.66-7.15 (m, 8H), 6.02 (s, 1H), 3.64 (dd, J = 112.1, 67.5 Hz, 8H). | 97.4 | Light yellow |
| 39 | 185-186 | 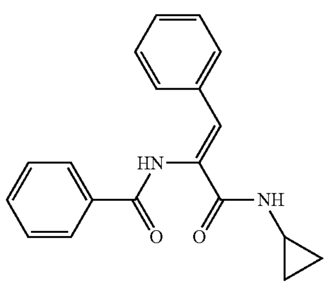 [SMILES: O=C(NC1CC1)/C(=C/c1ccccc1)NC(=O)c1ccccc1] | ¹H NMR (400 MHz, DMSO) δ 9.89 (s, 1H), 8.22 (d, J = 3.6 Hz, 1H), 8.00 (d, J = 7.4 Hz, 2H), 7.65-7.45 (m, 5H), 7.31 (dt, J = 23.7, 6.8 Hz, 3H), 7.09 (s, 1H), 2.76 (d, J = 3.6 Hz, 1H), 0.72-0.44 (m, 4H). | 91.3 | White solid |
| 40 | 204-206 | 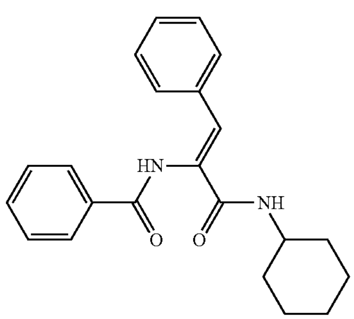 [SMILES: O=C(NC1CCCCC1)/C(=C/c1ccccc1)NC(=O)c1ccccc1] | ¹H NMR (400 MHz, DMSO) δ 9.88 (s, 1H), 7.96 (dd, J = 29.0, 7.8 Hz, 3H), 7.63-7.46 (m, 5H), 7.31 (dt, J = 25.3, 7.2 Hz, 3H), 7.10 (s, 1H), 3.66 (s, 1H), 1.73 (d, J = 15.7 Hz, 4H), 1.59 (d, J = 11.6 Hz, 1H), 1.27 (dd, J = 17.1, 8.3 Hz, 5H). | 63.4 | White solid |
| 41 | 107-109 | 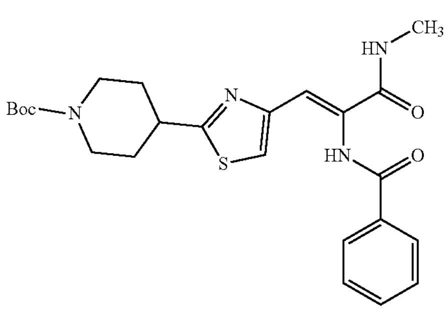 [SMILES: CNC(=O)/C(=C/c1csc(C2CCN(C(=O)OC(C)(C)C)CC2)n1)NC(=O)c1ccccc1] | ¹H NMR (400 MHz, CDCl₃) δ 11.43 (s, 1H), 8.02 (d, J = 7.5 Hz, 2H), 7.57 (d, J = 7.4 Hz, 1H), 7.48 (t, J = 7.6 Hz, 2H), 7.19 (s, 1H), 6.69 (d, J = 4.6 Hz, 1H), 6.59 (s, 1H), 4.27-4.05 (m, 2H), 3.05 (t, J = 3.6 Hz, 1H), 2.99 (d, J = 4.9 Hz, 3H), 2.81 (s, 2H), 1.96 (d, J = 12.2 Hz, 2H), 1.66 (td, J = 12.3, 4.1 Hz, 2H), 1.50 (s, 9H). | 54.8 | Yellow solid |

TABLE 1-continued

Structure and physical and chemical parameters of the α-amino acrylic derivatives I and intermediates of the present invention

| Number | m.p./ °C. | Structure | ¹H NMR | Yield % | Shape |
|---|---|---|---|---|---|
| 42 | 111-113 | 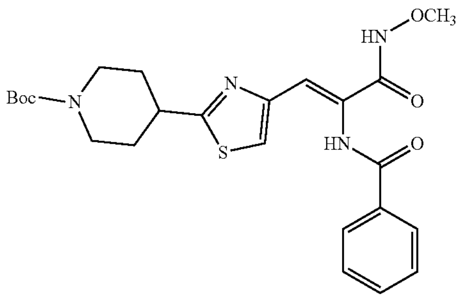 [SMILES: CONC(=O)/C(=C/c1csc(C2CCN(C(=O)OC(C)(C)C)CC2)n1)NC(=O)c1ccccc1] | ¹H NMR (400 MHz, CDCl₃) δ 11.56 (s, 1H), 9.91 (s, 1H), 7.98 (d, J = 7.5 Hz, 2H), 7.55 (t, J = 7.4 Hz, 1H), 7.45 (t, J = 7.6 Hz, 2H), 7.24 (s, 1H), 6.57 (s, 1H), 4.26-4.04 (m, 2H), 3.89 (s, 3H), 3.05 (ddd, J = 11.7, 8.1, 3.7 Hz, 1H), 2.81 (s, 2H), 1.96 (d, J = 11.8 Hz, 2H), 1.71-1.57 (m, 2H), 1.55-1.42 (m, 9H). | 63.6 | Yellow solid |
| 43 | 164-165 | 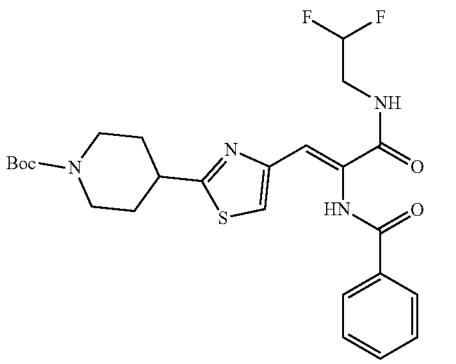 [SMILES: CC(C)(C)OC(=O)N1CCC(c2nc(/C=C(\NC(=O)c3ccccc3)C(=O)NCC(F)F)cs2)CC1] | ¹H NMR (400 MHz, CDCl₃) δ 11.43 (s, 1H), 7.99 (d, J = 7.4 Hz, 2H), 7.56 (t, J = 7.3 Hz, 1H), 7.46 (t, J = 7.6 Hz, 2H), 7.22 (s, 1H), 7.08 (t, J = 6.1 Hz, 1H), 6.56 (s, 1H), 6.00 (t, J = 56.2 Hz, 1H), 4.14 (s, 2H), 3.86-3.69 (m, 2H), 3.04 (tt, J = 11.5, 3.4 Hz, 1H), 2.81 (s, 2H), 1.96 (d, J = 12.1 Hz, 2H), 1.63 (qd, J = 12.5, 4.2 Hz, 2H), 1.49 (s, 9H). | 67.6 | Light yellow solid |
| 44 | 143-145 | 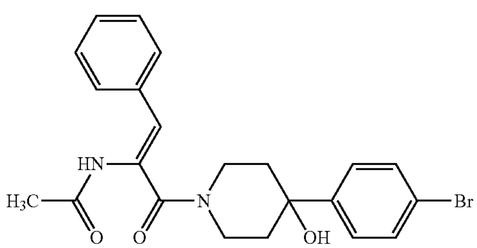 [SMILES: CC(=O)N/C(=C\c1ccccc1)C(=O)N1CCC(O)(c2ccc(Br)cc2)CC1] | ¹H NMR (400 MHz, DMSO) δ 9.82 (s, 1H), 7.65-7.22 (m, 9H), 6.15 (s, 1H), 5.27 (s, 1H), 4.24 (d, J = 12.3 Hz, 1H), 4.13-3.92 (m, 1H), 3.48 (t, J = 11.8 Hz, 1H), 3.08 (t, J = 12.1 Hz, 1H), 2.17 (s, 1H), 2.00 (s, 3H), 1.84 (s, 1H), 1.56 (dd, J = 42.8, 12.6 Hz, 2H). | 75.0 | White solid |
| 45 | 115-117 | 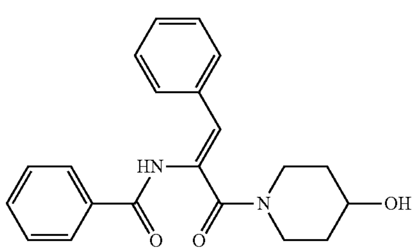 [SMILES: O=C(N/C(=C\c1ccccc1)C(=O)N1CCC(O)CC1)c1ccccc1] | ¹H NMR (400 MHz, CDCl₃) δ 9.47 (d, J = 6.6 Hz, 1H), 7.84 (d, J = 7.5 Hz, 2H), 7.47 (d, J = 7.5 Hz, 2H), 7.33 (ddd, J = 14.8, 13.0, 7.4 Hz, 6H), 6.06 (s, 1H), 4.10 (d, J = 6.5 Hz, 1H), 3.90 (s, 2H), 3.46 (s, 1H), 3.09 (s, 1H), 2.86-2.51 (m, 1H), 1.92 (s, 2H), 1.77-1.38 (m, 2H). | 98.9 | Light yellow solid |
| 46 | 192-194 | 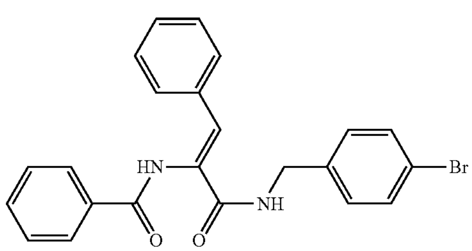 [SMILES: O=C(NCc1ccc(Br)cc1)/C(=C/c1ccccc1)NC(=O)c1ccccc1] | ¹H NMR (400 MHz, DMSO) δ 10.05 (s, 1H), 8.79 (s, 1H), 8.06 (d, J = 7.4 Hz, 2H), 7.72-7.46 (m, 7H), 7.34 (dd, J = 13.4, 8.3 Hz, 6H), 4.38 (d, J = 5.7 Hz, 2H). | 89.3 | White solid |

TABLE 1-continued

Structure and physical and chemical parameters of the α-amino acrylic derivatives I and intermediates of the present invention

| Number | m.p./°C. | Structure | ¹H NMR | Yield % | Shape |
|---|---|---|---|---|---|
| 47 | 101-103 | 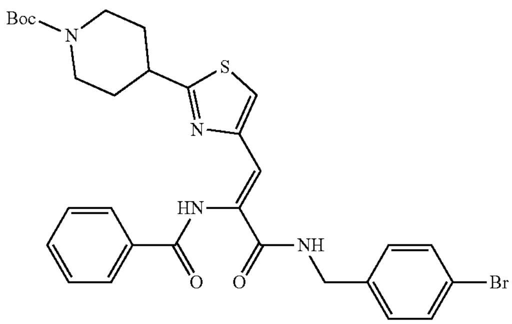 [SMILES: CC(C)(C)OC(=O)N1CCC(c2nc(/C=C(\NC(=O)c3ccccc3)C(=O)NCc3ccc(Br)cc3)cs2)CC1] | ¹H NMR (400 MHz, CDCl₃) δ 11.43 (s, 1H), 8.04 (d, J = 7.4 Hz, 2H), 7.69-7.40 (m, 5H), 7.38-7.19 (m, 4H), 6.64 (s, 1H), 4.59 (d, J = 5.6 Hz, 2H), 4.32-4.06 (m, 2H), 3.08 (s, 1H), 2.85 (s, 2H), 2.00 (d, J = 12.5 Hz, 2H), 1.67 (qd, J = 12.5, 4.0 Hz, 2H), 1.55 (s, 9H). | 90.5 | Light yellow solid |
| 48 | 143-144 | 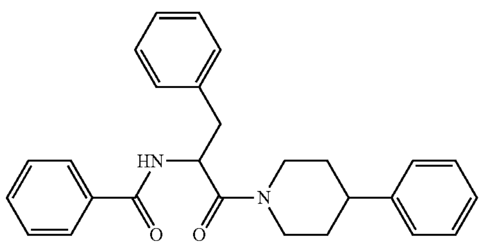 [SMILES: O=C(NC(Cc1ccccc1)C(=O)N1CCC(c2ccccc2)CC1)c1ccccc1] | ¹H NMR (400 MHz, CDCl₃) δ 7.99-6.96 (m, 16H), 5.64-5.37 (m, 1H), 4.77 (d, J = 9.3 Hz, 1H), 3.95 (dd, J = 56.4, 13.3 Hz, 1H), 3.29-3.03 (m, 2H), 2.77-2.51 (m, 2H), 1.99-1.17 (m, 5H). | 96.8 | White solid |
| 49 | 101-103 | 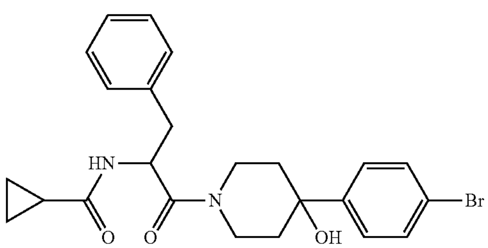 [SMILES: O=C(NC(Cc1ccccc1)C(=O)N1CCC(O)(c2ccc(Br)cc2)CC1)C1CC1] | ¹H NMR (400 MHz, DMSO) δ 8.63 (d, J = 7.6 Hz, 1H), 7.60-7.13 (m, 9H), 5.22 (d, J = 19.0 Hz, 1H), 5.02 (dd, J = 16.6, 7.9 Hz, 1H), 4.31 (s, 1H), 3.75 (t, J = 15.5 Hz, 1H), 3.24 (t, J = 29.9 Hz, 1H), 3.00 (d, J = 8.5 Hz, 1H), 2.94-2.78 (m, 2H), 2.05-1.43 (m, 4H), 0.85 (s, 1H), 0.62 (dd, J = 14.8, 6.6 Hz, 4H). | 63.4 | White solid |
| 50 | 200-202 | 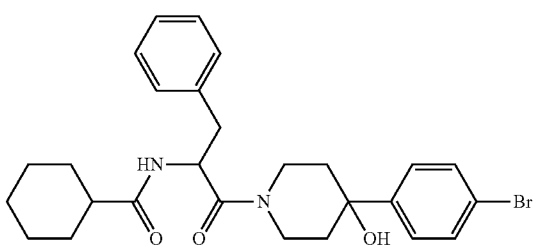 [SMILES: O=C(NC(Cc1ccccc1)C(=O)N1CCC(O)(c2ccc(Br)cc2)CC1)C1CCCCC1] | ¹H NMR (400 MHz, DMSO) δ 8.21 (t, J = 6.8 Hz, 1H), 7.66-7.13 (m, 8H), 5.29 (d, J = 20.8 Hz, 1H), 5.12-4.93 (m, 1H), 4.49-4.26 (m, 1H), 3.84 (d, J = 12.4 Hz, 1H), 3.31 (d, J = 15.1 Hz, 1H), 3.10-2.98 (m, 1H), 2.98-2.78 (m, 2H), 2.20 (s, 1H), 2.04 (s, 1H), 1.78-1.41 (m, 7H), 1.21 (d, J = 6.9 Hz, 6H). | 97.3 | White solid |
| 51 | 180-182 | 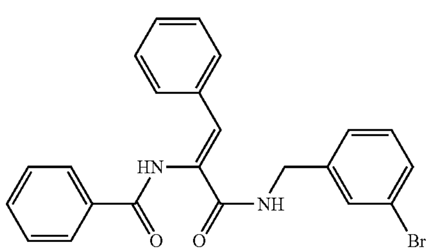 [SMILES: O=C(NCc1cccc(Br)c1)/C(=C/c1ccccc1)NC(=O)c1ccccc1] | ¹H NMR (400 MHz, DMSO) δ 10.05 (s, 1H), 8.78 (t, J = 6.0 Hz, 1H), 8.06 (d, J = 7.3 Hz, 2H), 7.64-7.49 (m, 6H), 7.43 (d, J = 7.7 Hz, 1H), 7.39-7.22 (m, 6H), 4.40 (d, J = 6.0 Hz, 2H). | 96.4 | White solid |

TABLE 1-continued

Structure and physical and chemical parameters of the α-amino acrylic derivatives I and intermediates of the present invention

| Number | m.p./ °C. | Structure | ¹H NMR | Yield % | Shape |
|---|---|---|---|---|---|
| 52 | 178-180 | 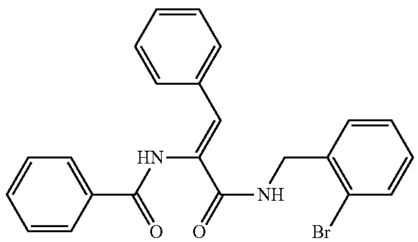 [SMILES: O=C(NCc1ccccc1Br)/C(=C/c1ccccc1)NC(=O)c1ccccc1] | ¹H NMR (400 MHz, DMSO) δ 10.11 (s, 1H), 8.78 (t, J = 6.0 Hz, 1H), 8.07 (d, J = 7.2 Hz, 2H), 7.65-7.45 (m, 7H), 7.44-7.27 (m, 5H), 7.21 (td, J = 7.8, 1.5 Hz, 1H), 4.41 (d, J = 5.9 Hz, 2H). | 89.3 | White solid |
| 53 | 169-171 | 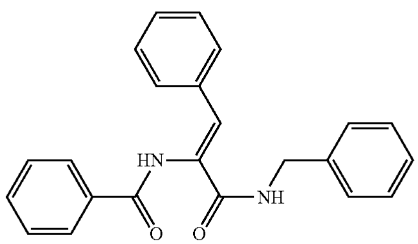 [SMILES: O=C(NCc1ccccc1)/C(=C/c1ccccc1)NC(=O)c1ccccc1] | ¹H NMR (400 MHz, DMSO) δ 10.05 (s, 1H), 8.79 (s, 1H), 8.08 (d, J = 7.3 Hz, 2H), 7.72-7.52 (m, 5H), 7.34 (dd, J = 30.5, 17.5 Hz, 9H), 4.44 (d, J = 5.3 Hz, 2H). | 88.9 | White solid |
| 54 | 138-140 | 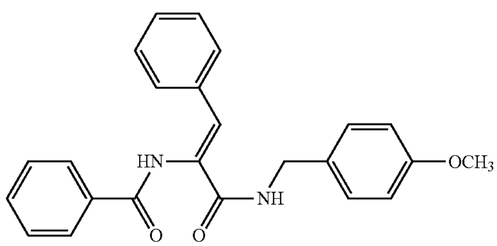 [SMILES: COc1ccc(CNC(=O)/C(=C/c2ccccc2)NC(=O)c2ccccc2)cc1] | ¹H NMR (400 MHz, DMSO) δ 9.98 (s, 1H), 8.68 (t, J = 5.8 Hz, 1H), 8.03 (d, J = 7.5 Hz, 2H), 7.56 (dd, J = 17.2, 7.4 Hz, 5H), 7.42-7.20 (m, 6H), 6.88 (d, J = 8.4 Hz, 2H), 4.33 (d, J = 5.8 Hz, 2H), 3.73 (s, 3H). | 88.0 | White solid |
| 55 | 199-201 | 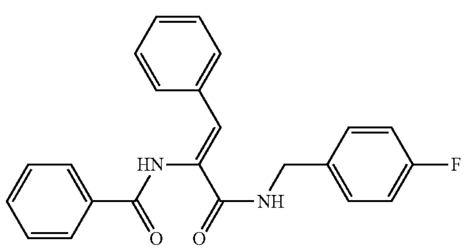 [SMILES: O=C(NCc1ccc(F)cc1)/C(=C/c1ccccc1)NC(=O)c1ccccc1] | ¹H NMR (400 MHz, DMSO) δ 10.03 (s, 1H), 8.77 (s, 1H), 8.05 (d, J = 7.1 Hz, 2H), 7.57 (dd, J = 20.2, 7.0 Hz, 5H), 7.35 (dd, J = 15.1, 6.7 Hz, 6H), 7.16 (t, J = 8.3 Hz, 2H), 4.38 (d, J = 4.7 Hz, 2H). | 96.4 | White solid |
| 56 | 202-204 | 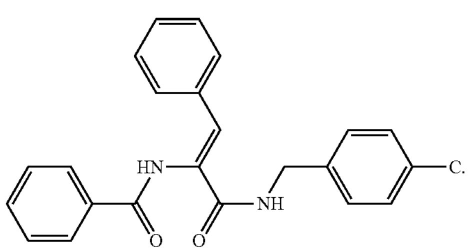 | ¹H NMR (400 MHz, DMSO) δ 10.04 (s, 1H), 8.78 (s, 1H), 8.05 (d, J = 7.8 Hz, 2H), 7.57 (dd, J = 21.0, 7.0 Hz, 5H), 7.44-7.26 (m, 8H), 4.40 (d, J = 5.7 Hz, 2H). | 80.0 | White solid |
| 57 | 167-168 | 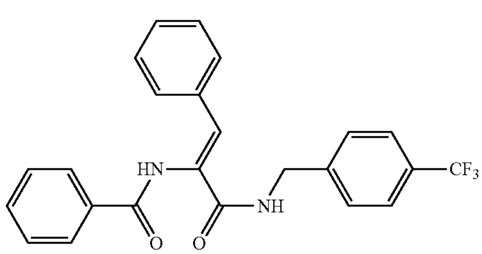 [SMILES: O=C(NCc1ccc(C(F)(F)F)cc1)/C(=C/c1ccccc1)NC(=O)c1ccccc1] | ¹H NMR (400 MHz, DMSO) δ 10.07 (s, 1H), 8.85 (s, 1H), 8.06 (d, J = 6.6 Hz, 2H), 7.70 (d, J = 7.8 Hz, 2H), 7.55 (dd, J = 17.4, 9.6 Hz, 7H), 7.35 (dt, J = 14.1, 7.0 Hz, 4H), 4.48 (s, 2H). | 87.5 | White solid |

TABLE 1-continued

Structure and physical and chemical parameters of the α-amino acrylic derivatives I and intermediates of the present invention

| Number | m.p./ °C. | Structure | ¹H NMR | Yield % | Shape |
|---|---|---|---|---|---|
| 58 | 210-212 | 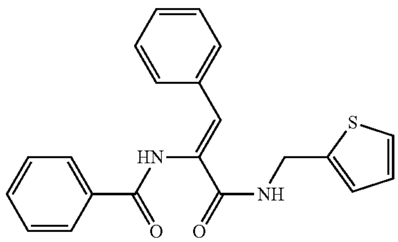 [SMILES: O=C(NCc1cccs1)/C(=C/c1ccccc1)NC(=O)c1ccccc1] | ¹H NMR (400 MHz, DMSO) δ 9.96 (s, 1H), 8.82 (t, J = 5.9 Hz, 1H), 8.02 (d, J = 7.3 Hz, 2H), 7.56 (tt, J = 14.9, 7.3 Hz, 5H), 7.41-7.27 (m, 5H), 7.01 (d, J = 2.6 Hz, 1H), 6.96 (dd, J = 4.9, 3.5 Hz, 1H), 4.53 (d, J = 5.9 Hz, 2H). | 78.3 | White solid |
| 59 | 187-189 | 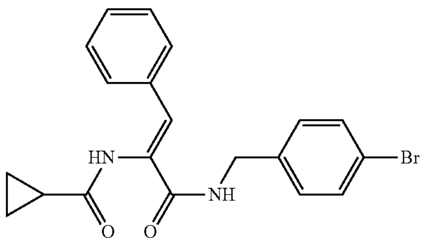 [SMILES: O=C(NCc1ccc(Br)cc1)/C(=C/c1ccccc1)NC(=O)C1CC1] | ¹H NMR (400 MHz, DMSO) δ 9.78 (s, 1H), 8.65 (s, 1H), 7.62-7.12 (m, 10H), 6.99 (s, 1H), 4.34 (d, J = 4.8 Hz, 2H), 1.86 (s, 1H), 1.24 (s, 1H), 0.77 (d, J = 7.4 Hz, 3H). | 61.0 | Yellow solid |
| 60 | 215-216 | 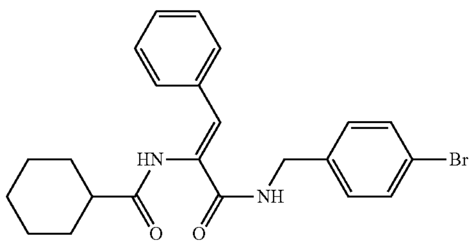 [SMILES: O=C(NCc1ccc(Br)cc1)/C(=C/c1ccccc1)NC(=O)C1CCCCC1] | ¹H NMR (400 MHz, DMSO) δ 9.37 (s, 1H), 8.50 (t, J = 6.0 Hz, 1H), 7.52 (dd, J = 12.9, 7.9 Hz, 4H), 7.39 (t, J = 7.4 Hz, 2H), 7.30 (dd, J = 18.6, 7.8 Hz, 3H), 7.05 (s, 1H), 4.34 (d, J = 6.0 Hz, 2H), 2.40 (s, 1H), 1.87 (d, J = 12.2 Hz, 2H), 1.74 (d, J = 11.7 Hz, 2H), 1.64 (d, J = 8.3 Hz, 1H), 1.36 (s, 1H), 1.34-1.28 (m, 2H), 1.25-1.19 (m, 2H). | 65.6 | Light yellow solid |
| 61 | 168-170 | 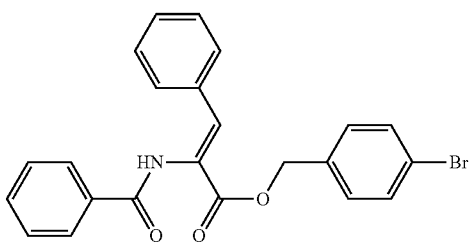 [SMILES: O=C(OCc1ccc(Br)cc1)/C(=C/c1ccccc1)NC(=O)c1ccccc1] | ¹H NMR (400 MHz, DMSO) δ 8.31 (d, J = 7.6 Hz, 2H), 8.13 (d, J = 7.6 Hz, 2H), 7.73 (t, J = 7.2 Hz, 1H), 7.58 (tt, J = 19.7, 10.2 Hz, 8H), 7.37 (dd, J = 20.0, 7.8 Hz, 3H), 4.75 (s, 2H). | 47.9 | Yellow solid |
| 62 | 198-200 | 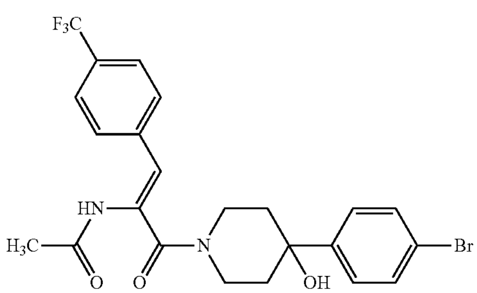 [SMILES: CC(=O)N/C(=C\c1ccc(C(F)(F)F)cc1)C(=O)N1CCC(O)(c2ccc(Br)cc2)CC1] | ¹H NMR (400 MHz, DMSO) δ 7.89-7.64 (m, 6H), 7.51 (s, 5H), 5.36 (s, 1H), 4.47 (d, J = 9.8 Hz, 1H), 3.48 (s, 1H), 3.19 (s, 1H), 1.97 (s, 3H), 1.71 (s, 2H), 1.52 (d, J = 11.9 Hz, 2H). | 32.4 | White solid |
| 63 | 121-123 | 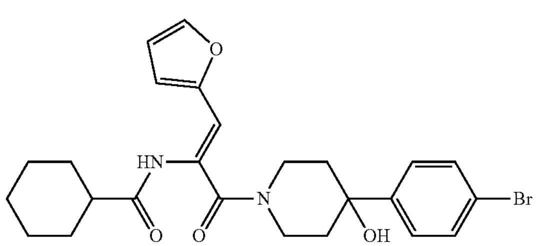 [SMILES: O=C(N/C(=C\c1ccco1)C(=O)N1CCC(O)(c2ccc(Br)cc2)CC1)C1CCCCC1] | ¹H NMR (400 MHz, DMSO) δ 9.41 (s, 1H), 7.76 (s, 1H), 7.49 (dd, J = 26.4, 8.4 Hz, 4H), 6.73-6.53 (m, 2H), 6.09 (s, 1H), 5.27 (s, 1H), 4.22 (d, J = 6.3 Hz, 1H), 3.88 (s, 1H), 3.06 (s, 1H), 2.43 (t, J = 11.2 Hz, 1H), 2.05 (s, 1H), 1.77 (dd, J = 30.2, 10.1 Hz, 5H), 1.68-1.47 (m, 3H), 1.46-1.09 (m, 6H). | 69.0 | Orange solid |

TABLE 1-continued

Structure and physical and chemical parameters of the α-amino acrylic derivatives I and intermediates of the present invention

| Number | m.p./ °C. | Structure | $^1$H NMR | Yield % | Shape |
|---|---|---|---|---|---|
| 64 | 82-84 | 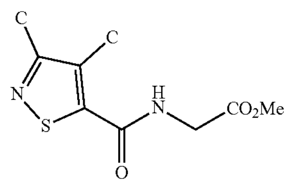 | $^1$H NMR (400 MHz, CDCl$_3$) δ 7.48 (s, 1H), 4.29 (d, J = 5.0 Hz, 2H), 3.85 (s, 3H). | 57.0 | White solid |
| 65 | 183-185 | 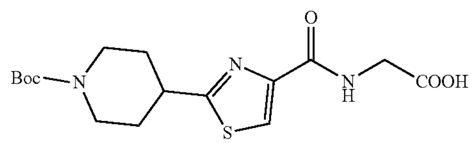 [SMILES: CC(C)(C)OC(=O)N1CCC(c2nc(C(=O)NCC(=O)O)cs2)CC1] | $^1$H NMR (400 MHz, DMSO) δ 12.67 (s, 1H), 8.52 (t, J = 6.0 Hz, 1H), 8.19 (s, 1H), 4.10-3.98 (m, 2H), 3.92 (d, J = 6.1 Hz, 2H), 3.31-3.19 (m, 1H), 2.91 (s, 2H), 2.06 (d, J = 10.7 Hz, 2H), 1.61 (ddd, J = 16.1, 12.3, 4.2 Hz, 2H), 1.41 (s, 9H). | 92.5 | White solid |
| 66 | 100-102 | 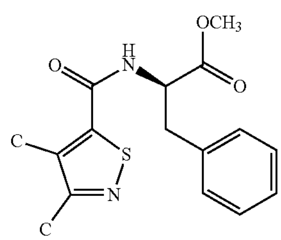 [SMILES: COC(=O)[C@@H](Cc1ccccc1)NC(=O)c1snc(C)c1C] | $^1$H NMR (400 MHz, CDCl$_3$) δ 7.40-7.26 (m, 4H), 7.15 (d, J = 6.3 Hz, 2H), 5.06 (dd, J = 12.9, 5.6 Hz, 1H), 3.82 (s, 3H), 3.29 (t, J = 5.5 Hz, 2H). | 69.1 | White solid |
| 67 | 193-195 | 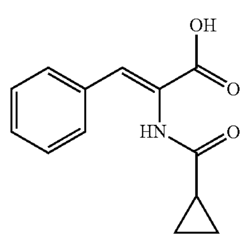 [SMILES: O=C(O)/C(=C/c1ccccc1)NC(=O)C1CC1] | $^1$H NMR (400 MHz, DMSO) δ 12.68 (s, 1H), 9.72 (s, 1H), 7.61 (d, J = 7.3 Hz, 1H), 7.46-7.34 (m, 3H), 7.21 (s, 2H), 1.86-1.77 (m, 1H), 0.74 (dd, J = 14.8, 6.0 Hz, 4H). | 71.0 | Yellow solid |
| 68 | 184-186 | 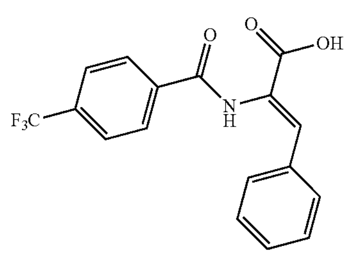 [SMILES: O=C(O)/C(=C/c1ccccc1)NC(=O)c1ccc(C(F)(F)F)cc1] | $^1$H NMR (400 MHz, CDCl$_3$) δ 14.59 (s, 1H), 11.78 (s, 1H), 10.22-8.49 (m, 10H). | 68.2 | White solid |
| 69 | 221-223 | 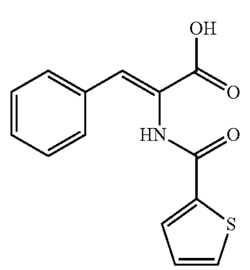 [SMILES: O=C(O)/C(=C/c1ccccc1)NC(=O)c1cccs1] | $^1$H NMR (400 MHz, DMSO) δ 12.89 (s, 1H), 10.04 (d, J = 9.7 Hz, 1H), 8.39-7.08 (m, 9H). | 90.7 | Yellow solid |

TABLE 1-continued

Structure and physical and chemical parameters of the α-amino acrylic derivatives I and intermediates of the present invention

| Number | m.p./ °C. | Structure | ¹H NMR | Yield % | Shape |
|---|---|---|---|---|---|
| 70 | 190-192 | 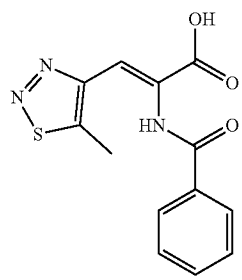 [SMILES: Cc1snnc1/C=C(\NC(=O)c1ccccc1)C(=O)O] | ¹H NMR (400 MHz, DMSO) δ 10.30 (s, 1H), 8.01-7.94 (m, 2H), 7.65-7.52 (m, 4H), 7.09 (s, 1H), 2.68 (s, 3H). | 90.1 | Yellow solid |
| 71 | 215-217 | 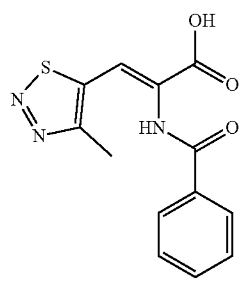 [SMILES: Cc1nnsc1/C=C(\NC(=O)c1ccccc1)C(=O)O] | ¹H NMR (400 MHz, DMSO) δ 13.41 (s, 1H), 10.20 (s, 1H), 8.04 (d, J = 7.4 Hz, 2H), 7.79-7.55 (m, 4H), 2.82 (s, 3H). | 76.3 | Orange solid |
| 72 | 236-238 | 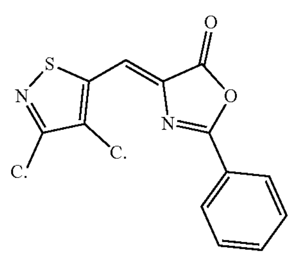 | ¹H NMR (400 MHz, CDCl₃) δ 8.28-8.14 (m, 2H), 7.71 (t, J = 7.4 Hz, 1H), 7.59 (t, J = 7.7 Hz, 2H), 7.42 (s, 1H). | 89.0 | Yellow solid |
| 73 | 189-191 | 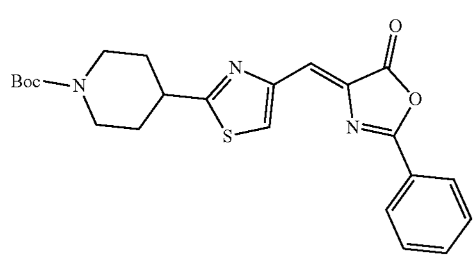 [SMILES: CC(C)(C)OC(=O)N1CCC(c2nc(/C=C3\N=C(c4ccccc4)OC3=O)cs2)CC1] | ¹H NMR (400 MHz, CDCl₃) δ 8.70 (s, 1H), 8.20 (d, J = 7.3 Hz, 1H), 7.72-7.46 (m, 4H), 4.25 (s, 2H), 3.29-3.17 (m, 1H), 2.93 (s, 2H), 2.22-2.08 (m, 2H), 1.79 (dd, J = 12.4, 3.8 Hz, 2H), 1.50 (s, 9H). | 84.9 | Yellow solid |
| 74 | 125-127 | 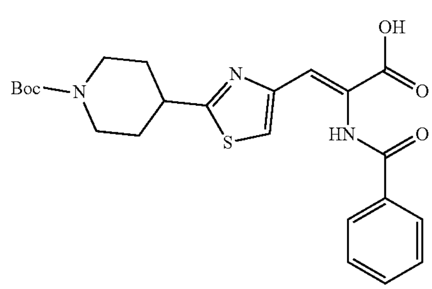 [SMILES: CC(C)(C)OC(=O)N1CCC(c2nc(/C=C(\NC(=O)c3ccccc3)C(=O)O)cs2)CC1] | ¹H NMR (400 MHz, DMSO) δ 10.76 (s, 1H), 8.33-7.23 (m, 6H), 6.91 (s, 1H), 3.92 (s, 2H), 3.19 (s, 1H), 2.83 (s, 2H), 1.93 (d, J = 9.5 Hz, 2H), 1.74-1.30 (m, 11H). | 86.0 | Light yellow solid |

TABLE 1-continued

Structure and physical and chemical parameters of the α-amino acrylic derivatives I and intermediates of the present invention

| Number | m.p./ °C. | Structure | ¹H NMR | Yield % | Shape |
|---|---|---|---|---|---|
| 75 | 194-195 | 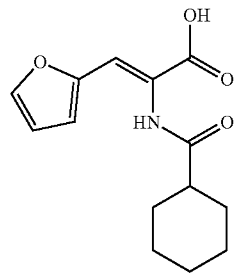 [SMILES: O=C(O)/C(=C/c1ccco1)NC(=O)C1CCCCC1] | ¹H NMR (400 MHz, DMSO) δ 12.58 (s, 1H), 9.19 (s, 1H), 7.82 (d, J = 1.4 Hz, 1H), 7.09 (s, 1H), 6.80 (d, J = 3.4 Hz, 1H), 6.63 (dd, J = 3.3, 1.8 Hz, 1H), 1.82 (d, J = 11.9 Hz, 2H), 1.75 (d, J = 12.4 Hz, 2H), 1.64 (d, J = 11.6 Hz, 1H), 1.27 (ddt, J = 14.2, 10.3, 9.6 Hz, 6H). | 68.3 | Yellow solid |
| 76 | 150-152 | 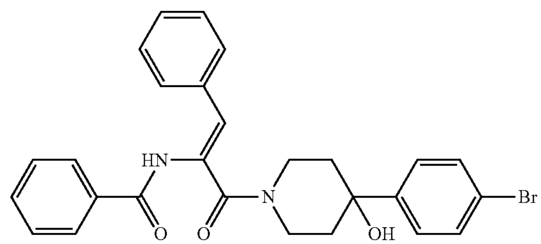 [SMILES: O=C(N/C(=C\c1ccccc1)C(=O)N1CCC(O)(c2ccc(Br)cc2)CC1)c1ccccc1] | ¹H NMR (400 MHz, DMSO) δ 10.32 (s, 1H), 8.02 (d, J = 7.3 Hz, 2H), 7.70-7.22 (m, 12H), 6.46 (s, 1H), 5.29 (s, 1H), 4.43-4.07 (m, 2H), 3.54 (s, 1H), 3.13 (s, 1H), 2.16 (s, 1H), 1.88 (s, 1H), 1.60 (dd, J = 38.7, 12.6 Hz, 2H). | 88.9 | White solid |
| 77 | 196-198 | 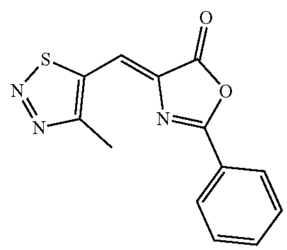 [SMILES: Cc1nnsc1/C=C1\N=C(c2ccccc2)OC1=O] | ¹H NMR (400 MHz, CDCl₃) δ 8.28-8.20 (m, 2H), 7.76-7.69 (m, 1H), 7.61 (t, J = 7.7 Hz, 2H), 7.42 (s, 1H), 2.92 (s, 3H). | 85.4 | Red solid |
| 78 | 149-151 | 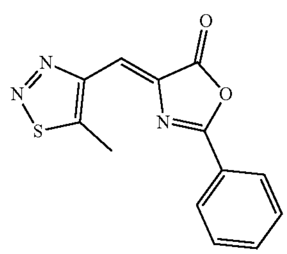 [SMILES: Cc1snnc1/C=C1\N=C(c2ccccc2)OC1=O] | ¹H NMR (400 MHz, CDCl₃) δ 8.25-8.20 (m, 2H), 8.12 (d, J = 7.4 Hz, 1H), 7.56 (d, J = 7.7 Hz, 2H), 7.49 (s, 1H), 2.89 (s, 3H). | 51.0 | Yellow solid |

TABLE 2

The names of the α-amino acrylic derivatives I are as follows:

| Number | Name |
|---|---|
| 1 | (Z)-N-[1-[[4-(4-bromophenyl)-4-hydroxy-1-piperidinyl]carbonyl]-2-phenylethenyl]cyclopropanecarboxamide |
| 2 | (Z)-N-[1-[[4-(4-bromophenyl)-4-hydroxy-1-piperidinyl]carbonyl]-2-phenylethenyl]cyclohexanecarboxamide |
| 3 | (Z)-N-[1-[[4-(4-bromophenyl)-4-hydroxy-1-piperidinyl]carbonyl]-2-phenylethenyl]-1-Boc-piperidine-4-carboxamide |
| 4 | (Z)-N-[1-[[4-(4-bromophenyl)-4-hydroxy-1-piperidinyl]carbonyl]-2-phenylethenyl]-1-piperidine-4-carboxamide-hydrochloride |
| 5 | (Z)-N-[1-[[4-(4-bromophenyl)-4-hydroxy-1-piperidinyl]carbonyl]-2-phenylethenyl]-4-methoxybenzamide |
| 6 | (Z)-N-[1-[[4-(4-bromophenyl)-4-hydroxy-1-piperidinyl]carbonyl]-2-phenylethenyl]-4-fluorobenzamide |
| 7 | (Z)-N-[1-[[4-(4-bromophenyl)-4-hydroxy-1-piperidinyl]carbonyl]-2-phenylethenyl]-4-chlorobenzamide |
| 8 | (Z)-N-[1-[[4-(4-bromophenyl)-4-hydroxy-1-piperidinyl]carbonyl]-2-phenylethenyl]-4-bromobenzamide |

TABLE 2-continued

The names of the α-amino acrylic derivatives I are as follows:

| Number | Name |
|---|---|
| 9 | (Z)-N-[1-[[4-(4-bromophenyl)-4-hydroxy-1-piperidinyl]carbonyl]-2-phenylethenyl]-4-(trifluoromethyl)benzamide |
| 10 | (Z)-N-[1-[[4-(4-bromophenyl)-4-hydroxy-1-piperidinyl]carbonyl]-2-phenylethenyl]-4-nitrobenzamide |
| 11 | (Z)-N-[1-[[4-(4-bromophenyl)-4-hydroxy-1-piperidinyl]carbonyl]-2-phenylethenyl]-3-nitrobenzamide |
| 12 | (Z)-N-[1-[[4-(4-bromophenyl)-4-hydroxy-1-piperidinyl]carbonyl]-2-phenylethenyl]-2-nitrobenzamide |
| 13 | (Z)-N-[1-[[4-(4-bromophenyl)-4-hydroxy-1-piperidinyl]carbonyl]-2-phenylethenyl]-2-furamide |
| 14 | (Z)-N-[1-[[4-(4-bromophenyl)-4-hydroxy-1-piperidinyl]carbonyl]-2-phenylethenyl]-2-thiophenecarboxamide |
| 15 | (Z)-N-[1-[[4-(4-bromophenyl)-4-hydroxy-1-piperidinyl]carbonyl]-2-(4-metylphenyl)ethenyl]benzamide |
| 16 | (Z)-N-[1-[[4-(4-bromophenyl)-4-hydroxy-1-piperidinyl]carbonyl]-2-(4-methoxyphenyl)ethenyl]benzamide |
| 17 | (Z)-N-[1-[[4-(4-bromophenyl)-4-hydroxy-1-piperidinyl]carbonyl]-2-(4-fluorophenyl)ethenyl]-benzamide |
| 18 | (Z)-N-[1-[[4-(4-bromophenyl)-4-hydroxy-1-piperidinyl]carbonyl]-2-(4-chlorophenyl)ethenyl]benzamide |
| 19 | (Z)-N-[1-[[4-(4-bromophenyl)-4-hydroxy-1-piperidinyl]carbonyl]-2-(4-bromophenyl)ethenyl]benzamide |
| 20 | (Z)-N-[1-[[4-(4-bromophenyl)-4-hydroxy-1-piperidinyl]carbonyl]-2-(4-trifluoromethylphenyl)ethenyl]benzamide |
| 21 | (Z)-N-[1-[[4-(4-bromophenyl)-4-hydroxy-1-piperidinyl]carbonyl]-2-(3-trifluoromethylphenyl)ethenyl]benzamide |
| 22 | (Z)-N-[1-[[4-(4-bromophenyl)-4-hydroxy-1-piperidinyl]carbonyl]-2-(2-(trifluoromethylphenyl)lethenyl]benzamide |
| 23 | (Z)-N-[1-[[4-(4-bromophenyl)-4-hydroxy-1-piperidinyl]carbonyl]-2-(4-nitrophenyl)ethenyl]benzamide |
| 24 | (Z)-N-[1-[[4-(4-bromophenyl)-4-hydroxy-1-piperidinyl]carbonyl]-2-(2-thienyl)ethenyl]benzamide |
| 25 | (Z)-N-[1-[[4-(4-bromophenyl)-4-hydroxy-1-piperidinyl]carbonyl]-2-(2-furanyl)ethenyl]benzamide |
| 26 | (Z)-N-[1-[[4-(4-bromophenyl)-4-hydroxy-1-piperidinyl]carbonyl]-2-(4-imidazole)ethenyl]benzamide |
| 27 | (Z)-N-[1-[[4-(4-bromophenyl)-4-hydroxy-1-piperidinyl]carbonyl]-2-[5-(4-methyl-1,2,3-thiadiazol)]ethenyl]benzamide |
| 28 | (Z)-N-[1-[[4-(4-bromophenyl)-4-hydroxy-1-piperidinyl]carbonyl]-2-[4-(5-methyl-1,2,3-thiadiazol)]ethenyl]benzamide |
| 29 | (Z)-N-[1-[[4-(4-bromophenyl)-4-hydroxy-1-piperidinyl]carbonyl]-2-[4-[2-[4-(1-Boc-piperidine)]thiazol]]ethenyl]benzamide |
| 30 | (Z)-N-[1-[[[4-[2-(ethylthiazole-4-carboxylate)]]-1-piperidinyl]carbonyl]-2-phenylethenyl]benzamide |
| 31 | (Z)-N-[1-[[[4-[2-(4-hydroxymethylthiazol)]]-1-piperidinyl]carbonyl]-2-phenylethenyl]benzamide |
| 32 | (Z)-N-[1-[(methylamino)carbonyl]-2-phenylethenyl]benzamide |
| 33 | (Z)-N-[1-[(methoxylamino)carbonyl]-2-phenylethenyl]benzamide |
| 34 | (S,Z)-N-[1-[[1-(2-methyl propanoate)amino]carbonyl]-2-phenylethenyl]benzamide |
| 35 | (Z)-N-[1-[[1-(3-methyl propionate)amino]carbonyl]-2-phenylethenyl]benzamide |
| 36 | (Z)-N-[1-[[1-(4-methylbutanoate)amino]carbonyl]-2-phenylethenyl]benzamide |
| 37 | (R,Z)-N-[1-[(2-methylpyrrolidinecarboxylate)]carbonyl-2-phenylethenyl]benzamide |
| 38 | (Z)-N-[1-(4-morpholinylcarbonyl)-2-phenylethenyl]benzamide |
| 39 | (Z)-N-[1-[(cyclopropylamino)carbonyl]-2-phenylethenyl]benzamide |
| 40 | (Z)-N-[1-[(cyclohexylamino)carbonyl]-2-phenylethenyl]benzamide |
| 41 | (Z)-N-[1-[(methylamino)carbonyl]-2-[4-[2-[4-(1-Boc-piperidine)]thiazol]]ethenyl]benzamide |
| 42 | (Z)-N-[1-[(methoxylamino)carbonyl]-2-[4-[2-[4-(1-Boc-piperidine)]thiazol]]ethenyl]benzamide |
| 43 | (Z)-N-[1-[(2,2-difluoroethylamino)carbonyl]-2-[4-[2-[4-(1-Boc-piperidine)]thiazol]]ethenyl]benzamide |
| 44 | (Z)-N-[1-[[4-(4-bromophenyl)-4-hydroxy-1-piperidinyl]carbonyl]-2-phenylethenyl]formamide |
| 45 | (Z)-N-[1-[(4-hydroxy-1-piperidinyl)carbonyl]-2-phenylethenyl]benzamide |
| 46 | N-[(1Z)-2-phenyl-1-[[(4-bromophenylmethyl)amino]carbonyl]ethenyl]benzamide |
| 47 | N-[(1Z)-2-[4-[2-[4-(1-Boc-piperidine)]thiazol]]-1-[[(4-bromophenylmethyl)amino]carbonyl]ethenyl]benzamide |
| 48 | N-[1-[[4-(4-phenyl)-1-piperidinyl]carbonyl]-2-phenylethyl]benzamide |
| 49 | N-[1-[[4-(4-bromophenyl)-4-hydroxy-1-piperidinyl]carbonyl]-2-phenylethyl]cyclopropanecarboxamide |
| 50 | N-[1-[[4-(4-bromophenyl)-4-hydroxy-1-piperidinyl]carbonyl]-2-phenylethyl]cyclohexanecarboxamide |
| 51 | N-[(1Z)-2-phenyl-1-[[(3-bromophenylmethyl)amino]carbonyl]ethenyl]benzamide |
| 52 | N-[(1Z)-2-phenyl-1-[[(2-bromophenylmethyl)amino]carbonyl]ethenyl]benzamide |
| 53 | N-[(1Z)-2-phenyl-1-[[(phenylmethyl)amino]carbonyl]ethenyl]benzamide |
| 54 | N-[(1Z)-2-phenyl-1-[[(4-methoxyphenylmethyl)amino]carbonyl]ethenyl]benzamide |

TABLE 2-continued

The names of the α-amino acrylic derivatives I are as follows:

| Number | Name |
|---|---|
| 55 | N-[(1Z)-2-phenyl-1-[[(4-fluorophenylmethyl)amino]carbonyl]ethenyl]benzamide |
| 56 | N-[(1Z)-2-phenyl-1-[[(4-chlorophenylmethyl)amino]carbonyl]ethenyl]benzamide |
| 57 | N-[(1Z)-2-phenyl-1-[[(4-trifluoromethylphenylmethyl)amino]carbonyl]ethenyl]benzamide |
| 58 | N-[(1Z)-2-phenyl-1-[[(2-thienylmethyl)amino]carbonyl]ethenyl]benzamide |
| 59 | N-[(1Z)-2-phenyl-1-[[(4-bromophenylmethyl)amino]carbonyl]ethenyl]cyclopropanecarboxamide |
| 60 | N-[(1Z)-2-phenyl-1-[[(4-bromophenylmethyl)amino]carbonyl]ethenyl]cyclohexanecarboxamide |
| 61 | N-[(1Z)-2-phenyl-1-[(4-bromophenymethoxyl)carbonyl]ethenyl]benzamide |
| 62 | (Z)-N-[1-[[4-(4-bromophenyl)-4-hydroxy-1-piperidinyl]carbonyl]-2-(3-trifluoromethylphenyl)ethenyl]formamide |
| 63 | (Z)-N-[1-[[4-(4-bromophenyl)-4-hydroxy-1-piperidinyl]carbonyl]-2-(2-furanyl)ethenyl]cyclohexanecarboxamide |
| 64 | Methyl 3,4-dichloroisothiazole-5-carboxamindoacetate |
| 65 | N-[[4-[2-[4-(1-Boc-piperidine)]thiazol]]formyl]ethanoic acid |
| 66 | (S)-methyl 2-(3,4-dichloroisothiazole-5-carboxamido)-3-phenylpropanoate |
| 67 | (Z)-2-cyclopropanoylamino-3-phenylpropenoic acid |
| 68 | (Z)-2-[4-(trifluoromethyl)benzoylamino]-3-phenylpropenoic acid |
| 69 | (Z)-2-(2-thiophanoylamino)-3-phenylpropenoic acid |
| 70 | (Z)-2-benzoylamino-3-[4-(5-methyl-1,2,3-thiadiazol)]propenoic acid |
| 71 | (Z)-2-benzoylamino-3-[5-(4-methyl-1,2,3-thiadiazol)]propenoic acid |
| 72 | (4Z)-4-[2-[5-(3,4-dichloroisothiazole)]ethenyl]-2-phenyl-1,3-oxazol-5-(4H)-one |
| 73 | (4Z)-4-[2-[4-[2-[4-(1-Boc-piperidine)]thiazol]ethenyl]-2-phenyl-1,3-oxazol-5-(4H)-one |
| 74 | (Z)-2-benzoylamino-3-[4-[2-[4-(1-Boc-piperidine)]thiazol]]propenoic acid |
| 75 | (Z)-2-benzoylamino-3-(2-furanyl)propenoic acid |
| 76 | (Z)-N-[1-[[4-(4-bromophenyl)-4-hydroxy-1-piperidinyl]carbonyl]-2-phenylethenyl]benzamide |
| 77 | (4Z)-4-[5-(4-methyl-1,2,3-thiadiazol)ethenyl]-2-phenyl-1,3-oxazol-5-(4H)-one |
| 78 | (4Z)-4-[4-(5-methyl-1,2,3-thiadiazol)ethenyl]-2-phenyl-1,3-oxazol-5-(4H)-one |

TABLE 3

Anti-TMV activity of the α-amino acrylic derivatives I of the present invention (100 μg/mL, inhibition/%)

| Number | Curative effect | Inactivation effect | Protection effect | Induction effect |
|---|---|---|---|---|
| 1 | 54 | 83 | 48 | 11 |
| 2 | 50 | 81 | 43 | 77 |
| 3 | 59 | 14 | 51 | 0 |
| 4 | 0 | 3 | 1 | 1 |
| 5 | 1 | 49 | 48 | 2 |
| 6 | 15 | 50 | 45 | 6 |
| 7 | 39 | 31 | 50 | 1 |
| 8 | 0 | 19 | 1 | 50 |
| 9 | 50 | 15 | 60 | 10 |
| 10 | 39 | 62 | 13 | 48 |
| 11 | 78 | 71 | 5 | 33 |
| 12 | 56 | 28 | 23 | 0 |
| 13 | 47 | 69 | 26 | 30 |
| 14 | 39 | 30 | 34 | 52 |
| 15 | 20 | 0 | 0 | 41 |
| 16 | 0 | 1 | 57 | 8 |
| 17 | 0 | 1 | 33 | 3 |
| 18 | 0 | 27 | 39 | 34 |
| 19 | 0 | 0 | 46 | 0 |
| 20 | 0 | 0 | 52 | 53 |
| 21 | 35 | 58 | 46 | 9 |
| 22 | 59 | 58 | 0 | 22 |
| 23 | 0 | 4 | 59 | 11 |
| 24 | 0 | 1 | 36 | 37 |
| 25 | 55 | 31 | 46 | 17 |
| 26 | 0 | 21 | 1 | 1 |
| 27 | 3 | 34 | 37 | 0 |
| 28 | 43 | 3 | 36 | 4 |
| 29 | 36 | 0 | 0 | 2 |
| 30 | 3 | 0 | 0 | 2 |
| 31 | 0 | 0 | 0 | 33 |
| 32 | 0 | 25 | 58 | 10 |
| 33 | 3 | 0 | 1 | 45 |
| 34 | 0 | 0 | 0 | 50 |
| 35 | 0 | 16 | 3 | 23 |
| 36 | 36 | 0 | 13 | 41 |
| 37 | 25 | 0 | 2 | 40 |
| 38 | 0 | 0 | 38 | 46 |
| 39 | 18 | 0 | 10 | 34 |
| 40 | 0 | 0 | 0 | 45 |
| 41 | 0 | 0 | 30 | 2 |
| 42 | 0 | 0 | 41 | 20 |
| 43 | 30 | 27 | 2 | 31 |
| 44 | 82 | 13 | 23 | 39 |
| 45 | 30 | 22 | 54 | 52 |
| 46 | 33 | 64 | 41 | 44 |
| 47 | 56 | 0 | 41 | 53 |
| 48 | 25 | 32 | 2 | 27 |
| 49 | 29 | 31 | 41 | 21 |
| 50 | 37 | 34 | 47 | 34 |
| 51 | 12 | 69 | 11 | 14 |
| 52 | 12 | 31 | 20 | 47 |
| 53 | 55 | 58 | 33 | 0 |
| 54 | 49 | 28 | 0 | 0 |
| 55 | 45 | 59 | 0 | 4 |
| 56 | 30 | 58 | 0 | 4 |
| 57 | 52 | 61 | 4 | 0 |
| 58 | 17 | 0 | 0 | 2 |
| 59 | 80 | 39 | 41 | 26 |
| 60 | 16 | 53 | 28 | 18 |
| 61 | 0 | 13 | 16 | 0 |
| 62 | 0 | 86 | 29 | 45 |
| 63 | 36 | 50 | 53 | 9 |
| 64 | 58 | 45 | 43 | 51 |
| 65 | 0 | 40 | 39 | 38 |
| 66 | 0 | 21 | 83 | 43 |
| 67 | 52 | 57 | 78 | 34 |
| 68 | 0 | 3 | 37 | 34 |
| 69 | 0 | 1 | 27 | 45 |
| 70 | 37 | 3 | 17 | 37 |

TABLE 3-continued

Anti-TMV activity of the α-amino acrylic derivatives I of the present invention (100 μg/mL, inhibition/%)

| Number | Curative effect | Inactivation effect | Protection effect | Induction effect |
|---|---|---|---|---|
| 71 | 0 | 67 | 53 | 27 |
| 72 | 55 | 3 | 45 | 38 |
| 73 | 0 | 59 | 11 | 8 |
| 74 | 3 | 0 | 48 | 63 |
| 75 | 19 | 53 | 14 | 77 |
| 76 | 0 | 29 | 38 | 15 |
| 77 | 0 | 0 | 40 | 44 |
| 78 | 0 | 47 | 0 | 68 |
| Ribavirin | 28 | 81 | 58 | 4 |
| BTH | 50 | 63 | 76 | 96 |
| TDL | 49 | 55 | 32 | 73 |
| Ningnanmycin | 62 | 58 | 71 | 82 |

TABLE 4

Fungicidal activity of the α-amino acrylic derivatives I of the present invention (50 μg/mL, inhibition/%)

| Number | AS | CA | GZ | PP | BC | SS | RC | PS | PI |
|---|---|---|---|---|---|---|---|---|---|
| 1 | 21 | 16 | 26 | 10 | 21 | 83 | 29 | 14 | 27 |
| 2 | 15 | 12 | 22 | 7 | 15 | 100 | 16 | 19 | 23 |
| 3 | 32 | 25 | 34 | 21 | 24 | 75 | 26 | 23 | 19 |
| 4 | 21 | 6 | 43 | 12 | 24 | 47 | 23 | 9 | 11 |
| 5 | 13 | 9 | 11 | 7 | 13 | 80 | 7 | 13 | 18 |
| 6 | 31 | 49 | 44 | 49 | 48 | 96 | 51 | 54 | 50 |
| 7 | 25 | 18 | 71 | 12 | 21 | 44 | 18 | 20 | 16 |
| 8 | 21 | 18 | 29 | 6 | 18 | 50 | 23 | 20 | 26 |
| 9 | 15 | 14 | 0 | 7 | 13 | 100 | 11 | 17 | 18 |
| 10 | 8 | 9 | 17 | 7 | 11 | 86 | 16 | 17 | 18 |
| 11 | 24 | 25 | 34 | 21 | 12 | 100 | 24 | 8 | 14 |
| 12 | 12 | 16 | 39 | 17 | 8 | 100 | 14 | 17 | 10 |
| 13 | 15 | 16 | 33 | 16 | 24 | 95 | 22 | 21 | 27 |
| 14 | 17 | 7 | 7 | 0 | 24 | 83 | 8 | 3 | 5 |
| 15 | 17 | 13 | 10 | 7 | 10 | 56 | 16 | 12 | 21 |
| 16 | 23 | 55 | 2 | 5 | 29 | 67 | 13 | 15 | 33 |
| 17 | 28 | 23 | 16 | 3 | 10 | 67 | 10 | 15 | 27 |
| 18 | 43 | 30 | 49 | 27 | 34 | 93 | 29 | 29 | 31 |
| 19 | 21 | 3 | 5 | 16 | 4 | 44 | 19 | 12 | 27 |
| 20 | 17 | 16 | 7 | 10 | 7 | 67 | 19 | 21 | 21 |
| 21 | 12 | 25 | 19 | 8 | 8 | 75 | 24 | 17 | 2 |
| 22 | 12 | 25 | 28 | 8 | 8 | 100 | 26 | 15 | 5 |
| 23 | 25 | 10 | 19 | 10 | 7 | 67 | 26 | 33 | 17 |
| 24 | 15 | 16 | 23 | 10 | 14 | 67 | 19 | 18 | 17 |
| 25 | 16 | 22 | 31 | 15 | 20 | 100 | 36 | 27 | 10 |
| 26 | 21 | 16 | 2 | 7 | 14 | 78 | 16 | 0 | 19 |
| 27 | 21 | 12 | 57 | 12 | 26 | 47 | 23 | 20 | 24 |
| 28 | 32 | 27 | 77 | 29 | 24 | 75 | 62 | 27 | 19 |
| 29 | 6 | 13 | 3 | 0 | 7 | 67 | 10 | 11 | 14 |
| 30 | 13 | 7 | 11 | 2 | 17 | 82 | 4 | 13 | 9 |
| 31 | 21 | 23 | 7 | 0 | 7 | 56 | 16 | 5 | 24 |
| 32 | 5 | 16 | 6 | 12 | 11 | 80 | 4 | 13 | 16 |
| 33 | 21 | 13 | 0 | 3 | 22 | 17 | 10 | 5 | 8 |
| 34 | 21 | 16 | 16 | 0 | 24 | 56 | 3 | 0 | 5 |
| 35 | 25 | 3 | 7 | 3 | 21 | 67 | 7 | 0 | 13 |
| 36 | 21 | 10 | 0 | 0 | 10 | 50 | 16 | 0 | 2 |
| 37 | 17 | 13 | 23 | 0 | 21 | 56 | 13 | 6 | 5 |
| 38 | 8 | 7 | 6 | 0 | 4 | 77 | 9 | 13 | 11 |
| 39 | 17 | 13 | 13 | 3 | 9 | 67 | 3 | 6 | 11 |
| 40 | 13 | 10 | 11 | 0 | 10 | 56 | 10 | 6 | 11 |
| 41 | 54 | 35 | 34 | 37 | 52 | 96 | 33 | 33 | 39 |
| 42 | 63 | 44 | 42 | 44 | 53 | 93 | 45 | 43 | 44 |
| 43 | 43 | 32 | 36 | 40 | 40 | 96 | 38 | 39 | 38 |
| 44 | 21 | 12 | 43 | 9 | 15 | 38 | 28 | 3 | 21 |
| 45 | 25 | 6 | 43 | 6 | 12 | 38 | 13 | 3 | 24 |
| 46 | 7 | 18 | 43 | 12 | 9 | 34 | 13 | 2 | 11 |
| 47 | 36 | 22 | 22 | 22 | 32 | 82 | 21 | 19 | 20 |
| 48 | 18 | 9 | 11 | 14 | 17 | 64 | 11 | 17 | 23 |
| 49 | 28 | 12 | 43 | 6 | 15 | 50 | 18 | 14 | 11 |
| 50 | 29 | 26 | 29 | 18 | 29 | 50 | 23 | 20 | 26 |
| 51 | 25 | 15 | 43 | 18 | 24 | 50 | 28 | 14 | 21 |
| 52 | 11 | 11 | 29 | 6 | 18 | 38 | 18 | 14 | 16 |
| 53 | 16 | 18 | 23 | 13 | 16 | 75 | 5 | 8 | 5 |
| 54 | 16 | 16 | 42 | 13 | 12 | 75 | 17 | 17 | 2 |
| 55 | 28 | 10 | 34 | 21 | 12 | 75 | 12 | 12 | 19 |
| 56 | 24 | 14 | 19 | 4 | 22 | 100 | 17 | 12 | 5 |
| 57 | 16 | 4 | 31 | 0 | 10 | 50 | 10 | 19 | 0 |
| 58 | 21 | 6 | 29 | 9 | 18 | 47 | 18 | 14 | 21 |
| 59 | 16 | 22 | 16 | 8 | 18 | 75 | 24 | 19 | 10 |
| 60 | 21 | 18 | 57 | 12 | 18 | 38 | 23 | 9 | 16 |
| 61 | 25 | 12 | 29 | 6 | 18 | 44 | 13 | 9 | 11 |
| 62 | 14 | 18 | 29 | 9 | 18 | 53 | 23 | 9 | 16 |
| 63 | 29 | 24 | 57 | 18 | 35 | 44 | 21 | 14 | 21 |
| 64 | 13 | 13 | 23 | 0 | 10 | 67 | 65 | 5 | 11 |
| 65 | 9 | 10 | 16 | 3 | 10 | 67 | 10 | 9 | 18 |
| 66 | 17 | 10 | 19 | 0 | 10 | 67 | 16 | 3 | 14 |
| 67 | 20 | 15 | 23 | 3 | 19 | 67 | 10 | 6 | 13 |
| 68 | 13 | 12 | 17 | 7 | 20 | 73 | 9 | 13 | 18 |
| 69 | 17 | 16 | 19 | 7 | 7 | 78 | 10 | 6 | 17 |
| 70 | 14 | 24 | 21 | 0 | 12 | 44 | 18 | 14 | 13 |
| 71 | 14 | 24 | 86 | 6 | 12 | 47 | 18 | 9 | 21 |
| 72 | 11 | 24 | 43 | 6 | 18 | 44 | 18 | 9 | 16 |
| 73 | 36 | 16 | 23 | 19 | 10 | 89 | 24 | 20 | 24 |
| 74 | 36 | 39 | 42 | 32 | 41 | 89 | 44 | 38 | 40 |
| 75 | 29 | 6 | 43 | 12 | 12 | 38 | 18 | 9 | 11 |
| 76 | 14 | 24 | 43 | 15 | 18 | 50 | 15 | 14 | 24 |
| 77 | 11 | 24 | 43 | 6 | 12 | 47 | 23 | 14 | 16 |
| 78 | 29 | 21 | 57 | 15 | 26 | 53 | 18 | 3 | 26 |
| Azoxystrobin | 79 | 81 | 100 | 81 | 78 | 100 | 67 | 92 | 91 |

TABLE 5

Toxicities ($EC_{90}$ values) of the α-amino acrylic derivatives I and intermediates of the present invention against *S. sclerotiorum* in vitro

| Number | Regression equation | $R^2$ | $EC_{90}$ (μg/mL) | Relative activity |
|---|---|---|---|---|
| 2 | y = 1.5978x + 1.8825 | 0.9394 | 565.31 | 0.39 |
| 6 | y = 2.4089x + 0.6474 | 0.9804 | 217.91 | 1.01 |
| 9 | y = 2.2176x + 0.8765 | 0.9866 | 273.3 | 0.81 |
| 11 | y = 6.5731x − 7.5595 | 1.0000 | 127.49 | 1.73 |
| 12 | y = 3.8680x − 2.5501 | 1.0000 | 191.79 | 1.15 |
| 13 | y = 3.3242x − 1.3352 | 1.0000 | 195.36 | 1.13 |
| 18 | y = 1.8833x + 1.4195 | 0.9115 | 380.88 | 0.58 |
| 22 | y = 2.7633x − 0.0722 | 0.9444 | 198.98 | 1.11 |
| 25 | y = 2.2909x + 0.9084 | 0.9520 | 221.17 | 1.00 |
| 41 | y = 1.9536x + 1.2523 | 0.8535 | 374.53 | 0.59 |
| 42 | y = 3.3688x − 1.0944 | 0.9999 | 154.52 | 1.43 |
| 43 | y = 4.1152x − 2.7195 | 0.9702 | 153.77 | 1.44 |
| 56 | y = 1.6078x + 1.2970 | 0.8196 | 1256.5 | 0.18 |

What is claimed is:

1. A α-amino acrylic derivative with a formula of

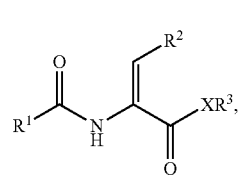

wherein:
$R^1$ is cyclopropyl or cyclohexyl,
$R^2$ is phenyl,
$XR^3$ is [4-(4-bromobenzene)-4-hydroxy]-1-piperidinyl.

* * * * *